US008293900B2

(12) United States Patent
Jian et al.

(10) Patent No.: US 8,293,900 B2
(45) Date of Patent: Oct. 23, 2012

(54) ACYLATED SPIROPIPERIDINE DERIVATIVES AS MELANOCORTIN-4 RECEPTOR MODULATORS

(75) Inventors: Tianying Jian, Westfield, NJ (US); Jian Liu, Edison, NJ (US); Ravi P. Nargund, East Brunswick, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 1248 days.

(21) Appl. No.: 11/992,262

(22) PCT Filed: Sep. 25, 2006

(86) PCT No.: PCT/US2006/037196
§ 371 (c)(1),
(2), (4) Date: Mar. 19, 2008

(87) PCT Pub. No.: WO2007/041052
PCT Pub. Date: Apr. 12, 2007

(65) Prior Publication Data
US 2009/0170863 A1     Jul. 2, 2009

Related U.S. Application Data

(60) Provisional application No. 60/721,678, filed on Sep. 29, 2005.

(51) Int. Cl.
*C07D 491/00* (2006.01)
*C07D 491/147* (2006.01)
(52) U.S. Cl. .......................................... 544/230; 546/17
(58) Field of Classification Search .................. None
See application file for complete search history.

(56) References Cited

U.S. PATENT DOCUMENTS

| | | | |
|---|---|---|---|
| 6,051,555 A | 4/2000 | Hadley | |
| 6,818,658 B2 | 11/2004 | Ujjainwalla et al. | |
| 2003/0092732 A1 | 5/2003 | Yu et al. | |
| 2003/0096827 A1 | 5/2003 | Yu et al. | |
| 2003/0232807 A1 | 12/2003 | Poindexter et al. | |
| 2004/0072847 A1* | 4/2004 | Bakthavatchalam et al. | 514/262.1 |
| 2004/0224901 A1 | 11/2004 | Chaturvedula et al. | |

FOREIGN PATENT DOCUMENTS

| | | |
|---|---|---|
| WO | WO 99/64002 | 12/1999 |
| WO | WO 00/74679 | 12/2000 |
| WO | WO 01/70337 | 9/2001 |
| WO | WO 01/70708 | 9/2001 |
| WO | WO 01/91752 | 12/2001 |
| WO | WO 02/15909 | 2/2002 |
| WO | WO 02/068387 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/068388 | 9/2002 |
| WO | WO 02/079146 | 10/2002 |
| WO | WO 03/007949 | 1/2003 |
| WO | WO 03/009847 | 2/2003 |
| WO | WO 03/009850 | 2/2003 |
| WO | WO 03/061660 | 7/2003 |
| WO | WO 03/068738 | 8/2003 |
| WO | WO 03/092690 | 11/2003 |
| WO | WO 03/093234 | 11/2003 |
| WO | WO 03/094918 | 11/2003 |
| WO | WO 2004/024720 | 3/2004 |
| WO | WO 2004/048345 | 6/2004 |
| WO | WO 2004/058735 | 7/2004 |
| WO | WO 2004/078716 | 9/2004 |
| WO | WO 2004/078717 | 9/2004 |
| WO | WO 2004/087159 | 10/2004 |
| WO | WO 2004/089307 | 10/2004 |
| WO | WO 2004/112793 | 12/2004 |
| WO | WO 2005/009950 | 2/2005 |
| WO | WO 2005/016913 | 2/2005 |
| WO | WO 2005/040109 | 5/2005 |
| WO | WO 2005/042516 | 5/2005 |
| WO | WO 2005/110992 | 11/2005 |
| WO | WO 2006/040329 | 4/2006 |

OTHER PUBLICATIONS

Guo et al., Discovery of Potent, Selective, and Orally Bioavailable 3H-spiro[isobenzofuran-1,40-piperidine] Based Melanocortin Subtype-4 Receptor Agonists, 20 Bioorg. & Med. Chem. Letts. 4895-4900 (2010).*
Richard B. Silverman, The Organic Chemistry of Drug Design and Drug Action, Chapter 2: Drug Discovery, Design, and Development, Academic Press, p. 5-51 (1992).*
S. Giraudo et al., "Feeding effects of hypothalamic injection of melanocortin 4-receptor ligands", Brain Research, vol. 809, pp. 302-306 (1998).
I. Corcos et et., "HP 228 is a potent agonist of melanocortin receptor 4, and significantly attenuates obesity and diabetes in Zucker fatty rats", Society for Neuroscience, vol. 23, Abstract 267.9, 27th meeting, p. 673 (1997).
C. W. Thornber, "Isosterism and Molecular Modification in Drug Design", Chemical Society Reviews, vol. 8, No. 4, pp. 563-580 (1979).

* cited by examiner

*Primary Examiner* — Janet Andres
*Assistant Examiner* — Timothy R Rozof
(74) *Attorney, Agent, or Firm* — Kenrick L. Vidale; John C. Todaro

(57) ABSTRACT

Certain novel N-acylated spiropiperidine derivatives are ligands of the human melanocortin receptor(s) and, in particular, are selective ligands of the human melanocortin-4 receptor (MC-4R). They are therefore useful for the treatment, control, or prevention of diseases and disorders responsive to the modulation of MC-4R, such as obesity, diabetes, nicotine addiction, alcoholism, sexual dysfunction, including erectile dysfunction and female sexual dysfunction.

7 Claims, No Drawings

ACYLATED SPIROPIPERIDINE DERIVATIVES AS MELANOCORTIN-4 RECEPTOR MODULATORS

CROSS-REFERENCE TO RELATED APPLICATIONS

This application is a U.S. National Phase application under 35 U.S.C. §371 of PCT Application No. PCT/US2006/037196, filed Sep. 25, 2006, which published as WO 2007/041052 on Apr. 12, 2007, and claims priority under 35 U.S.C. §119 from U.S. Provisional Application No. 60/721,678, filed Sep. 29, 2005.

FIELD OF THE INVENTION

The present invention relates to acylated spiropiperidine derivatives, their synthesis, and their use as melanocortin receptor (MC-R) ligands useful to modulate bodyweight. More particularly, the compounds of the present invention are ligands of the melanocortin-4 receptor (MC-4R) and are thereby useful for the treatment of disorders responsive to the modulation of the melanocortin-4 receptor, such as obesity, diabetes, male sexual dysfunction, female, sexual dysfunction, cachexia, anorexia, wasting, and weight loss.

BACKGROUND OF THE INVENTION

Obesity is a major health concern in Western societies. It is estimated that about 97 million adults in the United States are overweight or obese. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arteriosclerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," *Brain Research*, 80: 302-306 (1998)). Evidence for the involvement of MC-R's in obesity includes: i) the agouti (A$^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., *Cell*, 88: 131-141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Studies have shown that the melanocortin system contributes to the regulation of feeding behavior and bodyweight. Administration of melanocortin antagonists increases food intake and bodyweight, while administration of melanocortin agonists decreases food intake and bodyweight. Support for the role of the MC4R subtype in energy balance is demonstrated by evidence showing that the melanocortin-4 receptor deficiency in humans appears to be the most common monogenetic form of obesity with about 5-6% of obese patients showing this mutation. Furthermore, the severity of the phenotype appears to be greater in individuals that have mutations that result in complete loss of functioning. Based on these findings, the melanocortin system has been targeted for the development of small molecule agonists to treat obesity and small molecule antagonists to treat cachexia.

Weight loss drugs that are currently used in monotherapy for the treatment of obesity have limited efficacy and significant side effects. Studies of the weight loss medications orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5) have demonstrated a limited weight loss of about 5%-10% of body weight for drug compared to placebo. In particular, both sibutramine and orlistat reduce body weight less than 10% over a 6 month or a 1 year period. The side effects of these drugs and anti-obesity agents further limit their use. Dexfenfluramine was withdrawn from the market because of suspected heart valvulopathy; orlistat is limited by gastrointestinal side effects; the use of topiramate is limited by central nervous system effects; and the use of sibutramine is limited by its cardiovascular side effects which have led to reports of deaths and its withdrawal from the market in Italy.

There is a need for a weight loss treatment with enhanced efficacy and fewer undesirable side effects. The instant invention addresses this problem by providing melanocortin receptor (MC-R) agonists, and in particular selective agonists of the melanocortin-4 receptor (MC4R), useful in the treatment and prevention of obesity and obesity-related disorders, including diabetes.

Melanocortin receptor involvement in male and female sexual dysfunction has also been reported. Approximately 140 million men worldwide suffer from impotency or erectile dysfunction. Current treatment options for erectile dysfunction include phosphodiesterase V inhibitors, such as sildenafil citrate (Viagra®), vardenafil hydrochloride (Levitra®), and tadalafil (Cialis®). Sildenafil is effective in about 70% of patients, however it is contraindicated for patients with unstable heart conditions or cardiovascular disease, in particular patients taking nitrates, such as nitroglycerin, to treat angina. Vardenafil and Tadalafil are also contraindicated for patients taking nitrates and alpha blockers due to the risk of a sudden blood pressure drop resulting in fainting, heart attack or stroke. Other adverse effects associated with the clinical use of these PDE-5 inhibitors include headache, flushing, dyspepsia, dizziness, indigestion, and "abnormal vision, which is characterized by a bluish tinge to vision, but also an increased sensitivity to light or blurred vision. Sildenafil is also being evaluated for the treatment of female sexual dysfunction.

There is a need for a sexual dysfunction treatment with fewer undesirable side effects. The instant invention addresses this problem by providing melanocortin receptor (MC-R) agonists, and in particular selective agonists of the melanocortin-4 receptor (MC-4R), useful in the treatment and prevention of obesity and obesity-related disorders, including diabetes.

Synthetic melanocortin receptor agonists (melanotropic peptides) have been found to initiate erections in men with psychogenic erectile dysfunction. The centrally acting α-melanocyte-stimulating hormone analog, melanotan-II (MT-II), exhibited a 75% response rate when injected intramuscularly or subcutaneously into males with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389-393 (1998); *Fifteenth American Peptide Symposium*, Jun. 14-19, 1997 (Nashville Tenn.)]. MT-II (the cyclic heptapeptide Ac-Nle-c [Asp-His-DPhe-Arg-Trp-Lys]-NH$_2$) is a non-selective MC-1R, -3R, -4R, and -5R agonist (Dorr et al., *Life Sciences*, Vol. 58, 1777-1784, 1996). Adverse reactions observed with MT-II include nausea, flushing, loss of appetite, stretching, and yawning and may be the result of activation of MC-1R, MC-2R, MC-3R, and/or MC-5R. Additionally, MT-II must be administered parenterally, such as by subcutaneous, intravenous, or intramuscular route, since it is not absorbed into the systemic circulation when given by the oral route.

Compositions of melanotropic peptides and methods for the treatment of psychogenic erectile dysfunction are disclosed in U.S. Pat. No. 5,576,290. Methods of stimulating sexual response in females using melanotropic peptides have been disclosed in U.S. Pat. No. 6,051,555. Spiropiperidine, piperidine and piperazine derivatives have been disclosed in WO 99/64002; WO 00/74679; WO 01/70708; WO 01/70337; WO 01/91752; WO 02/015909; WO 02/059095; WO 02/059107; WO 02/059108; WO 02/059117; WO 02/068387; WO 02/068388; WO 02/079146; WO 03/061660, WO 03/007949; WO 03/009847; WO 03/009850; WO 03/068738; WO 03/092690; WO 03/093234; WO 03/094918; WO 04/024720; WO 04/048345; WO 04/058735; WO 04/078717; WO 04/112793; WO 04/224957; WO 04/089307; WO 04/078716; WO 04/078717; WO 04/087159; WO 05/042516; WO 05/040109; WO 05/009950; US2003096827; US2003092732; US2003232807, and US2004224901 as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated spiropiperidine derivatives which are melanocortin receptor agonists and thereby useful to treat obesity, diabetes, male sexual dysfunction, female sexual dysfunction, nicotine addiction and alcoholism. It is another object of the present invention to provide acylated spiropiperidine derivatives which are selective ligands of the melanocortin-4 (MC-4R) receptor. It is another object of the present invention to provide pharmaceutical compositions comprising the melanocortin receptor agonists or ligands of the present invention with a pharmaceutically acceptable carrier.

It is another object of the present invention to provide methods for the treatment or prevention of obesity, diabetes mellitus, male sexual dysfunction, female sexual dysfunction, nicotine addiction and alcoholism by administering the compounds and pharmaceutical compositions of the present invention to a subject in need thereof. It is another object of the present invention to provide methods for the treatment of erectile dysfunction by administering the compounds and pharmaceutical compositions of the present invention to a subject in need thereof.

It is another object of the present invention to provide methods for the treatment or prevention of disorders, diseases, or conditions responsive to the modulation of the melanocortin-4 receptor in a subject in need thereof by administering the compounds and pharmaceutical compositions of the present invention.

These and other objects will become readily apparent from the detailed description that follows.

SUMMARY OF THE INVENTION

The present invention relates to novel N-acylated spiropiperidines of structural formula I:

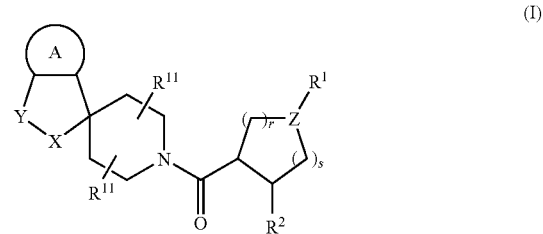

(I)

The compounds of structural formula I are effective as melanocortin receptor ligands and are particularly effective as selective ligands of the melanocortin-4 receptor. They are therefore useful for the treatment and/or prevention of disorders responsive to the modulation of the melanocortin-4 receptor, such as obesity, diabetes, obesity-related disorders, nicotine addiction, alcoholism, female sexual dysfunction, and male sexual dysfunction, in particular male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the modulation of the melanocortin-4 receptor in a mammal in need thereof by administering the compounds and pharmaceutical compositions of the present invention.

The present invention further relates to the use of the compounds of the present invention in the preparation of a medicament useful for the treatment or prevention of disorders, diseases, or conditions responsive to the modulation of the melanocortin-4 receptor in a mammal in need thereof by administering the compounds and pharmaceutical compositions of the present invention.

DETAILED DESCRIPTION OF THE INVENTION

The present invention relates to N-acylated spiropiperidine derivatives useful as melanocortin receptor modulators, in particular, as selective melanocortin-4 receptor ligands. Compounds of the present invention are described by structural formula I:

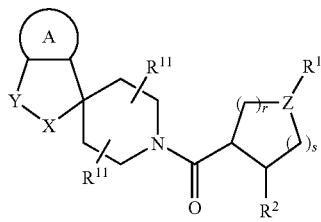

(I)

or a pharmaceutically acceptable salt thereof; wherein
A is a heteroaryl ring containing at least one heteroatom selected from nitrogen, oxygen and sulfur, wherein any carbon, nitrogen or sulfur in A is unsubstituted or substituted with one to two groups selected from $R^4$;
X and Y taken together form —C($R^6$)=C($R^6$)—, or
one of X and Y is C($R^6$)$_2$ and the other is selected from the group consisting of:
(1) C($R^6$)$_2$,
(2) N($R^6$),
(3) C(O),
(4) C=N($R^6$),
(5) C=C($R^6$)$_2$,
(6) oxygen,
(7) sulfur,
(8) S(O), and
(9) S(O)$_2$,
or one of X and Y is $NR^9$ and the other is selected from the group consisting of:
(1) C($R^6$)$_2$,
(2) C(O),
(3) C=N($R^6$),
(4) C=C($R^6$)$_2$,
(5) S(O), and
(6) S(O)$_2$,
or one of X and Y is C(O) and the other is selected from the group consisting of:
(1) C($R^6$)$_2$,
(2) N($R^6$),
(3) C=N($R^6$)
(4) oxygen, and
(5) sulfur;
Z is independently selected from the group consisting of:
(1) CH, and
(2) N,
provided that when Z is N, $R^1$ is not —$NR^7R^8$;
$R^1$ is selected from the group consisting of:
(1) hydrogen,
(2) —(CH$_2$)$_n$—$NR^7R^8$,
(3) amidino,
(4) C$_{1-4}$ alkyliminoyl,
(5) C$_{1-10}$alkyl,
(6) —(CH$_2$)$_n$—C$_{3-7}$ cycloalkyl, (7) —(CH$_2$)$_n$C$_{2-7}$heterocycloalkyl,
(8) —(CH$_2$)$_n$-phenyl,
(9) —(CH$_2$)$_n$-naphthyl,
(10) —(CH$_2$)$_n$-heteroaryl,
(11) —C(O)C$_{1-6}$alkyl,
(12) C(O)C$_{3-8}$cycloalkyl,
(13) C(O)C$_{2-7}$heterocycloalkyl,
(14) —C(O)heteroaryl,
(15) —C(O)phenyl, and
(16) —C(O)naphthyl,
wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo;
$R^2$ is selected from the group consisting of:
(1) phenyl,
(2) naphthyl, and
(3) heteroaryl,
wherein phenyl, naphthyl, and heteroaryl are unsubstituted or substituted with one to three groups independently selected from $R^{10}$;
each $R^3$ is independently selected from the group consisting of:
(1) C$_{1-6}$ alkyl,
(2) —(CH$_2$)$_n$-phenyl,
(3) —(CH$_2$)$_n$-naphthyl,
(4) —(CH$_2$)$_n$-heteroaryl,
(5) —(CH$_2$)$_n$C$_{2-7}$ heterocycloalkyl,
(6) —(CH$_2$)$_n$C$_{3-7}$ cycloalkyl,
(7) halogen,
(8) OR$^5$,
(9) —(CH$_2$)$_n$N(R$^5$)$_2$,
(10) —(CH$_2$)$_n$C≡N,
(11) —(CH$_2$)$_n$CO$_2$R$^5$,
(12) NO$_2$,
(13) —(CH$_2$)$_n$NR$^5$S(O)$_p$R$^5$,
(14) —(CH$_2$)$_n$S(O)$_p$N(R$^5$)$_2$,
(15) —(CH$_2$)$_n$S(O)$_p$R$^5$,
(16) —(CH$_2$)$_n$NR$^5$C(O)N(R$^5$)$_2$,
(17) —(CH$_2$)$_n$C(O)N(R$^5$)$_2$,
(18) —(CH$_2$)$_n$NR$^5$C(O)R$^5$,
(19) —(CH$_2$)$_n$NR$^5$CO$_2$R$^5$,
(20) —(CH$_2$)$_n$NR$^5$C(O)-heteroaryl,
(21) —(CH$_2$)$_n$C(O)NR$^5$N(R$^5$)$_2$,
(22) —(CH$_2$)$_n$C(O)NR$^5$NR$^5$C(O)R$^5$,
(23) O(CH$_2$)$_n$C(O)N(R$^5$)$_2$,
(24) CF$_3$,
(25) CH$_2$CF$_3$,
(26) OCF$_3$, and
(27) OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;
each $R^4$ is independently selected from the group consisting of:
(1) hydrogen,
(2) C$_{1-8}$ alkyl,
(3) —(CH$_2$)$_n$C$_{3-7}$ cycloalkyl,
(4) halogen, (5) $OR^5$,
(6) —$(CH_2)_nN(R^5)_2$,
(7) —$(CH_2)_nC\equiv N$,
(8) $CF_3$,
(9) $CH_2CF_3$,
(10) $OCF_3$, and
(11) $OCH_2CF_3$,
wherein alkyl, cycloalkyl, and ($CH_2$) are unsubstituted or substituted with one to three substituents independently selected from halogen, hydroxy, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;
each $R^5$ is independently selected from the group consisting of:
(1) hydrogen,
(2) $C_{1-8}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl, and
(8) —$(CH_2)_nC_{3-7}$ bicycloalkyl,
wherein alkyl, phenyl, heteroaryl, heterocycloalkyl, naphthyl, cycloalkyl, bicycloalkyl and ($CH_2$) are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;
each $R^6$ is independently selected from the group consisting of:
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$phenyl,
(6) —$(CH_2)_n$naphthyl,
(7) —$(CH_2)_n$heteroaryl,
(8) —$(CH_2)_nC(O)R^5$,
(9) —$(CH_2)_nC(O)OR^5$,
(10) —$(CH_2)_nC(OH)R^5$,
(11) —$(CH_2)_nC(O)N(R^5)_2$,
(12) —$(CH_2)_nC(O)N(R^5)N(R^5)C(O)R^5$,
(13) —$(CH_2)_n$—$OR^5$,
(14) —$(CH_2)_n$—$OC(O)R^5$,
(15) —$(CH_2)_n$—O—$(CH_2)_n$—$N(R^5)_2$,
(16) —$(CH_2)_n$CN,
(17) —$(CH_2)_nN(R^5)_2$,
(18) —$(CH_2)_nN(R^5)C(O)R^5$,
(19) —$(CH_2)_nN(C(O)R^5)_2$,
(20) —$(CH_2)_nN(R^5)C(O)OR^5$,
(21) —$(CH_2)_nN(C(O)OR^5)_2$,
(22) —$(CH_2)_nN(R^5)C(O)(CH_2)_nN(R^5)_2$,
(23) —$(CH_2)_nN(R^5)$—$S(O)$—$C_{1-8}$ alkyl,
(24) —$(CH_2)_nN(R^5)$—$S(O)_2$—$C_{1-8}$ alkyl,
(25) —$(CH_2)_n$—S—$R^5$,
(26) —$(CH_2)_n$—$S(O)$—$R^5$, and
(27) —$(CH_2)_n$—$S(O)_2$—$R^5$,
wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene carbon ($CH_2$) in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;
each $R^7$ and $R^8$ is independently selected from the group consisting of:
(1) hydrogen,
(2) $C_{1-6}$alkyl,
(3) $C_{3-7}$cycloalkyl,
(4) $C_{2-7}$heterocycloalkyl,
(5) phenyl,
(6) naphthyl, and
(7) heteroaryl,
wherein phenyl, naphthyl, and heteroaryl are unsubstituted or substituted with one to three groups independently selected from $R^3$, and wherein alkyl, cycloalkyl, and heterocycloalkyl are unsubstituted or substituted with one to three groups independently selected from $R^3$ and oxo;
each $R^9$ is independently selected from the group consisting of:
(1) hydrogen,
(2) $C_{1-6}$ alkyl,
(3) —$(CH_2)_nC_{3-7}$cycloalkyl,
(4) —$(CH_2)_nC_{2-7}$heterocycloalkyl,
(5) —$(CH_2)_n$-heteroaryl,
(6) —$(CH_2)_nC(O)OR^5$,
(7) —$(CH_2)_nC(O)(CH_2)_n$—$N(R^5)_2$,
(8) —$(CH_2)_nC(O)(CH_2)_n$—$NR^7R^8$,
(9) —$(CH_2)_m$—$OR^5$,
(10) —$(CH_2)_m$—$OC(O)R^5$,
(11) —$(CH_2)_m$—O—$(CH_2)_n$—$N(R^5)_2$, and
(12) —$(CH_2)_mN(R^5)_2$,
wherein heteroaryl is unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^9$ is unsubstituted or substituted with one to two groups independently selected from halogen, hydroxy, and $C_{1-4}$ alkyl; or wherein two $R^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;
each $R^{10}$ is independently selected from the group consisting of:
(1) hydrogen,
(2) $C_{1-6}$ alkyl,
(3) —$(CH_2)_n$-phenyl,
(4) —$(CH_2)_n$-naphthyl,
(5) —$(CH_2)_n$-heteroaryl,
(6) —$(CH_2)_nC_{2-7}$ heterocycloalkyl,
(7) —$(CH_2)_nC_{3-7}$ cycloalkyl,
(8) halogen,
(9) $OR^5$,
(10) —$(CH_2)_nN(R^5)_2$,
(11) —$(CH_2)_nC\equiv N$,
(12) —$(CH_2)_nCO_2R^5$,
(13) $NO_2$,
(14) —$(CH_2)_nNR^5S(O)_pR^5$,
(15) —$(CH_2)_nS(O)_pN(R^5)_2$,
(16) —$(CH_2)_nS(O)_pR^5$,

(17) —$(CH_2)_nNR^5C(O)N(R^5)_2$,
(18) —$(CH_2)_nC(O)N(R^5)_2$,
(19) —$(CH_2)_nNR^5C(O)R^5$,
(20) —$(CH_2)_nNR^5CO_2R^5$,
(21) —$(CH_2)_nNR^5C(O)$-heteroaryl,
(22) —$(CH_2)_nC(O)NR^5N(R^5)_2$,
(23) —$(CH_2)_nC(O)NR^5NR^5C(O)R^5$,
(24) $O(CH_2)_nC(O)N(R^5)_2$,
(25) $CF_3$,
(26) $CH_2CF_3$,
(27) $OCF_3$, and
(28) $OCH_2CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^{11}$ is independently selected from the group consisting of:
(1) hydrogen,
(2) —OH,
(3) $C_{1-8}$alkyl,
(4) —$OC_{1-8}$alkyl,
(5) halogen;
(6) —$NR^5$,
(7) —$SR^5$, and
(8) —$CF_3$, wherein two $C_{1-8}$alkyl substituents along with the atoms to which they are attached can form a 4- to 8-membered ring;
r is 1 or 2;
s is 1 or 2;
n is 0, 1, 2, or 3; and
p is 0, 1, or 2.

In a further embodiment of the compounds of the present invention, there are provided compounds of structural formula IIa or IIb of the indicated relative stereochemical configurations having the trans orientation of the $R^2$ and piperidinecarbonyl substituents:

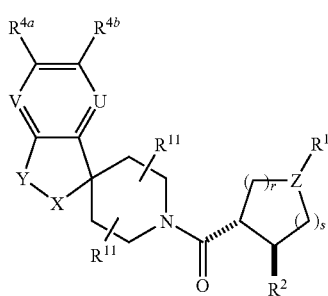

(IIa)

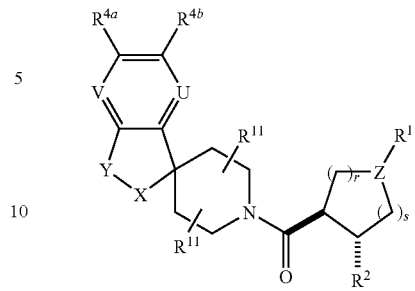

(IIb)

or a pharmaceutically acceptable salt thereof; wherein
U and V are independently selected from the group consisting of N and $CR^4$, and at least one of U and V is N;
X is selected from the group consisting of:
(1) $CH_2$,
(2) $CHC_{1-6}$alkyl,
(3) $NR^9$,
(4) oxygen, and
(5) sulfur;
Y is selected from the group consisting of:
(1) —$C(R^6)_2$,
(2) —$NR^6$,
(3) $C(O)$,
(4) $C=CH(R^6)$,
(5) $C=N(R^6)$,
(6) oxygen,
(7) sulfur,
(8) $S(O)$, and
(9) $S(O)_2$, provided that when Y is —$NR^6$, sulfur or oxygen, then X is not oxygen, sulfur, or —$NR^9$;
Z is independently selected from the group consisting of:
(1) CH, and
(2) N,
provided that when Z is N, $R^1$ is not —$NR^7R^8$;
$R^1$ is selected from the group consisting of:
(1) hydrogen,
(2) —$(CH_2)_n$—$NR^7R^8$,
(3) amidino,
(4) $C_{1-4}$ alkyliminoyl,
(5) $C_{1-10}$alkyl,
(6) —$(CH_2)_n$—$C_{3-7}$ cycloalkyl,
(7) —$(CH_2)_nC_{2-7}$heterocycloalkyl,
(8) —$(CH_2)_n$-phenyl,
(9) —$(CH_2)_n$-naphthyl,
(10) —$(CH_2)_n$-heteroaryl,
(11) —$C(O)C_{1-6}$alkyl,
(12) $C(O)C_{3-8}$cycloalkyl,
(13) $C(O)C_{2-7}$heterocycloalkyl,
(14) —$C(O)$heteroaryl,
(15) —$C(O)$phenyl, and
(16) —$C(O)$naphthyl, wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo;
$R^2$ is selected from the group consisting of:
(1) phenyl,
(2) naphthyl, and
(3) heteroaryl, wherein phenyl, naphthyl, and heteroaryl are unsubstituted or substituted with one to three groups independently selected from $R^{10}$;

$R^3$ is selected from the group consisting of:
(1) $C_{1-8}$ alkyl,
(2) —$(CH_2)_n$-phenyl,
(3) —$(CH_2)_n$-naphthyl,
(4) —$(CH_2)_n$-heteroaryl,
(5) —$(CH_2)_nC_{2-7}$ heterocycloalkyl,
(6) —$(CH_2)_nC_{3-7}$ cycloalkyl,
(7) halogen,
(8) $OR^5$,
(9) —$(CH_2)_nN(R^5)_2$,
(10) —$(CH_2)_nC\equiv N$,
(11) —$(CH_2)_nCO_2R^5$,
(12) —$(CH_2)_nOC(O)R^5$,
(13) $NO_2$,
(14) —$(CH_2)_nNR^5S(O)_pR^5$,
(15) —$(CH_2)_nN(S(O)_pR^5)_2$,
(16) —$(CH_2)_nS(O)_pN(R^5)_2$,
(17) —$(CH_2)_nS(O)_pR^5$,
(18) —$(CH_2)_nNR^5C(O)N(R^5)_2$,
(19) —$(CH_2)_nC(O)N(R^5)_2$,
(20) —$(CH_2)_nNR^5C(O)R^5$,
(21) —$(CH_2)_nNR^5CO_2R^5$,
(22) —$(CH_2)_nNR^5C(O)$-heteroaryl,
(23) —$(CH_2)_nC(O)NR^5N(R^5)_2$,
(24) —$(CH_2)_nC(O)NR^5NR^5C(O)R^5$,
(25) $O(CH_2)_nC(O)N(R^5)_2$,
(26) $CF_3$,
(27) $CH_2CF_3$,
(28) $OCF_3$, and
(29) $OCH_2CF_3$, wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

$R^{4a}$ and $R^{4b}$ are independently selected from the group consisting of:
(1) hydrogen,
(2) $C_{1-8}$ alkyl,
(3) —$(CH_2)_nC_{3-7}$ cycloalkyl,
(4) halogen,
(5) $OR^5$,
(6) —$(CH_2)_nN(R^5)_2$,
(7) —$(CH_2)_nC\equiv N$,
(8) $CF_3$,
(9) $CH_2CF_3$,
(10) $OCF_3$, and
(11) $OCH_2CF_3$, wherein alkyl, cycloalkyl, and ($CH_2$) are unsubstituted or substituted with one to three substituents independently selected from halogen, hydroxy, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^5$ is independently selected from the group consisting of:
(1) hydrogen,
(2) $C_{1-8}$ alkyl,
(3) —$(CH_2)_nC_{3-7}$ cycloalkyl,
(4) —$(CH_2)_nC_{2-7}$ heterocycloalkyl,
(5) —$(CH_2)_n$-phenyl,
(6) —$(CH_2)_n$-naphthyl,
(7) —$(CH_2)_n$-heteroaryl, and
(8) —$(CH_2)_nC_{3-7}$ bicycloalkyl;

wherein alkyl, phenyl, heteroaryl, heterocycloalkyl, naphthyl, cycloalkyl, bicycloalkyl and ($CH_2$) are unsubstituted or substituted with one to three groups independently selected from halogen, $C_{1-4}$ alkyl, hydroxy, and $C_{1-4}$ alkoxy, or wherein two $R^5$ groups together with the atom to which they are attached form a 4- to 8-membered mono- or bicyclic ring system optionally containing an additional heteroatom selected from O, S, and —$NC_{1-4}$ alkyl;

each $R^6$ is independently selected from the group consisting of:
(1) hydrogen,
(2) —$(CH_2)_nC_{2-7}$ heterocycloalkyl,
(3) $C_{1-6}$alkyl,
(4) —$(CH_2)_nC_{3-7}$cycloalkyl,
(5) —$(CH_2)_nC_{2-7}$heterocycloalkyl,
(6) —$(CH_2)_n$-phenyl,
(7) —$(CH_2)_n$-naphthyl,
(8) —$(CH_2)_n$-heteroaryl,
(9) —$(CH_2)_nC(O)R^5$,
(10) —$(CH_2)_nC(O)OR^5$,
(11) —$(CH_2)_nC(O)N(R^5)_2$,
(12) —$(CH_2)_nC(O)N(R^5)N(R^5)C(O)R^5$,
(13) —$(CH_2)_n$—$OR^5$,
(14) —$(CH_2)_n$—$OC(O)R^5$,
(15) —$(CH_2)_n$—O—$(CH_2)_n$—$N(R^5)_2$,
(16) —$(CH_2)_n$CN,
(17) —$(CH_2)_nN(R^5)_2$,
(18) —$(CH_2)_nN(R^5)C(O)R^5$,
(19) —$(CH_2)_nN(C(O)R^5)_2$,
(20) —$(CH_2)_nN(R^5)C(O)OR^5$,
(21) —$(CH_2)_nN(C(O)OR^5)_2$,
(22) —$(CH_2)_nN(R^5)C(O)(CH_2)_nN(R^5)_2$,
(23) —$(CH_2)_nN(R^5)$—$S(O)$—$C_{1-8}$ alkyl,
(24) —$(CH_2)_nN(R^5)$—$S(O)_2$—$C_{1-8}$ alkyl,
(25) —$(CH_2)_n$—S—$R^5$,
(26) —$(CH_2)_n$—$S(O)$—$R^5$, and
(27) —$(CH_2)_n$—$S(O)_2$—$R^5$, wherein phenyl, naphthyl, and heteroaryl are unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^6$ is unsubstituted or substituted with one to two groups independently selected from halogen, hydroxy, and $C_{1-4}$ alkyl, or wherein two $R^6$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^7$ and $R^8$ is independently selected from the group consisting of:
(1) hydrogen,
(2) $C_{1-6}$alkyl,
(3) $C_{3-7}$cycloalkyl,
(4) $C_{2-7}$heterocycloalkyl,
(5) phenyl,
(6) naphthyl, and
(7) heteroaryl, wherein phenyl, naphthyl, and heteroaryl are unsubstituted or substituted with one to three groups independently selected from $R^3$, and wherein alkyl, cycloalkyl, and heterocycloalkyl are unsubstituted or substituted with one to three groups independently selected from $R^3$ and oxo;

each $R^9$ is independently selected from the group consisting of:
(1) hydrogen,
(2) $C_{1-6}$ alkyl,
(3) —$(CH_2)_nC_{3-7}$ cycloalkyl,
(4) —$(CH_2)_nC_{2-7}$ heterocycloalkyl,
(5) —$(CH_2)_n$-heteroaryl,
(6) —$(CH_2)_nC(O)OR^5$,
(7) —$(CH_2)_nC(O)(CH_2)_n$—$N(R^5)_2$,
(8) —$(CH_2)_nC(O)(CH_2)_n$—$NR^7R^8$,
(9) —$(CH_2)_m$—$OR^5$,
(10) —$(CH_2)_m$—$OC(O)R^5$,
(11) —$(CH_2)_m$—O—$(CH_2)_n$—$N(R^5)_2$, and
(12) —$(CH_2)_mN(R^5)_2$, wherein heteroaryl is unsubstituted or substituted with one to three groups independently selected from $R^3$, and wherein alkyl, cycloalkyl and heterocycloalkyl are unsubstituted or substituted with one to three groups independently selected from $R^3$ and oxo, and wherein any methylene ($CH_2$) in $R^9$ is unsubstituted or substituted with one to two groups independently selected from halogen, hydroxy, and $C_{1-4}$ alkyl; or wherein two $R^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^{10}$ is independently selected from the group consisting of:
(1) hydrogen,
(2) $C_{1-6}$ alkyl,
(3) —$(CH_2)_n$-phenyl,
(4) —$(CH_2)_n$-naphthyl,
(5) —$(CH_2)_n$-heteroaryl,
(6) —$(CH_2)_nC_{2-7}$ heterocycloalkyl,
(7) —$(CH_2)_nC_{3-7}$ cycloalkyl,
(8) halogen,
(9) $OR^5$,
(10) —$(CH_2)_nN(R^5)_2$,
(11) —$(CH_2)_nC\equiv N$,
(12) —$(CH_2)_nCO_2R^5$,
(13) $NO_2$,
(14) —$(CH_2)_nNR^5S(O)_pR^5$
(15) —$(CH_2)_nS(O)_pN(R^5)_2$,
(16) —$(CH_2)_nS(O)_pR^5$,
(17) —$(CH_2)_nNR^5C(O)N(R^5)_2$,
(18) —$(CH_2)_nC(O)N(R^5)_2$,
(19) —$(CH_2)_nNR^5C(O)R^5$,
(20) —$(CH_2)_nNR^5CO_2R^5$,
(21) —$(CH_2)_nNR^5C(O)$-heteroaryl,
(22) —$(CH_2)_nC(O)NR^5N(R^5)_2$,
(23) —$(CH_2)_nC(O)NR^5NR^5C(O)R^5$,
(24) $O(CH_2)_nC(O)N(R^5)_2$,
(25) $CF_3$,
(26) $CH_2CF_3$,
(27) $OCF_3$, and
(28) $OCH_2CF_3$;

wherein phenyl, naphthyl, and heteroaryl are unsubstituted or substituted with one to three substituents independently selected from halogen, hydroxy, $C_{1-4}$ alkyl, trifluoromethyl, and $C_{1-4}$ alkoxy, and wherein alkyl, cycloalkyl, heterocycloalkyl, and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^{11}$ is independently selected from the group consisting of:
(1) hydrogen,
(2) —OH,
(3) $C_{1-8}$alkyl,
(4) —$OC_{1-8}$alkyl,
(5) halogen;
(6) —$NR^5$,
(7) —$SR^5$, and
(8) —$CF_3$, wherein two $C_{1-8}$alkyl substituents with the atom to which they are attached can form a 4- to 8-membered bicyclic ring system;

r is 1 or 2;
s is 1 or 2;
n is 0, 1, 2, or 3; and
p is 0, 1, or 2.

In yet a further embodiment of the compounds of the present invention, there are provided compounds of structural formula IIIa or IIIb of the indicated relative stereochemical configurations having the trans orientation of the phenyl and piperidinecarbonyl substituents:

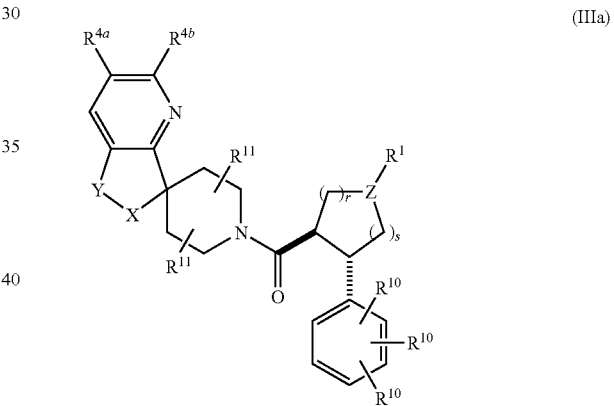

(IIIa)

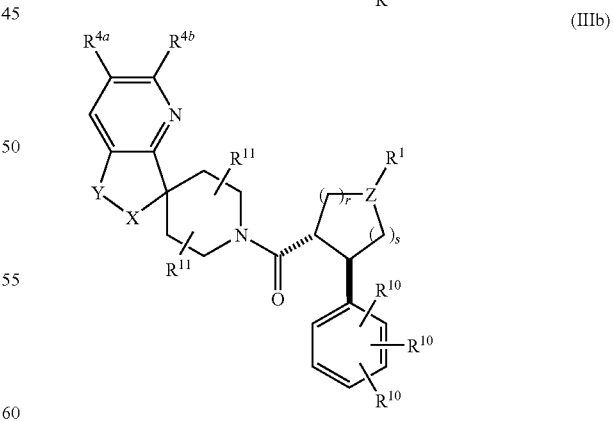

(IIIb)

or a pharmaceutically acceptable salt thereof; wherein
X is oxygen or $CH_2$;
Y is selected from the group consisting of:
(1) —$C(R^6)_2$,
(2) C=$CH(R^6)$, and
(3) —$NR^9$, provided that when X is oxygen, then Y is not —NR$^9$;
Z is independently selected from the group consisting of:
(1) CH, and
(2) N,
provided that when Z is N, R$^1$ is not —NR$^7$C$_{2-7}$heterocycloalkyl;
R$^1$ is selected from the group consisting of
(1) C$_{1-6}$alkyl,
(2) —N(R$^7$)C$_{2-7}$heterocycloalkyl,
(3) —(CH$_2$)$_n$C$_{2-7}$heterocycloalkyl,
(4) —C(O)C$_{1-6}$alkyl,
(5) —C(O)heteroaryl,
wherein heteroaryl is unsubstituted or substituted with one to three groups independently selected from R$^3$, and wherein alkyl and heterocycloalkyl are unsubstituted or substituted with one to three groups independently selected from R$^3$ and oxo;
R$^3$ is selected from the group consisting of:
(1) hydrogen,
(2) C$_{1-8}$ alkyl,
(3) —(CH$_2$)$_n$-phenyl,
(4) —(CH$_2$)$_n$-naphthyl,
(5) —(CH$_2$)$_n$-heteroaryl,
(6) —(CH$_2$)$_n$C$_{2-7}$ heterocycloalkyl,
(7) —(CH$_2$)$_n$C$_{3-7}$ cycloalkyl,
(8) halogen,
(9) OR$^5$,
(10) —(CH$_2$)$_n$N(R$^5$)$_2$,
(11) —(CH$_2$)$_n$C≡N,
(12) —(CH$_2$)$_n$C(O)OR$^5$,
(13) —(CH$_2$)$_n$OC(O)R$^5$,
(14) NO$_2$,
(15) —(CH$_2$)$_n$NR$^5$S(O)$_p$R$^5$,
(16) —(CH$_2$)$_n$N(S(O)$_p$R$^5$)$_2$,
(17) —(CH$_2$)$_n$S(O)$_p$N(R$^5$)$_2$,
(18) —(CH$_2$)$_n$S(O)$_p$R$^5$,
(19) —(CH$_2$)$_n$NR$^5$C(O)N(R$^5$)$_2$,
(20) —(CH$_2$)$_n$C(O)N(R$^5$)$_2$,
(21) —(CH$_2$)$_n$NR$^5$C(O)R$^5$,
(22) —(CH$_2$)$_n$NR$^5$CO$_2$R$^5$,
(23) —(CH$_2$)$_n$NR$^5$C(O)-heteroaryl,
(24) —(CH$_2$)$_n$C(O)NR$^5$N(R$^5$)$_2$,
(25) —(CH$_2$)$_n$C(O)NR$^5$NR$^5$C(O)R$^5$,
(26) O(CH$_2$)$_n$C(O)N(R$^5$)$_2$,
(27) CF$_3$,
(28) CH$_2$CF$_3$,
(29) OCF$_3$, and
(30) OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;
R$^{4a}$ and R$^{4b}$ are independently selected from the group consisting of:
(1) hydrogen,
(2) C$_{1-8}$ alkyl,
(3) halogen,
(4) CF$_3$,
wherein alkyl is unsubstituted or substituted with one to three substituents independently selected from halogen, hydroxy, C$_{1-4}$ alkyl, trifluoromethyl, and C$_{1-4}$ alkoxy;

each R$^5$ is independently selected from the group consisting of:
(1) hydrogen,
(2) C$_{1-8}$ alkyl,
(3) —(CH$_2$)$_n$C$_{3-7}$ cycloalkyl,
(4) —(CH$_2$)$_n$C$_{2-7}$ heterocycloalkyl,
(5) —(CH$_2$)$_n$-phenyl,
(6) —(CH$_2$)$_n$-naphthyl,
(7) —(CH$_2$)$_n$-heteroaryl, and
(8) —(CH$_2$)$_n$C$_{3-7}$ bicycloalkyl,
wherein alkyl, phenyl, heteroaryl, heterocycloalkyl, naphthyl, cycloalkyl, bicycloalkyl and (CH$_2$) are unsubstituted or substituted with one to three groups independently selected from halogen, C$_{1-4}$ alkyl, hydroxy, and C$_{1-4}$ alkoxy, or wherein two R$^5$ groups together with the atom to which they are attached form a 4- to 8-membered mono- or bicyclic ring system optionally containing an additional heteroatom selected from O, S, and —NC$_{1-4}$ alkyl;
each R$^6$ is independently selected from the group consisting of:
(1) hydrogen,
(2) —(CH$_2$)$_n$-heteroaryl,
(3) —(CH$_2$)$_n$C(O)N(R$^5$)$_2$,
(4) —(CH$_2$)$_n$C(O)N(R$^5$)N(R$^5$)C(O)R$^5$,
(5) —(CH$_2$)$_n$CN,
(6) —(CH$_2$)$_n$N(R$^5$)$_2$,
(7) —(CH$_2$)$_n$N(R$^5$)C(O)R$^5$,
wherein heteroaryl is unsubstituted or substituted with one to three groups independently selected from R$^3$, and wherein any methylene carbon (CH$_2$) in R$^6$ is unsubstituted or substituted with one to two groups independently selected from halogen, hydroxy, and C$_{1-4}$ alkyl;
each R$^7$ and R$^8$ is independently selected from the group consisting of:
(1) hydrogen,
(2) C$_{1-6}$alkyl,
(3) C$_{3-7}$cycloalkyl,
(4) C$_{2-7}$heterocycloalkyl,
(5) phenyl,
(6) naphthyl, and
(7) heteroaryl,
wherein phenyl, naphthyl, and heteroaryl are unsubstituted or substituted with one to three groups independently selected from R$^3$, and wherein alkyl, cycloalkyl, and heterocycloalkyl are unsubstituted or substituted with one to three groups independently selected from R$^3$ and oxo;
each R$^9$ is independently selected from the group consisting of:
(1) hydrogen,
(2) C$_{1-6}$ alkyl,
(3) —(CH$_2$)$_n$C$_{3-7}$ cycloalkyl,
(4) —(CH$_2$)$_n$C$_{2-7}$ heterocycloalkyl,
(5) —(CH$_2$)$_n$-heteroaryl,
(6) —(CH$_2$)$_n$C(O)OR$^5$,
(7) —(CH$_2$)$_n$C(O)(CH$_2$)$_n$—N(R$^5$)$_2$,
(8) —(CH$_2$)$_n$C(O)(CH$_2$)$_n$—NR$^7$R$^8$,
(9) —(CH$_2$)$_m$—OR$^5$,
(10) —(CH$_2$)$_m$—OC(O)R$^5$,
(11) —(CH$_2$)$_m$—O—(CH$_2$)$_n$—N(R$^5$)$_2$, and
(12) —(CH$_2$)$_m$N(R$^5$)$_2$,
wherein heteroaryl is unsubstituted or substituted with one to three groups independently selected from R$^3$, and wherein alkyl, cycloalkyl and heterocycloalkyl are unsubstituted or substituted with one to three groups independently selected from R$^3$ and oxo, and wherein any methylene (CH$_2$) in R$^9$ is unsubstituted or substituted with one to two groups independently selected from halogen, hydroxy, and C$_{1-4}$ alkyl; or wherein two $R^9$ groups together with the atoms to which they are attached form a 3- to 7-membered monocyclic ring optionally containing an additional heteroatom selected from O, S, and N, wherein the monocyclic ring is unsubstituted or substituted on carbon or nitrogen with one to three groups independently selected from $R^3$ and oxo;

each $R^{10}$ is independently selected from the group consisting of:
(1) hydrogen,
(2) $C_{1-6}$alkyl,
(3) $(CH_2)_n$phenyl,
(4) halogen,
(5) —$OR^5$,
(6) $(CH_2)_n$CN,
(7) $CF_3$,
(8) $CH_2CF_3$,
(9) $OCF_3$, and
(10) $OCH_2CF_3$,
wherein phenyl is unsubstituted or substituted with one to three substituents independently selected from halogen, hydroxy, $C_{1-4}$ alkyl, trifluoromethyl, and $C_{1-4}$ alkoxy, and wherein alkyl and ($CH_2$) are unsubstituted or substituted with one to three substituents independently selected from halogen, hydroxy, oxo, $C_{1-4}$ alkyl, trifluoromethyl, and $C_{1-4}$ alkoxy, or wherein two substituents when on the same methylene ($CH_2$) group are taken together with the carbon atom to which they are attached to form a cyclopropyl group;

each $R^{11}$ is independently selected from the group consisting of:
(1) hydrogen,
(2) —OH,
(3) $C_{1-8}$alkyl,
(4) —$OC_{1-8}$alkyl,
(5) halogen;
(6) —$NR^5$,
(7) —$SR^5$, and
(8) —$CF_3$,
wherein two $C_{1-8}$alkyl substituents along with the atoms to which they are attached can form a 4- to 8-membered ring;
r is 1 or 2;
s is 1 or 2;
n is 0, 1, 2, or 3; and
p is 0, 1, or 2.

In a class of the embodiments of the present invention, A is a heteroaryl ring selected from the group consisting of: pyridine, thiophene, furan, thiazole, pyrazole, pyrimidine, pyrazine and quinoline, wherein any carbon, nitrogen or sulfur in A is unsubstituted or substituted with one to two groups selected from $R^4$. In a subclass of this class, A is pyridine, wherein any carbon or nitrogen in A is unsubstituted or substituted with one to two groups selected from $R^4$.

In another class of the embodiments of the present invention, U and V are independently selected from the group consisting of: N, $CR^4$, $CR^{4a}$ and $CR^{4b}$, and at least one of U and V is N. In a subclass of this class, U is N; V is $CR^4$, $CR^{4a}$ and $CR^{4b}$. In another subclass of this class, V is N; U is $CR^4$, $CR^{4a}$ and $CR^{4b}$.

In another class of the embodiments of the present invention, X is independently selected from the group consisting of: oxygen, sulfur, $CH_2$, and $NR^9$. In a subclass of this class, X is oxygen. In another subclass of this class, X is $CH_2$. In another subclass of this class, X is sulfur. In another subclass of this class, X is $NR^9$.

In another class of the embodiments of the present invention, Y is selected from the group consisting of: $C(R^6)_2$ and $C=CHR^6$. In a subclass of this class, Y is $CHR^6$. In another subclass of this class, Y is $C=CHR^6$.

In another class of the embodiments of the present invention, X is oxygen or $CH_2$; and Y is selected from the group consisting of: —$C(R^6)_2$, —$C=CH(R^6)$, and —$NR^9$, provided that when X is oxygen, then Y is not —$NR^9$. In a subclass of this class, X is oxygen; and Y is selected from the group consisting of: —$C(R^6)_2$, —$C$—$CH(R^6)$.

In another class of the embodiments of the present invention, Z is CH. In a subclass of this class, Z is CH and $R^1$ is selected from the group consisting of: $C_{1-6}$alkyl optionally substituted with hydroxy, —$(CH_2)_n C_{2-9}$heterocycloalkyl and —$(CH_2)_n NR^7 C_{2-9}$heterocycloalkyl. In a subclass of this subclass, Z is CH and $R^1$ is selected from the group consisting of: tert-butyl, hydroxy tert-butyl, —$C_{2-9}$heterocycloalkyl and —$NR^7 C_{2-9}$heterocycloalkyl. In another subclass of this subclass, Z is CH and $R^1$ is selected from the group consisting of: tert-butyl, hydroxy tert-butyl, tetrahydropyran, pyrrolidine, morpholine and 4-methyl pyranylamine.

In another class of the embodiments of the present invention, Z is N. In a subclass of this class, Z is N and $R^1$ is selected from the group consisting of: —$C_{1-8}$alkyl, and —$(CH_2)_{0-1} C_{2-9}$heterocycloalkyl. In a subclass of this subclass, Z is N and $R^1$ is —$C_{2-9}$heterocycloalkyl. In another subclass of this subclass, Z is N and $R^1$ is tetrahydropyran, morpholine, and pyrrolidine. In another subclass of this class, Z is N and $R^1$ is —$NR^7 C_{2-9}$heterocycloalkyl. In another subclass of this class, Z is N and $R^1$ is $C_{1-8}$alkyl. In another subclass of this class, Z is N and $R^1$ is tert-butyl and hydroxy tert-butyl.

In another class of the embodiments of the present invention, $R^1$ is selected from the group consisting of $C_{1-8}$ alkyl, —$NR^7 R^8$, and $C_{2-7}$ heterocycloalkyl. In a subclass of this class, $R^1$ is $C_{1-8}$ alkyl unsubstituted or substituted with hydroxy. In another subclass of this class, $R^1$ is —$NR^7 R^8$. In a subclass of this subclass, $R^1$ is —$NR^7 C_{2-7}$heterocycloalkyl. In another subclass of this subclass, $R^1$ is tetrahydropyran, morpholine, and pyrrolidine. In another subclass of this class, $R^1$ is $C_{2-7}$ heterocycloalkyl unsubstituted or substituted on any carbon with 1-2 groups selected from: $C_{1-4}$alkyl and fluoro.

In another class of the embodiments of the present invention, $R^2$ is phenyl unsubstituted or substituted with one to three groups independently selected from $R^{10}$. In a subclass of this class, $R^2$ is phenyl substituted with one to three groups selected from $C_{1-4}$alkyl and halogen. In another subclass of this class, $R^2$ is phenyl substituted with one to three halogen groups. In another subclass of this class, $R^2$ is 2, 3, 4 trifluorophenyl. In another subclass of this class, $R^2$ is 2,4 difluorophenyl. In another subclass of this class, $R^2$ is 2-fluoro 4-chloro phenyl.

In another class of the embodiments of the present invention, $R^2$ is heteroaryl unsubstituted or substituted with one to three groups independently selected from $R^{10}$. In a subclass of this class, $R^2$ is a heteroaryl ring selected from the group consisting of: pyridine, thiophene, thiazole and pyrazine, unsubstituted or substituted with one to three groups independently selected from $R^3$. In a subclass of this subclass, $R^2$ is pyridine, unsubstituted or substituted with one to three groups independently selected from $R^3$. In another subclass of this class, $R^2$ is heteroaryl substituted with one to three groups selected from $C_{1-4}$alkyl and halogen. In another subclass of this class, $R^2$ is heteroaryl substituted with one to three halogen groups.

In another class of the embodiments of the present invention, $R^2$ is phenyl or pyridine, unsubstituted or substituted with one to three groups independently selected from $R^{10}$.

In another class of the embodiments of the present invention, $R^4$, $R^{4a}$ and $R^{4b}$ are selected from the group consisting of: hydrogen, $C_{1-6}$alkyl, halogen, and $CF_3$. In a subclass of this class, $R^4$ and $R^{4a}$ are selected from the group consisting of: hydrogen, $C_{1-6}$alkyl, and halogen. In a subclass of this subclass, $R^4$ and $R^{4a}$ are selected from the group consisting of: hydrogen, methyl, fluoro and chloro. In another subclass of this class, $R^4$ and $R^{4b}$ are selected from the group consisting of: hydrogen, $C_{1-6}$alkyl, halogen, and $CF_3$. In a subclass of this subclass, $R^4$ and $R^{4b}$ are selected from the group consisting of: hydrogen, methyl, and $CF_3$. In another subclass of this class, $R^{4a}$ is chloride and $R^{4b}$ is methyl. In another subclass of this class, $R^{4a}$ is methyl and $R^{4b}$ is hydrogen or methyl. In another subclass, $R^{4a}$ is fluoride and $R^{4b}$ is methyl. In another subclass of this class, $R^{4a}$ is hydrogen and $R^{4b}$ is $CF_3$.

In another class of the embodiments of the present invention, $R^6$ is selected from the group consisting of hydrogen, —$(CH_2)_n$CN, —$(CH_2)_n$heteroaryl, —$(CH_2)_n$C(O)N$(R^5)_2$, —$(CH_2)_n$N$(R^5)_2$, —$(CH_2)_n$C(O)N$(R^5)$N$(R^5)$C(O)$R^5$, and —$(CH_2)_n$N$(R^5)$C(O)$R^5$, wherein the carbon of each methylene $(CH_2)_n$ is unsubstituted or substituted with one or two $C_{1-4}$alkyl groups. In a subclass of this class, heteroaryl is selected from the group consisting of: tetrazole, triazole, pyrazole, thiazole, pyrimidine, pyrazine, pyridine, thiophene, furan, and oxadiazole. In a subclass of this subclass, heteroaryl is selected from the group consisting of: tetrazole, triazole, and oxadiazole. In another subclass of this class, $R^6$ is selected from the group consisting of hydrogen, —$(CH_2)_{0-1}$CN, —$(CH_2)_{0-1}$heteroaryl, —$(CH_2)$C(O)N$(R^5)_2$, —$(CH_2)$N$(R^5)_2$, —$(CH_2)$C(O)N$(R^5)$N$(R^5)$C(O)$R^5$, and —$(CH_2)$N$(R^5)$C(O)$R^5$, wherein the carbon of each methylene $(CH_2)_n$ is unsubstituted or substituted with one or two methyl groups. In a subclass of this subclass, $R^6$ is selected from the group consisting of hydrogen, —$(CH_2)_{0-1}$CN, —$(CH_2)$ n heteroaryl, —$(CH_2)_{0-1}$C(O)N$(R^5)_2$, and —$(CH_2)_{0-1}$N$(R^5)$C(O)$R^5$, wherein the carbon of each methylene $(CH_2)$ is unsubstituted, monosubstituted or disubstituted with methyl.

In another class of the embodiments of the present invention, $R^{10}$ is independently selected from the group consisting of: $C_{1-4}$alkyl, halogen, hydrogen and —$CF_3$. In a subclass of this class, $R^{10}$ is selected from the group consisting of hydrogen, methyl, fluoro, chloro and —$CF_3$ In a subclass of this class, $R^{10}$ is hydrogen, fluoro or chloro. In another subclass of this class, $R^{10}$ is hydrogen or fluoro.

In another class of the embodiments of the present invention, $R^{11}$ is independently selected from the group consisting of: $C_{1-6}$ alkyl, and hydrogen, wherein two $C_{1-6}$alkyl substituents along with the atoms to which they are attached can form a 4- to 8-membered ring. In a subclass of this class, $R^{11}$ methyl. In another subclass of this class, $R^{11}$ is hydrogen.

In another class of the embodiments of the present invention, r is 1 and s is 1. In another class of the embodiments of the present invention, r is 2 and s is 1.

In another class of the embodiments of the present invention, n is 0, 1, and 2. In a subclass of this class, p is 0. In another subclass of this class, p is 2.

In further embodiments of the compounds of structural formula I, there are provided compounds of structural formula IV, V, VI, VII, VIII and IX:

(IV)

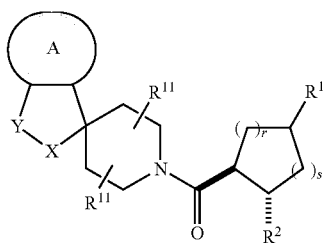

(V)

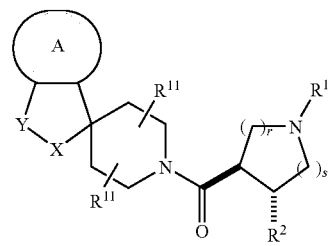

(VI)

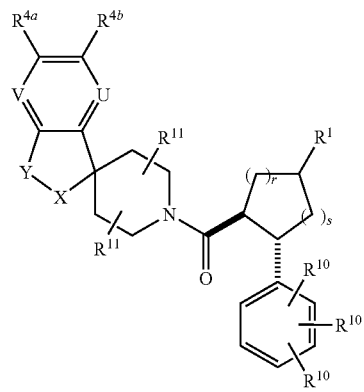

(VII)

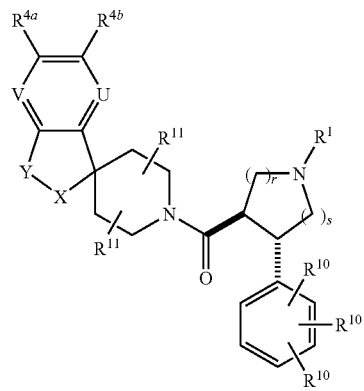

(VIII)

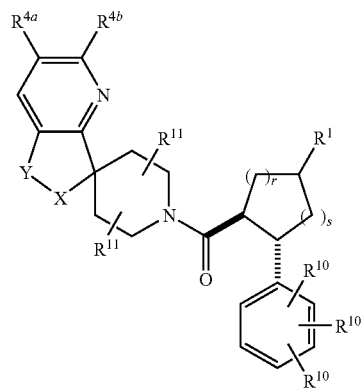

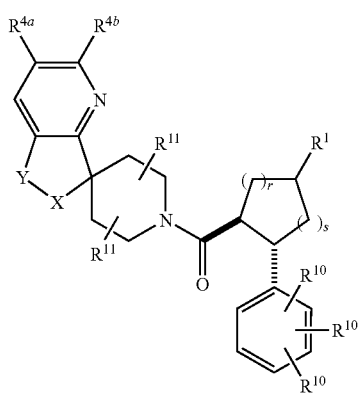
(IX)
Illustrative but nonlimiting examples of compounds of the present invention that are useful as melanocortin-4 receptor agonists are the following:
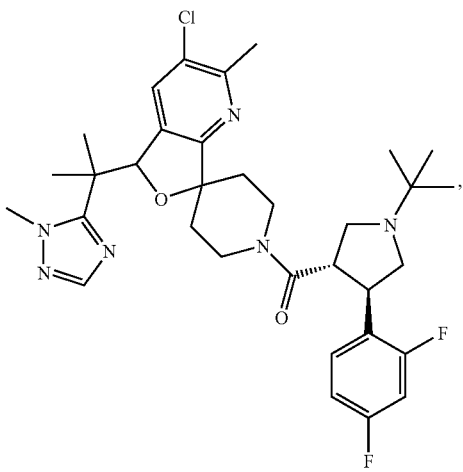
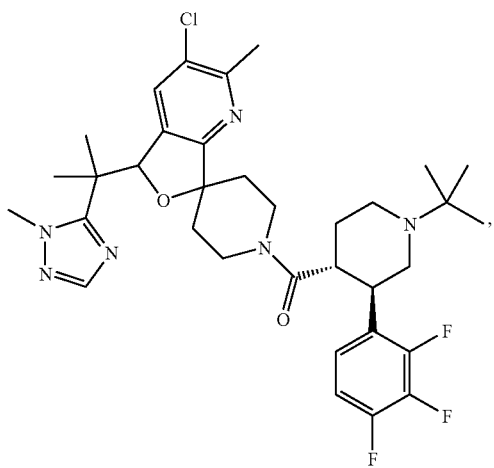
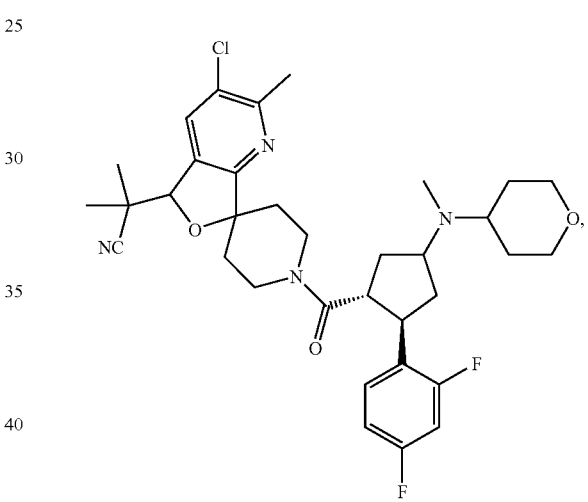
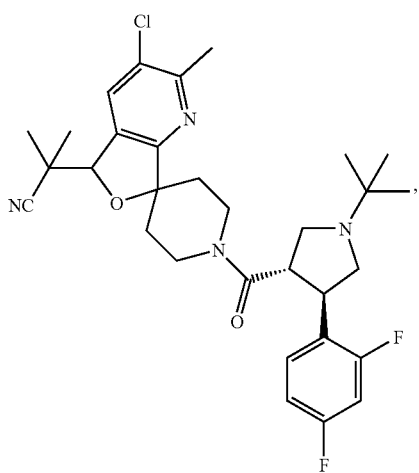
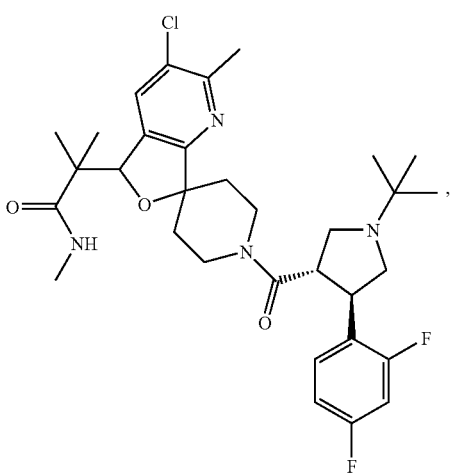

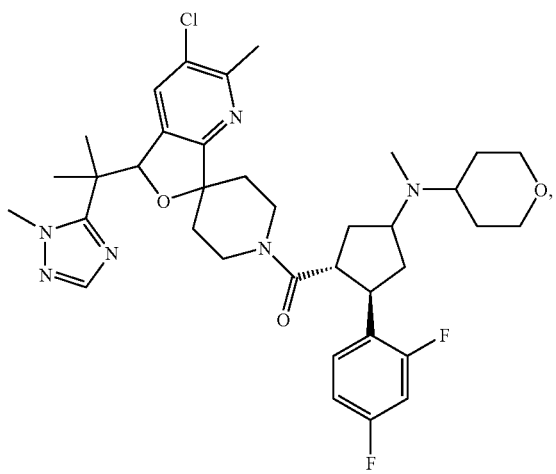
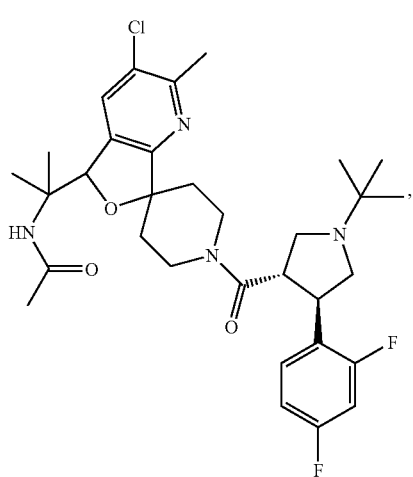
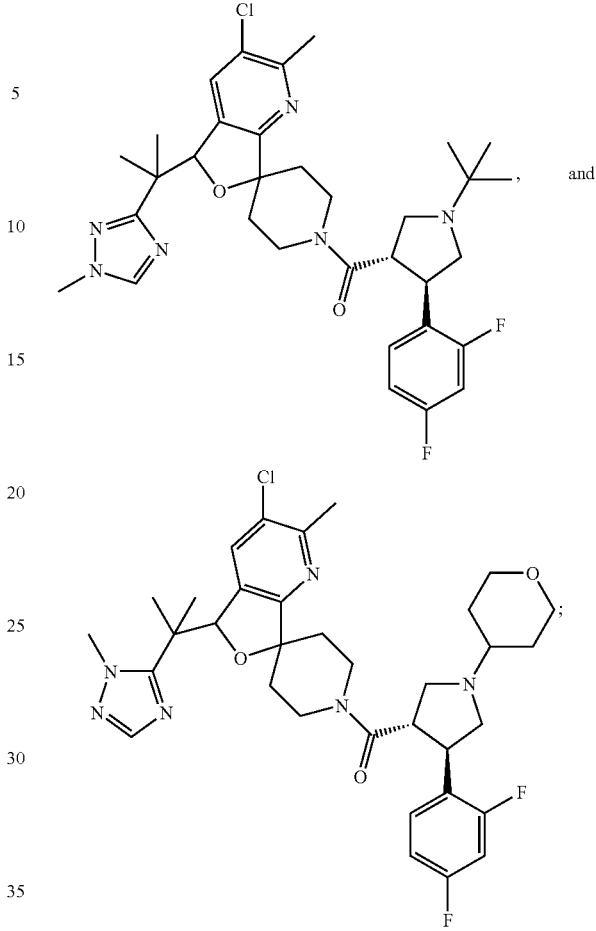

or a pharmaceutically acceptable salt thereof.

The compounds of structural formula I are effective as melanocortin receptor ligands and are particularly effective as selective ligands of the melanocortin-4 receptor. They are therefore useful for the treatment and/or prevention of disorders responsive to the modulation of the melanocortin-4 receptor, such as obesity, diabetes, obesity-related disorders, nicotine addiction, alcoholism, as well as male and female sexual dysfunction, and in particular male erectile dysfunction, cachexia, wasting, anorexia and weight loss.

More particularly, the selective melanocortin-4 receptor (MC-4R) agonists of formula I are useful for the treatment of disorders responsive to the activation of the melanocortin-4 receptor, such as obesity, diabetes, nicotine addiction, alcoholism, male sexual dysfunction, and female sexual dysfunction. Furthermore, the selective melanocortin-4 receptor (MC4R) antagonists of formula I are useful for the treatment of disorders responsive to the deactivation of the melanocortin-4 receptor, such as cachexia, wasting, anorexia, frailty, sarcopenia and weight loss.

Another aspect of the present invention provides a method for the treatment or prevention of obesity, diabetes, or an obesity related disorder in a subject in need thereof which comprises administering to said subject a therapeutically or prophylactically effective amount of a melanocortin 4 receptor agonist of the present invention. Another aspect of the present invention provides a method for the treatment or prevention of obesity in a subject in need thereof which comprises administering to the subject a therapeutically or prophylactically effective amount of a compound according to claim 1, or a pharmaceutically acceptable salt thereof. Another aspect of the present invention provides a method for the treatment or prevention of diabetes mellitus in a subject in need thereof comprising administering to the subject a therapeutically or prophylactically effective amount of a compound according to claim 1, or a pharmaceutically acceptable salt thereof. Another aspect of the present invention provides a method for the treatment or prevention of an obesity-related disorder selected from the group consisting of overeating, binge eating, and bulimia, hypertension, elevated plasma insulin concentrations, insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, metabolic syndrome, insulin resistance syndrome, sexual and reproductive dysfunction, infertility, hypogonadism, hirsutism, obesity-related gastro-esophageal reflux, Pickwickian syndrome, cardiovascular disorders, inflammation, systemic inflammation of the vasculature, arteriosclerosis, hypercholesterolemia, hyperuricaemia, lower back pain, gallbladder disease, gout, and kidney cancer, cardiac hypertrophy, left ventricular hypertrophy, nicotine addiction and alcoholism, in a subject in need thereof which comprises administering to the subject a therapeutically or prophylactically effective amount of a compound according to claim 1, or a pharmaceutically acceptable salt thereof.

The present invention also relates to methods for treating or preventing obesity by administering the melanocortin-4 receptor agonist of the present invention in combination with a therapeutically or prophylactically effective amount of another agent known to be useful to treat or prevent the condition. The present invention also relates to methods for treating or preventing diabetes by administering the melanocortin-4 receptor agonist of the present invention in combination with a therapeutically or prophylactically effective amount of another agent known to be useful to treat or prevent the condition.

Another aspect of the present invention provides a method for the treatment or prevention of female or male sexual dysfunction, including male erectile dysfunction, which comprises administering to a subject in need of such treatment or prevention a therapeutically or prophylactically effective amount of a melanocortin-4 receptor agonist of the present invention. Another aspect of the present invention provides a method for the treatment or prevention of erectile dysfunction in a subject in need thereof comprising administering to the subject a therapeutically or prophylactically effective amount of a compound according to claim 1, or a pharmaceutically acceptable salt thereof. The present invention also relates to methods for treating or preventing erectile dysfunction by administering the melanocortin-4 receptor agonist of the present invention in combination with a therapeutically or prophylactically effective amount of another agent known to be useful to treat the condition.

Another aspect of the present invention provides a method for the treatment or prevention of alcoholism which comprises administering to a subject in need of such treatment or prevention a therapeutically or prophylactically effective amount of a melanocortin 4 receptor agonist of the present invention. The present invention also provides a method for reducing alcohol consumption which comprises administering to a subject in need of such treatment or prevention a therapeutically or prophylactically effective amount of a melanocortin 4 receptor agonist of the present invention.

Another aspect of the present invention provides a method for the treatment or prevention of nicotine addiction which comprises administering to a subject in need of such treatment or prevention a therapeutically or prophylactically effective amount of a melanocortin 4 receptor agonist of the present invention. The present invention also provides a method for reducing nicotine consumption which comprises administering to a subject in need of such treatment a therapeutically effective amount of a melanocortin 4 receptor agonist of the present invention. Yet another aspect of the present invention provides a method for the treatment or prevention of substance addiction which comprises administering to a subject in need of such treatment or prevention a therapeutically or prophylactically effective amount of a melanocortin 4 receptor agonist of the present invention.

Yet another aspect of the present invention provides a method for the treatment or prevention of cachexia which comprises administering to a subject in need of such treatment or prevention a therapeutically or prophylactically effective amount of a melanocortin 4 receptor antagonist of the present invention. The present invention also provides a method for the treatment or prevention of anorexia, wasting or weight loss which comprises administering to a subject in need of such treatment or prevention a therapeutically or prophylactically effective amount of a melanocortin 4 receptor antagonist of the present invention.

Another aspect of the present invention provides a pharmaceutical composition comprising a compound of structural formula I and a pharmaceutically acceptable carrier.

Yet another aspect of the present invention relates to the use of a compound of structural formula I for the manufacture of a medicament useful for the treatment or prevention, or suppression of a disease mediated by the melanocortin-4 receptor in a subject in need thereof.

Yet another aspect of the present invention relates to the use of a melanocortin-4 agonist of the present invention for the manufacture of a medicament useful for the treatment or prevention, or suppression of a disease mediated by the melanocortin-4 receptor, wherein the disease is selected from the group consisting of obesity, diabetes and an obesity-related disorder in a subject in need thereof.

Yet another aspect of the present invention relates to the use of a melanocortin-4 agonist of the present invention for the manufacture of a medicament useful for the treatment or prevention, or suppression of male and female sexual dysfunction, and male erectile dysfunction in a subject in need thereof.

Yet another aspect of the present invention relates to the use of a selective melanocortin-4 agonist of the present invention in the preparation of a medicament useful for treating or preventing alcoholism in a subject in need thereof. The present invention also relates to the use of a selective melanocortin-4 agonist of the present invention in the preparation of a medicament useful for reducing alcohol consumption in a subject in need thereof.

Yet another aspect of the present invention relates to the use of a selective melanocortin 4 receptor agonist of the present invention in the preparation of a medicament useful to treat or prevent nicotine addiction in a subject in need thereof. The present invention also relates to the use of a selective melanocortin 4 receptor agonist of the present invention in the preparation of a medicament useful to reduce nicotine consumption in a subject in need thereof.

Yet another aspect of the present invention relates to the use of a selective melanocortin 4 receptor agonist of the present invention in the preparation of a medicament useful to treat substance addiction in a subject in need thereof.

Yet another aspect of the present invention relates to the use of a selective melanocortin 4 receptor antagonist of the present invention in the preparation of a medicament useful treat or prevent cachexia in a subject in need thereof. The present invention also relates to the use of a selective melanocortin 4 receptor antagonist of the present invention in the preparation of a medicament useful treat or prevent anorexia, wasting, frailty, sarcopenia, or weight loss in a subject in need thereof.

Yet another aspect of the present invention relates to the use of a therapeutically effective amount of a melanocortin-4 receptor agonist of formula I, or a pharmaceutically acceptable salt thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, and a NK-1 antagonist, or a pharmaceutically acceptable salt thereof, for the manufacture of a medicament useful for the treatment, control, or prevention of obesity, diabetes or an obesity-related disorder in a subject in need of such treatment. Yet another aspect of the present invention relates to the use of a therapeutically effective amount of a melanocortin-4 receptor agonist of formula I, and pharmaceutically acceptable salts and esters thereof, and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, and a NK-1 antagonist, or a pharmaceutically acceptable salt thereof, for the manufacture of a medicament for treatment or prevention of obesity, diabetes or an obesity-related disorder which comprises an effective amount of a melanocortin-4 receptor agonist of formula I and an effective amount of the agent, together or separately. Yet another aspect of the present invention relates to a product containing a therapeutically effective amount of a melanocortin-4 receptor agonist of formula I, or a pharmaceutically acceptable salt thereof; and a therapeutically effective amount of an agent selected from the group consisting of an insulin sensitizer, an insulin mimetic, a sulfonylurea, an α-glucosidase inhibitor, a HMG-CoA reductase inhibitor, a serotonergic agent, a β3-adrenoreceptor agonist, a neuropeptide Y1 antagonist, a neuropeptide Y2 agonist, a neuropeptide Y5 antagonist, a pancreatic lipase inhibitor, a cannabinoid $CB_1$ receptor antagonist or inverse agonist, a melanin-concentrating hormone receptor antagonist, a bombesin receptor subtype 3 agonist, a ghrelin receptor antagonist, and a NK-1 antagonist, or a pharmaceutically acceptable salt thereof, as a combined preparation for simultaneous, separate or sequential use in obesity, diabetes, or an obesity-related disorder.

Yet another aspect of the present invention relates to the use of a therapeutically effective amount of a melanocortin-4 receptor agonist of formula I, or a pharmaceutically acceptable salt thereof, and a therapeutically effective amount of an agent selected from the group consisting of: a type V cyclic-GMP-selective phosphodiesterase inhibitor, an $α_2$-adrenergic receptor antagonist, and a dopaminergic agent, or a pharmaceutically acceptable salt thereof, for the manufacture of a medicament useful for the treatment, control, or prevention of male erectile dysfunction in a subject in need of such treatment. Yet another aspect of the present invention relates to the use of a therapeutically effective amount of a melanocortin-4 receptor agonist of formula I, or a pharmaceutically acceptable salt thereof; and a therapeutically effective amount of an agent selected from the group consisting of a type V cyclic-GMP-selective phosphodiesterase inhibitor, an $α_2$-adrenergic receptor antagonist, and a dopaminergic agent, and pharmaceutically acceptable salts and esters thereof; for the manufacture of a medicament for treatment or prevention of male erectile dysfunction which comprises an effective amount of a compound of formula I and an effective amount of the agent, together or separately. Yet another aspect of the present invention relates to a product containing a therapeutically effective amount of a melanocortin-4 receptor agonist of formula I, or a pharmaceutically acceptable salt thereof; and a therapeutically effective amount of an agent selected from the group consisting of a type V cyclic-GMP-selective phosphodiesterase inhibitor, an $α_2$-adrenergic receptor antagonist, and a dopaminergic agent, and pharmaceutically acceptable salts and esters thereof, as a combined preparation for simultaneous, separate or sequential use in male erectile dysfunction.

Melanocortin receptor agonist compounds can be provided in kit. Such a kit typically contains an active compound in dosage forms for administration. A dosage form contains a sufficient amount of active compound such that a beneficial effect can be obtained when administered to a patient during regular intervals, such as 1, 2, 3, 4, 5 or 6 times a day, during the course of 1 or more days. Preferably, a kit contains instructions indicating the use of the dosage form for weight reduction (e.g., to treat obesity) and the amount of dosage form to be taken over a specified time period.

Throughout the instant application, the following terms have the indicated meanings:

The term "alkyl", as well as other groups having the prefix "alk", such as alkoxy, alkanoyl, means carbon chains of the designated length which may be in a straight or branched configuration, or combinations thereof. The term alkyl also includes methylene groups which are designated as ($CH_2$) herein. Examples of alkyl groups include methyl, ethyl, n-propyl, isopropyl, n-butyl, 1-methylpropyl, 2-methylpropyl, tert-butyl, n-pentyl, 1-methylbutyl, 2-methylbutyl, 3-methylbutyl, 1,2-dimethylpropyl, 1,1-dimethylpropyl, 2,2-dimethylpropyl, n-hexyl, 1-methylpentyl, 2-methylpentyl, 3-methylpentyl, 4-methylpentyl, 1-ethylbutyl, 2-ethylbutyl, 3-ethylbutyl, 1,1-dimethyl butyl, 1,2-dimethylbutyl, 1,3-dimethylbutyl, 2,2-dimethylbutyl, 2,3-dimethylbutyl, 3,3-dimethyl butyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, 4-ethylpentyl, 1-propylbutyl, 2-propylbutyl, 3-propylbutyl, 1,1-dimethylpentyl, 1,2-dimethylpentyl, 1,3-dimethylpentyl, 1,4-dimethylpentyl, 2,2-dimethylpentyl, 2,3-dimethylpentyl. 2,4-dimethylpentyl, 3,3-dimethylpentyl, 3,4-dimethylpentyl, 4,4-dimethylpentyl, 1-methyl-1-ethylbutyl, 1-methyl-2-ethylbutyl, 2-methyl-2-ethylbutyl, 1-ethyl-2-methylbutyl, 1-ethyl-3-methylbutyl, 1,1-diethylpropyl, n-octyl, n-nonyl, and the like.

The term "halogen" is intended to include the halogen atoms fluorine, chlorine, bromine and iodine.

The term "$C_{1-4}$ alkyliminoyl" means $C_{1-3}$alkylC(=NH)—.

The term "aryl" includes phenyl and naphthyl.

The term "heteroaryl" includes mono- and bicyclic aromatic rings containing from 1 to 4 heteroatoms selected from nitrogen, oxygen and sulfur. Examples thereof include, but are not limited to, pyridinyl, furyl, thienyl, pyrrolyl, oxazolyl, thiazolyl, triazolyl, triazinyl, tetrazolyl, thiadiazolyl, imidazolyl, isoxazolyl, isothiazolyl, oxadiazolyl, pyrazolyl, pyrimidinyl, pyrazinyl, pyridazinyl, quinolyl, isoquinolyl, benzimidazolyl, benzofuryl, benzothienyl, indolyl, benzthiazolyl, benzoxazolyl, and the like. In one embodiment of the present invention, heteroaryl is selected from the group consisting of pyridinyl, furyl, thienyl, pyrrolyl, oxazolyl, thiazolyl, triazolyl, triazinyl, tetrazolyl, thiadiazolyl, imidazolyl, pyrazolyl, isoxazolyl, isothiazolyl, oxathiazolyl, pyrimidinyl, pyrazinyl, pyridazinyl, quinolyl, isoquinolyl, benzimidazolyl, benzofuryl, benzothienyl, indolyl, benzthiazolyl, and benzoxazolyl.

Bicyclic heteroaromatic rings include, but are not limited to, benzothiadiazole, indole, benzothiophene, benzofuran, benzimidazole, benzisoxazole, benzothiazole, quinoline, quinazoline, benzotriazole, benzoxazole, isoquinoline, purine, furopyridine, thienopyridine, benzisodiazole, triazolopyrimidine, and 5,6,7,8-tetrahydroquinoline.

The term "cycloalkyl" includes mono- or bicyclic non-aromatic rings containing only carbon atoms. Examples of cycloalkyl include, but are not limited to, cyclopropyl, cyclobutyl, cyclopentyl, cyclohexyl, cycloheptyl.

The term "heterocycloalkyl" includes two to eight carbon mono- or bicyclic non-aromatic heterocyclic rings containing one to four heteroatoms selected from nitrogen, oxygen, sulfur, sulfone, and sulfoxide. Substitution on the heterocycloalkyl ring includes optional mono- or di-substitution on any carbon and/or optional monosubstitution on any nitrogen and sulfur of the heterocycloalkyl ring with a substituent from $R^3$. Examples of heterocycloalkyls include, but are not limited to, azetidine, piperidine, pyrrolidine, morpholine, thiamorpholine, tetrahydropyran, thiatetrahydropyran, imidazolidine, tetrahydrofuran, piperazine, 1-thia-4-azacyclohexane, (1R,4R)-2-oxa-5-azabicyclo[2.2.1]hept5-yl, and 4 tetrahydropyran.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

The term "subject" means a mammal. One embodiment of the term "mammal" is a "human," said human being either male or female. The instant compounds are also useful for treating or preventing obesity and obesity related disorders in cats and dogs. As such, the term "mammal" includes companion animals such as cats and dogs. The term "mammal in need thereof" refers to a mammal who is in need of treatment or prophylaxis as determined by a researcher, veterinarian, medical doctor or other clinician.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

By a melanocortin receptor "agonist" is meant an endogenous or drug substance or compound that can interact with a melanocortin receptor and initiate a pharmacological or biochemical response characteristic of melanocortin receptor activation. By a melanocortin receptor "antagonist" is meant a drug or a compound that inhibits the melanocortin receptor-associated responses induced by an agonist. The "agonistic" and "antagonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity of response which different agonists produce even when they occupy the same number of receptors and with the same affinity. Efficacy is the property that describes the magnitude of response. Properties of compounds can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I, including the E and Z geometric isomers of olefinic double bonds. Some of the compounds described herein may exist as tautomers such as keto-enol tautomers. The individual tautomers as well as mixtures thereof are encompassed within the compounds of structural formula I.

The compound of formula X encompasses the diastereomers Xa and Xb:

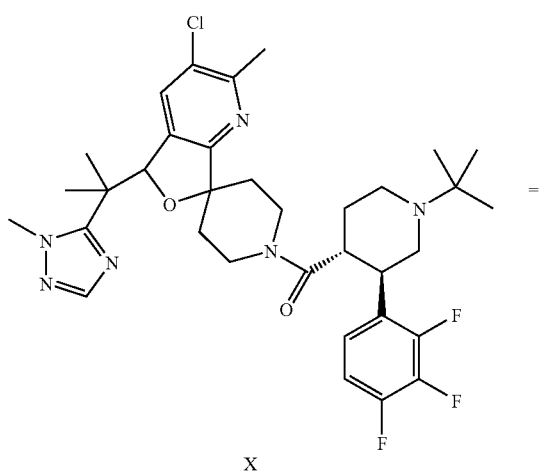

X

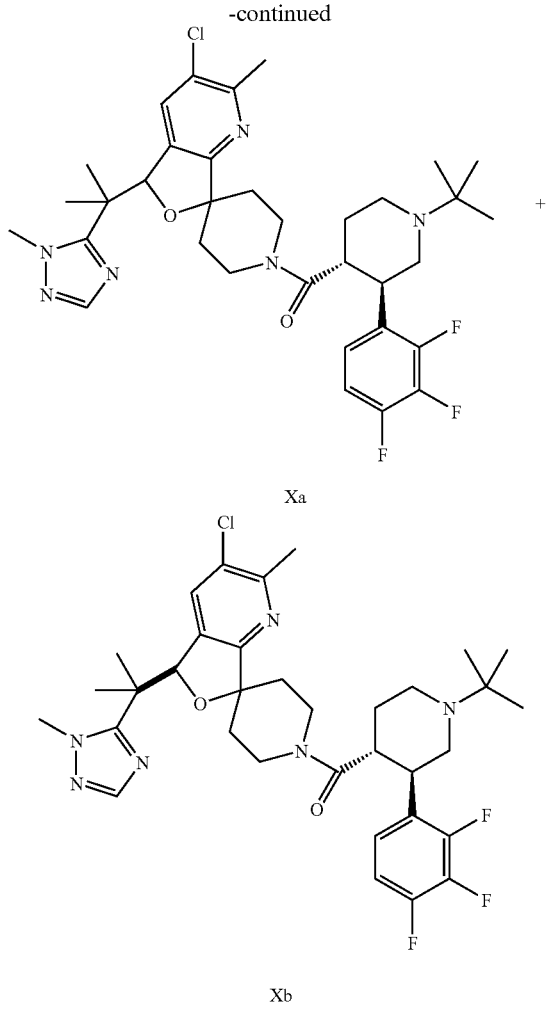

Xa

Xb

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, IIa, IIb, IIIa, IIIb, IV, V, VI, VII, VIII and IX may be obtained by stereospecific synthesis using optically pure starting materials or reagents of known absolute configuration.

It will be understood that the compounds of the present invention include hydrates, solvates, polymorphs, crystalline, hydrated crystalline and amorphous forms of the compounds of the present invention, and pharmaceutically acceptable salts thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts, such as the hydrochloride salts.

Compounds of formula I are melanocortin receptor ligands and as such are useful in the treatment, control or prevention of diseases, disorders or conditions responsive to the modulation of one or more of the melanocortin receptors including, but are not limited to, MC-1, MC-2, MC-3, MC-4, or MC-5. In particular, the compounds of formula I act as melanocortin-4 receptor agonists and antagonists useful in the treatment, control or prevention of diseases, disorders or conditions responsive to the activation or deactivation of the melanocortin-4 receptor. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including male impotence, loss of libido, female sexual arousal dysfunction, female orgasmic dysfunction, hypoactive sexual desire disorder, sexual pain disorder and male erectile dysfunction), fever, inflammation, immunemodulation, rheumatoid arthritis, skin tanning, acne and other skin disorders, neuroprotective and cognitive and memory enhancement including the treatment of Alzheimer's disease. Some agonists encompassed by formula I show highly selective affinity for the melanocortin-4 receptor (MC-4R) relative to MC-1R, MC-2R, MC-3R, and MC-5R, which makes them especially useful in the prevention and treatment of obesity, female sexual dysfunction, male sexual dysfunction including erectile dysfunction, alcoholism and nicotine addiction. Some antagonists encompassed by formula I show highly selective affinity for the melanocortin-4 receptor (MC-4R) relative to MC-1R, MC-2R, MC-3R, and MC-5R, which makes them especially useful in the prevention and treatment of cachexia, wasting and anorexia.

The compositions of the present invention are useful for the treatment or prevention of disorders associated with excessive food intake, such as obesity and obesity-related disorders. The obesity herein may be due to any cause, whether genetic or environmental.

The obesity-related disorders herein are associated with, caused by, or result from obesity. Examples of obesity-related disorders include overeating, binge eating, and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer, nicotine addiction, substance addiction and alcoholism. The compositions of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "diabetes," as used herein, includes both insulin-dependent diabetes mellitus (i.e., IDDM, also known as type I diabetes) and non-insulin-dependent diabetes mellitus (i.e., NIDDM, also known as Type I diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compositions of the present invention are useful for treating both Type I and Type II diabetes. The compositions are especially effective for treating Type II diabetes. The compounds or combinations of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be improving glycemic control. Another outcome of treatment may be decreasing insulin levels in a subject with elevated insulin levels. Another outcome of treatment may be decreasing plasma triglycerides in a subject with elevated plasma triglycerides. Another outcome of treatment may be lowering LDL cholesterol in a subject with high LDL cholesterol levels. Another outcome of treatment may be increasing HDL cholesterol in a subject with low HDL cholesterol levels. Another outcome may be decreasing the LDL/HDL ratio in a subject in need thereof. Another outcome of treatment may be increasing insulin sensivity. Another outcome of treatment may be enhancing glucose tolerance in a subject with glucose intolerance. Another outcome of treatment may be decreasing insulin resistance in a subject with increased insulin resistance or elevated levels of insulin. Another outcome may be decreading triglycerides in a subject with elevated triglycerides. Yet another outcome may be improving LDL cholesterol, non-HDL cholesterol, triglyceride, HDL cholesterol or other lipid analyte profiles.

Prevention of diabetes mellitus refers to the administration of a compound or combination of the present invention to prevent the onset of diabetes in a subject at risk thereof.

"Obesity" is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 $kg/m^2$. In Asian countries, including Japan, an "obese subject" refers to a subject with at least one obesity-induced or obesity-related co-morbidity that requires weight reduction or that would be improved by weight reduction, with a BMI greater than or equal to 25 $kg/m^2$. In Asia-Pacific, a "subject at risk of obesity" is a subject with a BMI of greater than 23 $kg/m^2$ to less than 25 $kg/m^2$.

As used herein, the term "obesity" is meant to encompass all of the above definitions of obesity.

Obesity-induced or obesity-related co-morbidities include, but are not limited to, diabetes, non-insulin dependent diabetes mellitus-type II (2), impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in subjects in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis.

"Male sexual dysfunction" includes impotence, loss of libido, and erectile dysfunction.

"Erectile dysfunction" is a disorder involving the failure of a male subject to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

Treatment of male sexual dysfunction refers to the administration of a compound or combination of the present invention to treat impotence and/or loss of libido, and/or erectile dysfunction in a male subject in need thereof. One outcome of treatment may be a decrease in impotence. Another outcome of treatment may be an increase in libido. Yet another outcome of treatment may be a decrease in the magnitude or frequency of erectile dysfunction. Treatment of male erectile dysfunction refers to the administration of a compound or combination of the present invention to treat one or more of the symptoms of male erectile dysfunction in a male subject in need thereof. One outcome of treatment may be increasing the ability to achieve an erection. Another outcome of treatment may be increasing the ability to maintain an erection. Another outcome of treatment may be reducing ejaculatory failure. Another outcome of treatment may be decreasing premature ejaculation. Yet another outcome of treatment may be increasing the ability to achieve an orgasm. Prevention of male sexual dysfunction and male erectile dysfunction refers to the administration of the compounds or combinations of the present invention to prevent the symptoms of sexual dysfunction and erectile dysfunction in a male subject at risk thereof.

"Female sexual dysfunction" can be seen as resulting from multiple components including dysfunction in desire, sexual arousal, sexual receptivity, and orgasm related to disturbances in the clitoris, vagina, periurethral glands, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

The compositions of the present invention are useful for the treatment or prevention of disorders associated with excessive food intake, such as obesity and obesity-related disorders.

"Cachexia" is a wasting disorder that is characterized by weight loss, loss of muscle protein, loss of lean body mass, anorexia, and weakness, and is typically associated with chronic diseases, including cancer cachexia and cachexia associated with AIDS, chronic obstructive pulmonary disease, rheumatoid arthritis, tuberculosis and Crohn's disease. Cancer cachexia is a syndrome of progressive weight loss, anorexia, and persistent erosion of the body in response to a malignant growth; cachexia may be present in early stages of tumor growth before any signs or symptoms of malignancy.

Treatment of cachexia refers to the administration of a compound or combination of the present invention to treat one or more of the symptoms of cachexia in a subject in need thereof.

Prevention of cachexia refers to the administration of the compounds or combinations of the present invention to prevent the symptoms of cachexia or wasting in a subject at risk thereof, including but not limited to, a subject diagnosed with cancer.

The compositions of the present invention are useful for the treatment or prevention of nicotine addiction, substance addiction, and alcoholism, as well as nicotine addiction related disorders, substance abuse related disorders, and alcoholism related disorders.

The term "nicotine" as used herein refers to nicotine contained in tobacco and other naturally occurring sources, as well as synthetic nicotine, and salts thereof, including but not limited to, the salicylate or bitartrate salt thereof. Nicotine addiction is a destructive pattern of nicotine use, leading to significant social occupational, or medical impairment and characterized by three or more of the following symptoms: 1) nicotine tolerance (a need for markedly increased amounts of nicotine to achieve intoxication, or markedly diminished effect with continued use of the same amount of nicotine); 2) nicotine withdrawal symptoms (sweating or rapid pulse, increased hand tremor, insomnia, nausea or vomiting, physical agitation, anxiety, transient visual, tactile, or auditory hallucinations or illusions, grand mal seizures), 3) nicotine administration to relieve or avoid withdrawal symptoms, 4) greater use than nicotine than intended, 5) unsuccessful efforts to cut down or control nicotine use, 6) persistent desire or unsuccessful efforts to cut down or control nicotine use, 7) great deal of time spent using nicotine, 8) nicotine caused reduction in social, occupational or recreational activities, and 9) continued use of nicotine despite knowledge of having a persistent or recurrent physical or psychological problem that is likely to have been worsened by nicotine use. Nicotine addiction-related disorders include, but are not limited to: cancer of the lung, mouth, pharynx, larynx, esophagus, cervix, kidney, ureter and bladder; chronic bronchitis; emphysema; asthma; heart disease, including stroke, heart attack, vascular disease, and aneurysm; premature delivery; spontaneous abortion; and infants with decreased birth weight; as well as nicotine withdrawal symptoms. "Treatment" (of nicotine addiction) refers to the administration of the compounds or combinations of the present invention to reduce or inhibit the use of nicotine by a subject. One outcome of treatment may be reducing the use of nicotine in a subject relative to the subject's nicotine use prior to treatment. Another outcome of treatment may be inhibiting the use of nicotine in a subject. Another outcome of treatment may be decreasing the severity of nicotine intake, such as decreasing the amount of nicotine consumed, in a subject. "Prevention" (of nicotine addiction) refers to the administration of the compounds or combinations of the present invention to prevent nicotine abuse, nicotine addiction or developing a nicotine addiction-related disorder in a subject by administration prior to the start of nicotine use. One outcome of prevention may be to prevent nicotine use in a subject by administration prior to the start of nicotine use. Another outcome of prevention may be to prevent nicotine addiction in a subject. Another outcome of prevention may be to prevent the development of a nicotine addiction related disorder in a subject. Another outcome of prevention may be preventing nicotine use from occurring if the treatment is administered prior to the onset of nicotine use in a subject. Another outcome of prevention may be to administer the compounds or combinations of the present invention to prevent nicotine use in a subject at risk of developing nicotine addiction.

Substance addiction includes opiate addiction, cocaine addiction, marijuana addiction, and amphetamine addiction. The term "opiate" as used herein includes, but is not limited to, heroin; narcotics, such as morphine; opium; codeine; oxycodone (Oxycontin®); propoxyphene (Darvon®); hydrocodone (Vicodin®), hydromorphone (Dilaudid®); meperidine (Demerol®), and Lomotil®. The term "amphetamine(s)" as used herein includes, but is not limited to, amphetamine, dextroamphetamine, and methamphetamine. "Treatment" (of substance addiction) refers to the administration of the compounds or combinations of the present invention to reduce or inhibit the use of the substance by a subject. One outcome of treatment may be reducing the use of the substance in a subject relative to the subject's substance use prior to treatment. Another outcome of treatment may be inhibiting the use of the substance in a subject. Another outcome of treatment may be decreasing the occurrence of substance intake in a subject. Another outcome of treatment may be decreasing the severity of substance intake, such as decreasing the amount of the substance consumed, in a subject. Another outcome of treatment may be to administer the compounds or combinations of the present invention to reduce or inhibit the consumption of the substance in a subject in need thereof. "Prevention" (of substance addiction) refers to the administration of the compounds or combinations of the present invention to prevent substance addiction or developing a substance addiction-related disorder in a subject. One outcome of prevention may be to prevent substance use in a subject by administration prior to the start of substance use. Another outcome of prevention may be to prevent substance addiction in a subject. Another outcome of prevention may be to prevent the development of a substance addiction related disorder in a subject. Another outcome of prevention may be preventing substance use from occurring if the treatment is administered prior to the onset of substance use in a subject.

The compounds of the present invention are useful to inhibit or reduce voluntary alcohol consumption, and for the treatment or prevention of alcoholism, alcohol abuse, and alcohol-related disorders. Alcoholism is a disease that is characterized by abnormal alcohol seeking behavior that leads to impaired control over drinking, and may include some or all of the following symptoms: narrowing of drinking repertoire (drinking only one brand or type of alcoholic beverage); craving (a strong need or urge to drink), loss of control (not being able to stop drinking once drinking has begun), drink seeking behavior (attending only social events that include drinking); physical dependence (withdrawal symptoms, such as nausea, sweating, shakiness, and anxiety after cessation of drinking), drinking to relieve or avoid withdrawal symptoms; and tolerance (the need to drink greater amounts of alcohol to achieve previous effects); subjective awareness of the compulsion to drink or craving for alcohol; and relapse (a return to drinking after a period of abstinence). Alcohol related disorders include, but are not limited to: liver disease, such as hepatitis, inflammation of the liver, and alcoholic cirrhosis; heart disease; high blood pressure; stroke; certain forms of cancer, such as esophageal, mouth, throat, voice box, breast, colon and rectal cancer; pancreatitis; alcoholic dementia, Wernicke-Korsakoff syndrome, brain damage, slow bone healing; impaired wound healing; diminished immune defenses; and death. "Treatment" (of alcoholism) refers to the administration of the compounds or combinations of the present invention to reduce or inhibit the consumption of alcohol in a subject. One outcome of treatment may be reducing the consumption of alcohol in a subject relative to the subject's alcohol consumption prior to treatment. Another outcome of treatment may be inhibiting consumption of alcohol in a subject. Another outcome of treatment may be decreasing the occurrence of alcohol intake in a subject. Another outcome of treatment may be decreasing the severity of alcohol intake, such as decreasing the amount of alcohol consumed, in a subject. Another outcome of treatment may be to administer the compounds or combinations of the present invention to reduce or inhibit the consumption of alcohol in a subject in need thereof. "Prevention" (of alcoholism) refers to the administration of the compounds or combinations of the present invention to prevent alcohol intake, alcohol consumption, alcohol abuse, alcoholism or developing an alcohol-related disorder in a subject. One outcome of prevention may be to prevent alcohol intake in a subject by administration prior to the start of alcohol consumption. Another outcome of prevention may be to prevent alcoholism in a subject. Another outcome of prevention may be to administer the compounds or combinations of the present invention to prevent alcohol intake in a subject at risk of alcoholism or developing an alcohol-related disorder in a subject. Moreover, if treatment is commenced in a subject already consuming alcohol, such treatment may prevent the occurrence, progression or severity of alcohol-related disorders.

The terms "administration of" and or "administering" a compound should be understood to mean providing a compound of the invention or a prodrug of a compound of the invention to a subject in need of treatment. The administration of the compounds of the present invention in order to practice the present methods of therapy is carried out by administering a therapeutically effective amount of the compound to a subject in need of such treatment or prophylaxis. The need for a prophylactic administration according to the methods of the present invention is determined via the use of well known risk factors.

The term "therapeutically effective amount" as used herein means the amount of the active compound that will elicit the biological or medical response in a tissue, system, subject, mammal, or human that is being sought by the researcher, veterinarian, medical doctor or other clinician, which includes alleviation of the symptoms of the disorder being treated. The novel methods of treatment of this invention are for disorders known to those skilled in the art. The term "prophylactically effective amount" as used herein means the amount of the active compound that will elicit the biological or medical response in a tissue, system, subject, mammal, or human that is being sought by the researcher, veterinarian, medical doctor or other clinician, to prevent the onset of the disorder in subjects as risk for obesity or the disorder. The therapeutically or prophylactically effective amount, or dosage, of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient may concomitantly require, and other factors in the physician's judgement.

Any suitable route of administration may be employed for providing a subject or mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of formula I are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 50 milligram per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

For the treatment of sexual dysfunction compounds of formula I are given in a dose range of 0.001 milligram to about 50 milligram per kilogram of body weight, preferably as a single dose orally or as a nasal spray.

When treating cachexia or weight loss generally satisfactory results are obtained when the compounds of formula I are administered at a daily dosage of from about 0.001 milligram to about 50 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

In the case where an oral composition is employed, a suitable dosage range is, e.g. from about 0.01 mg to about 1500 mg of a compound of Formula I per day, preferably from about 0.1 mg to about 600 mg per day, more preferably from about 0.1 mg to about 100 mg per day. For oral administration, the compositions are preferably provided in the form of tablets containing from 0.01 to 1,000 mg, preferably 0.01, 0.05, 0.1, 0.5, 1, 2.5, 3, 5, 10, 15, 20, 25, 30, 40, 50, 100, 250, 500, 600, 750, 1000, 1250 or 1500 milligrams of the active ingredient for the symptomatic adjustment of the dosage to the patient to be treated.

For use where a composition for intranasal administration is employed, intranasal formulations for intranasal administration comprising 0.001-10% by weight solutions or suspensions of the compounds of Formula I in an acceptable intranasal formulation may be used.

For use where a composition for intravenous administration is employed, a suitable dosage range is from about 0.001 mg to about 50 mg, preferably from 0.01 mg to about 50 mg, more preferably 0.1 mg to 10 mg, of a compound of Formula I per kg of body weight per day. This dosage regimen may be adjusted to provide the optimal therapeutic response. It may be necessary to use dosages outside these limits in some cases.

For the treatment of diseases of the eye, ophthalmic preparations for ocular administration comprising 0.001-1% by weight solutions or suspensions of the compounds of Formula I in an acceptable ophthalmic formulation may be used.

The magnitude of prophylactic or therapeutic dosage of the compounds of the present invention will, of course, vary depending on the particular compound employed, the mode of administration, the condition being treated and the severity of the condition being treated. It will also vary according to the age, weight and response of the individual patient. Such dosage may be ascertained readily by a person skilled in the art.

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I for the treatment or prevention of obesity and/or diabetes, either administered separately or in the same pharmaceutical compositions, include, but are not limited to:

(a) insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like), and compounds disclosed in WO 97/10813, WO 97/27857, WO 97/28115, WO 97/28137, and WO 97/27847; (iii) biguanides such as metformin and phenformin;

(b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$);

(c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide;

(d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like;

(e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics;

(f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo;

(g) PPARδ agonists, such as those disclosed in WO97/28149;

(h) PPAR α/δ agonists, such as muraglitazar, and the compounds disclosed in U.S. Pat. No. 6,414,002;

(i) smoking cessation agents, such as a nicotine agonist or a partial nicotine agonist such as varenicline, or a monoamine oxidase inhibitor (MAOI), or another active ingredient demonstrating efficacy in aiding cessation of tobacco consumption; for example, an antidepressant such as bupropion, doxepine, ornortriptyline; or an anxiolytic such as buspirone or clonidine; and (j) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB$_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer), and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; and EPO Application No. EP-658546, EP-656354, EP-576357; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A, and such as those disclosed in U.S. Pat. No. 5,705,515, and U.S. Pat. No. 5,451,677 and PCT Patent Publications WO94/18161, WO95/29159, WO97/46556, WO98/04526 and WO98/32753, WO 01/74782, and WO 02/32897; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001,836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR26928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, hereby incorporated by reference in their entirety; European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone I receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application Nos. JP 13226269, and JP 2004-139909; (11) melanin-concentrating hormone 2 receptor (MCH2R) agonist/antagonists; (12) orexin-1 receptor antagonists, such as SB-334867-A, and those disclosed in PCT Patent Application Nos. WO 01/96302, WO 01/68609, WO 02/51232, and WO 02/51838; (13) serotonin reuptake inhibitors such as fluoxetine, paroxetine, and sertraline, and those disclosed in U.S. Pat. No. 6,365,633, and PCT Patent Application Nos. WO 01/27060 and WO 01/162341; (14) melanocortin agonists, such as Melanotan II or those described in WO 99/64002 and WO 00/74679; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin), and those disclosed in: U.S. Pat. Nos. 6,410, 548; 6,294,534; 6,350,760; 6,458,790; 6,472,398; 6,376,509; and 6,818,658; US Patent Publication No. US2002/0137664; US2003/0236262; US2004/009751; US2004/0092501; and PCT Application Nos. WO 99/64002; WO 00/74679; WO 01/70708; WO 01/70337; WO 01/74844; WO 01/91752; WO 01/991752; WO 02/15909; WO 02/059095; WO 02/059107; WO 02/059108; WO 02/059117; WO 02/067869; WO 02/068387; WO 02/068388; WO 02/067869; WO 02/11715; WO 02/12166; WO 02/12178; WO 03/007949; WO 03/009847; WO 04/024720; WO 04/078716; WO 04/078717; WO 04/087159; WO 04/089307; and WO 05/009950; (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR146131, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as thioperamide, 3-(1H-imidazol-4-yl)propyl N-(4-pentenyl)carbamate, clobenpropit, iodophenpropit, imoproxifan, GT2394 (Gliatech), and those described and disclosed in PCT Application No. WO 02/15905, and O-[3-(1H-imidazol-4-yl)propanoyl]-carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (25) β-hydroxy steroid dehydrogenase-1 inhibitors (β-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives, such as those disclosed in U.S. Pat. Nos. 5,552,524, 5,552,523, 5,552,522, 5,521,283, and PCT International Publication Nos. WO 96/23513, WO 96/23514, WO 96/23515, WO 96/23516, WO 96/23517, WO 96/23518, WO 96/23519, and WO 96/23520; (32) BRS3 (bombesin receptor subtype 3) agonists such as [D-Phe6,beta-Ala11,Phe13, Nle14]Bn(6-14) and [D-Phe6,Phe13]Bn(6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron), and those disclosed in PCT Application Nos. WO 94/09134, WO 98/22128, and WO 99/43813; (35) monoamine reuptake inhibitors, such as sibutramine, and those disclosed in U.S. Pat. Nos. 4,746,680, 4,806,570, and 5,436,272, U.S. Patent Publication No. 2002/0006964 and PCT Application Nos. WO 01/27068, and WO 01/62341; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), retinoic acid, and those disclosed in PCT Patent Application No. WO 99/00123; (37) thyroid hormone β agonists, such as KB-2611 (KaroBioBMS), and those disclosed in PCT Application No. WO 02/15845, and Japanese Patent Application No. JP 2000256190; (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274444; and the compounds disclosed in U.S. Pat. No. 6,699,871, which is incorporated herein by reference; and International Patent Application Nos. WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)), and those disclosed in U.S. Pat. No. 5,026,685, U.S. Pat. No. 5,604,203, U.S. Pat. No. 5,574,010, U.S. Pat. No. 5,696,093, U.S. Pat. No. 5,936,092, U.S. Pat. No. 6,046,162, U.S. Pat. No. 6,046,167, U.S. Pat. No. 6,093,692, U.S. Pat. No. 6,225,445, U.S. Pat. No. 5,604,203, U.S. Pat. No. 4,002,531, U.S. Pat. No. 4,179,337, U.S. Pat. No. 5,122,614, U.S. Pat. No. 5,349,052, U.S. Pat. No. 5,552,520, U.S. Pat. No. 6,127,355, WO 95/06058, WO 98/32466, WO 03/026591, WO 03/057235, WO 03/027637, and WO 2004/066966, which are incorporated herein by reference; (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP) as described in Batterham et al., J. Clin. Endocrinol. Metab. 88:3989-3992 (2003), and other Y4 agonists such as 1229U91; (54) cyclo-oxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A and those disclosed in U.S. Pat. No. 6,001,836; and PCT Application Nos. WO 96/14307, WO 01/23387, WO 99/51600, WO 01/85690, WO 01/85098, WO 01/85173, and WO 01/89528; (56) Opioid antagonists such as nalmefene (Revex®), 3-methoxynaltrexone, naloxone, naltrexone, and those disclosed in: PCT Application No. WO 00/21509; (57) 11β HSD-1 (11-beta hydroxy steroid dehydrogenase type 1) inhibitor such as BVT 3498, BVT 2733, and those disclosed in WO 01/90091, WO 01/90090, WO 01/90092, and U.S. Pat. No. 6,730,690 and US Publication No. US 2004-0133011, which are incorporated by reference herein in their entirety; and (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; (88) zonisamide, and (89) Neurokinin-1 receptor antagonists (NK-1 antagonists) such as the compounds disclosed in: U.S. Pat. Nos. 5,162,339, 5,232, 929, 5,242,930, 5,373,003, 5,387,595, 5,459,270, 5,494,926, 5,496,833, and 5,637,699; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942, 97/21702, and 97/49710.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupropion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl) benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl) (3-{(1S)-2-fluoro-1-[3-fluoro-5-(4H-1,2,4-triazol-4-yl) phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl) methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl] benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl) (3-{(1S)-2-fluoro-1-[3-fluoro-5-(1,3,4-oxadiazol-2-yl) phenyl]-2-methylpropyl}azetidin-1-yl)methyl]benzonitrile, 3-[(S)-(4-chlorophenyl)(3-{(1S)-2-fluoro-1-[3-fluoro-5-(1, 2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl) azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl] benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl] benzonitrile, 5-{3-[(5)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl) phenyl]methyl}azetidin-3-yl)-2-fluoro-2-methylpropyl]-5-fluorobenzonitrile, 3-[(1S)-1-(1-{(S)-(4-cyanophenyl)[3-(1, 3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((1S)-1-{1-[(5)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl]-5-fluorobenzonitrile, 3-[(1S)-1-(1-{(S)-(4-chlorophenyl)[3-(1, 2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl] azetidin-1-yl}[3-(5-oxo-4,5-dihydro-1,3,4-oxadiazol-2-yl) phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b] pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'- carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H), 1'-cyclohexane]-4'-carboxamide, trans-N-[5-(3-fluorophenyl)-2-pyrimidinyl]-3-oxospiro[5-azaisobenzofuran-(3H),1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro[7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1R)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1R)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

Examples of other anti-obesity agents that can be employed in combination with a compound of Formula I are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Opin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest. Drugs,* 9: 1553-1571 (2000).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3,6,7,12,12a-hexahydro-2-methyl-6-(3,4-methylenedioxyphenyl)-pyrazino[2',1':6,1]pyrido[3,4-b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

The instant invention also includes administration of a single pharmaceutical dosage formulation which contains both the MC-4R agonist in combination with a second active ingredient, as well as administration of each active agent in its own separate pharmaceutical dosage formulation. Where separate dosage formulations are used, the individual components of the composition can be administered at essentially the same time, i.e., concurrently, or at separately staggered times, i.e. sequentially prior to or subsequent to the administration of the other component of the composition. The instant invention is therefore to be understood to include all such regimes of simultaneous or alternating treatment, and the terms "administration" and "administering" are to be interpreted accordingly. Administration in these various ways are suitable for the present compositions as long as the beneficial pharmaceutical effect of the combination of the MC-4R agonist and the second active ingredient is realized by the patient at substantially the same time. Such beneficial effect is preferably achieved when the target blood level concentrations of each active ingredient are maintained at substantially the same time. It is preferred that the combination of the MC-4R agonist and the second active ingredient be co-administered concurrently on a once-a-day dosing schedule; however, varying dosing schedules, such as the MC-4R agonist once a day and the second active ingredient once, twice or more times per day or the MC-4R agonist three times a day and the second active ingredient once, twice or more times per day, is also encompassed herein. A single oral dosage formulation comprised of both a MC-4R agonist and a second active ingredient is preferred. A single dosage formulation will provide convenience for the patient, which is an important consideration especially for patients with diabetes or obese patients who may be in need of multiple medications.

The compounds in the combinations of the present invention may be administered separately, therefore the invention also relates to combining separate pharmaceutical compositions into a kit form. The kit, according to this invention, comprises two separate pharmaceutical compositions: a first unit dosage form comprising a prophylactically or therapeutically effective amount of the melanocortin-4 receptor agonist, or a pharmaceutically acceptable salt or ester thereof, and a pharmaceutically acceptable carrier or diluent in a first unit dosage form, and a second unit dosage form comprising a prophylactically or therapeutically effective amount of the second active ingredient or drug, or a pharmaceutically acceptable salt or ester thereof, and a pharmaceutically acceptable carrier or diluent in a second unit dosage form. In one embodiment, the kit further comprises a container. Such kits are especially suited for the delivery of solid oral forms such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days or time in the treatment schedule in which the dosages can be administered.

Another aspect of the present invention provides pharmaceutical compositions which comprise a compound of Formula I, as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the typical oral dosage unit form, in which case solid pharmaceutical carriers are typically employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of structural formula I of the present invention can be prepared according to the procedures of the following Schemes and Examples, using appropriate materials and are further exemplified by the following specific examples. Moreover, by utilizing the procedures described in detail in PCT International Application Publication WO 04/089307 in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention:
AIBN is 2,2-azobisisobutyronitrile, BOC (Boc) is t-butyloxycarbonyl, $BOC_2O$ is BOC anhydride, BOP is benzotriazol-1-yloxytris(dimethylamino)-phosphonium hexafluorophosphate, Bn is benzyl, Bu is butyl, n-BuLi is n-butyl lithium, calc. or calc'd is Calculated, celite is Celite™ diatomaceous earth, CBS is tetrahydro-1-methyl-3,3-diphenyl-1H,3H-pyrrolo[1,2-c][1,3,2]oxazaborole, CBZ (Cbz) is benzyloxycarbonyl, c-hex is cyclohexyl, c-pen is cyclopentyl, c-pro is cyclopropyl, DBU is 1,8-diazabicyclo[5.4.0]undec-7-ene, DCM is dichloromethane, DEAD is diethyl azodicarboxylate, DIBAL is diisobutylaluminum hydride, DIEA or DIPEA is diisopropyl-ethylamine, DMA is dimethyl acetamide, DMAP is 4-dimethylaminopyridine, DMF is N,N-dimethylformamide, DMSO is dimethyl sulfoxide, dppf is 1,1'-Bis(diphenylphosphino)ferrocene, EDC is 1-(3-dimethylaminopropyl)-3-ethylcarbodiimide HCl, eq is equivalent(s), ESI-MS is electron spray ion-mass spectroscopy, Et is ethyl, EtOAc is ethyl acetate, h or hr is hour(s), HATU is O-(7-azabenzotriazol-1-yl)-1,1,3,3-tetramethyluronium hexafluorophosphate, HOAt is 1-hydroxy-7-azabenzotriazole, HOBt is 1-hydroxybenzotriazole hydrate, HPLC is high performance liquid chromatography, HMDS is hexamethyl disilazide, KHMDS is potassium hexamethyl disilazide, LiHMDS is lithium hexamethyl disilazide, LC-MS or LC-MASS is liquid chromatography mass spectrum, LDA is lithium diisopropylamide, LiHMDS is lithium hexamethyl disilazide, MC-xR is melanocortin receptor (x being a number), Me is methyl, min is minute(s), MF is molecular formula, MPLC is medium pressure liquid chromatography, MS is mass spectrum, Ms is methane sulfonyl, MTBE is methyl tert-butyl ether, NMM is N-methylmorpholine, NMO is N-Methylmorpholine-N-oxide, OTf is trifluoromethanesulfonyl, Ph is phenyl, Phe is phenyl alanine, Pr is propyl, iPr is isopropyl, prep. is prepared, PyBrop is bromo-tris-pyrrolidino-phosphonium hexafluoro-phosphate, r.t. or rt is room temperature, TBAF is tetrabutyl ammonium fluoride, TEA is triethylamine, Tf is triflate or trifluoromethanesulfonate, TFA is trifluoroacetic acid, THF is tetrahydrofuran, and TLC is thin-layer chromatography.

Reaction Schemes A-V illustrate methods employed in the synthesis of the compounds of the present invention of structural formula I. All substituents are as defined above unless indicated otherwise.

Reaction Scheme A illustrates a key step in the synthesis of the novel compounds of structural formula I of the present invention. As shown in reaction Scheme A, the reaction of a piperidine derivative of type 1 with a carboxylic acid derivative of formula 2 affords a title compound of structural formula I. The amide bond coupling reaction illustrated in reaction Scheme A is conducted in an appropriate inert solvent such as DMF, methylene chloride or the like and may be performed with a variety of reagents suitable for amide coupling reactions such as HATU, EDC or PyBOP. Preferred conditions for the amide bond coupling reaction shown in reaction Scheme A are known to those skilled in organic synthesis. Such modifications may include, but are not limited to, the use of basic reagents such as TEA, DIPEA, or NMM, or the addition of HOAt or HOBt. Alternatively, 4-substituted piperidines of formula 1 may be treated with an active ester or acid chloride derived from carboxylic acid 2 which also affords compounds of structural formula I. The amide bond coupling shown in reaction Scheme A is usually conducted at a temperature between 0° C. and room temperature, occasionally at elevated temperatures, and the coupling reaction is typically conducted for periods of 1 to 24 hours.

Scheme A

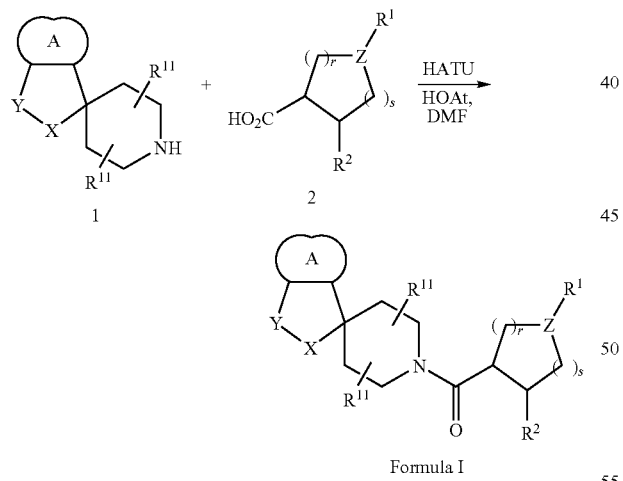

If it is desired to produce a compound of structural formula I wherein Z is a nitrogen and $R^1$ is a hydrogen, the N-BOC protected analogs of structural formula I may be used in the synthesis and deprotected under acidic conditions, for instance using trifluoroacetic acid in a solvent like methylene chloride or hydrogen chloride in a solvent such as ethyl acetate at a temperature between 0° C. and room temperature. When it is desired to prepare compounds of structural formula I wherein Z is a nitrogen and $R^1$ is not a hydrogen, the compounds of general formula I ($Z=N$, $R^1=H$) may be further modified using the methodology described below in reaction Scheme B. For example, the N-BOC protected compound of structural formula I can be deprotected under acidic conditions for instance by treatment with hydrogen chloride in ethyl acetate or using trifluoroacetic acid in dichloromethane as previously described. The resulting heterocyclic compound of structural formula I ($Z=N$, $R^1=H$) may then be subjected to one of several alkylation strategies known in organic chemistry to add another $R^1$ group. For instance, compounds of formula I ($Z=N$, $R^1=H$) may be utilized in a reductive amination reaction with a suitable carbonyl containing reagent 3. The reductive amination is achieved by initial formation of an imine between the amine of formula I ($Z=N$, $R^1=H$) and either an aldehyde or ketone of formula 3. The intermediate imine is then treated with a reducing agent capable of reducing carbon-nitrogen double bonds such as sodium cyanoborohydride or sodium triacetoxyborohydride and an alkylated product of structural formula I is produced. Alternatively, a heterocyclic compound of structural formula I ($Z=N$, $R^1=H$) may be directly alkylated using an alkylating agent such as 4 in a polar aprotic solvent such as DMF. In this reaction, the substituent leaving group, LG, of compound 4 is a leaving group such as a halide, mesylate or triflate, and the product is the compound of structural formula I ($Z=N$) bearing the $R^1$ substituent.

Scheme B

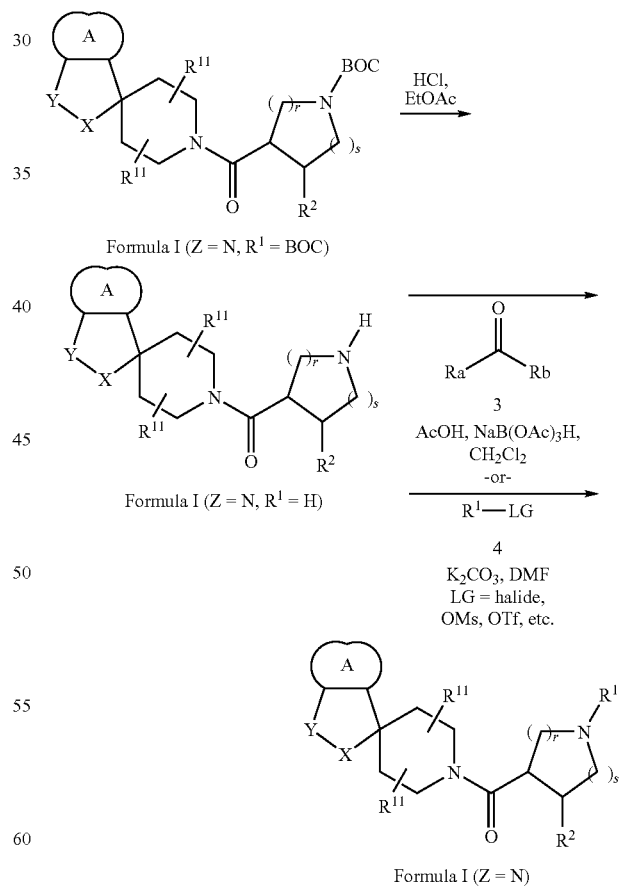

Reaction Schemes C—O illustrate methods for the synthesis of the carboxylic acids of general formula 2 that are utilized in the amide bond coupling reaction shown in reaction Scheme A. These schemes also feature methods for modification or elaboration of compounds of general formula I. Reaction Schemes P-U illustrate additional methods for the synthesis of 4,4-disubstituted piperidines of general formula 1 that are used in the amide bond coupling reaction, and also feature methods for elaboration of compounds of general formula I.

Reaction Scheme C illustrates a preferred method for the synthesis of compounds of general formula 2 wherein Z is a nitrogen, r is 2 and s is 1 such that the resulting heterocycle is a 3-aryl-4-piperidine carboxylic acid derivative 11 (n=1); and the synthesis of compounds of formula 2 wherein Z is a nitrogen, r is 1 and s is 1 such that the resulting heterocycle is a 3-aryl-4-piperidine carboxylic acid derivative 14 (n=2). The synthesis of 11 and 14 begins with a commercially available substituted benzene 5, such as difluorobenzene, which is derivatized to give the chloro ketone 6 via treatment with aluminum chloride and chloroacetylchloride. The ketone of 6 is reduced to the alcohol 7 using a borane N,N-diethylaniline complex and a solution of (S)-2-methyl-CBS oxazaborolidine in MTBE, and the chlorine is displaced by $R^1NH_2$, for instance tert-butyl amine, to give 8. The secondary amine nitrogen of 8 is alkylated with 4-bromo butyl nitrile (n=2) or 3-bromo propyl nitrile (n=1) to give nitrile compounds 9 and 12, which may be cyclized to the piperidine 13 and pyrrolidine 10 by treatment with LiHMDS and diethylphosphoryl chloride. Treatment of the nitrites 10 and 13 with sodium hydroxide provides the amides, which are subsequently converted to the corresponding methyl esters using HCl/MeOH and acetyl chloride, and to acids 11 and 14 by treatment with concentrated HCl. The resulting pyrrolidine acid 11 and piperidine acid 14 may be utilized in the coupling reaction shown in Scheme A.

Scheme C

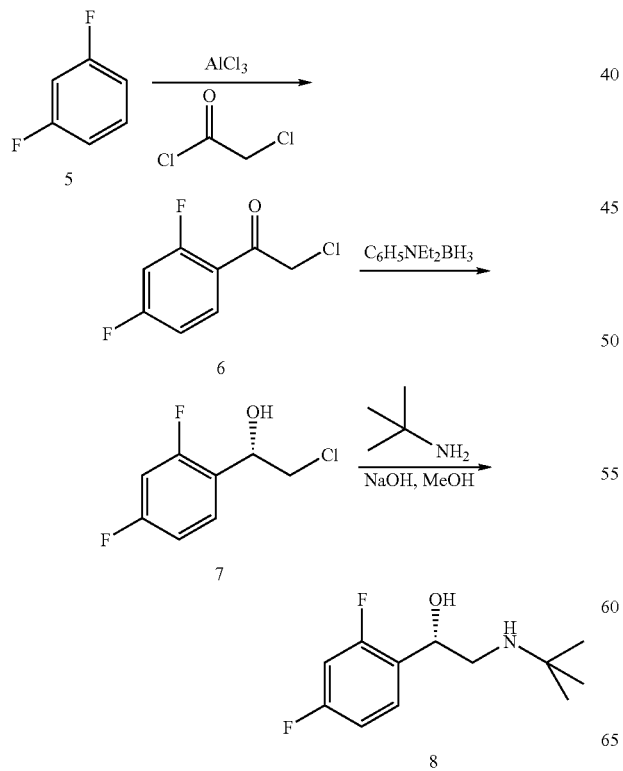

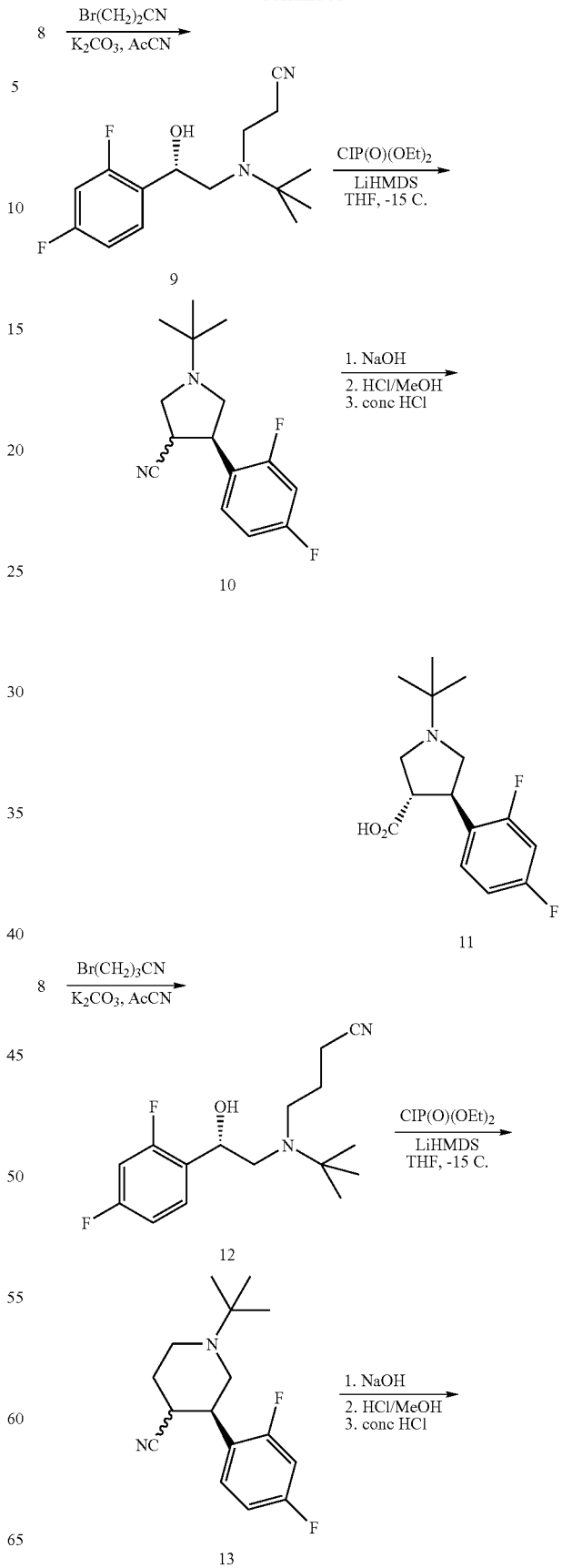

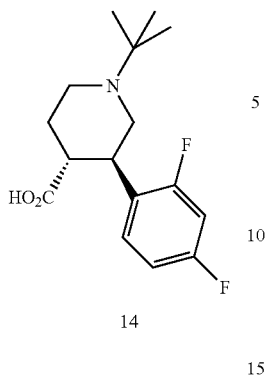

14

Reaction Scheme D illustrates a preferred method for the synthesis of compounds of general formula 2 wherein Z is a nitrogen, r is 1 and s is 2, such that the resulting heterocycle is a 4-aryl-3-piperidine-carboxylic acid derivative 21. The synthesis of 21 is similar to the synthesis shown in reaction Scheme C, and may begin with either of the commercially available β-keto esters 15 or 16. Conversion of 15 or 16 to the N-BOC-protected piperidine 17 is performed as shown and the resulting β-keto ester is subjected to the two-step arylation protocol previously described in Scheme C to yield 19. Reduction of the double bond of 19 using conditions appropriate for obtaining either cis or trans 20 is followed by ester hydrolysis which affords either a cis or trans 4-aryl-3-piperidine-carboxylic acid of general formula 21 which corresponds to an acid of general formula 2 wherein Z is a nitrogen, r is 1 and s is 2. The cis or trans carboxylic acids of general formula 21 are produced as racemates and either may be resolved to afford enantiomerically pure compounds by methods known in organic synthesis. Preferred methods include resolution by crystallization of diastereoisomeric salts derived from the acids 21 and a chiral amine base or by the use of chiral stationary phase liquid chromatography columns. As before, the cis or trans carboxylic esters 20 can also be resolved by the use of chiral stationary phase liquid chromatography columns.

Scheme D

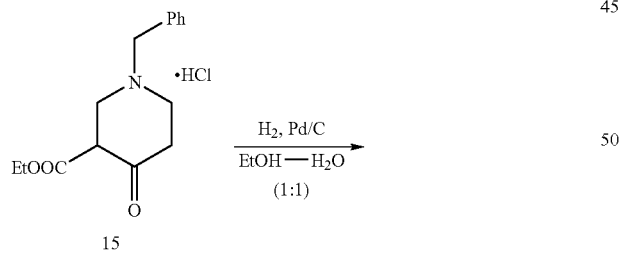

15

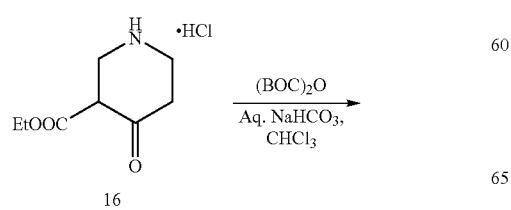

16

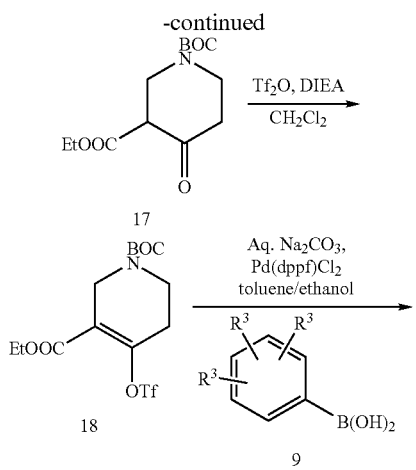

17

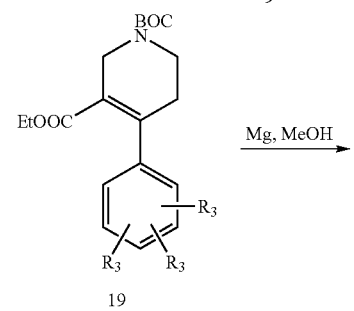

18

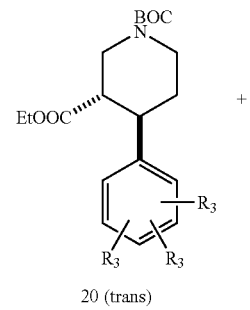

19

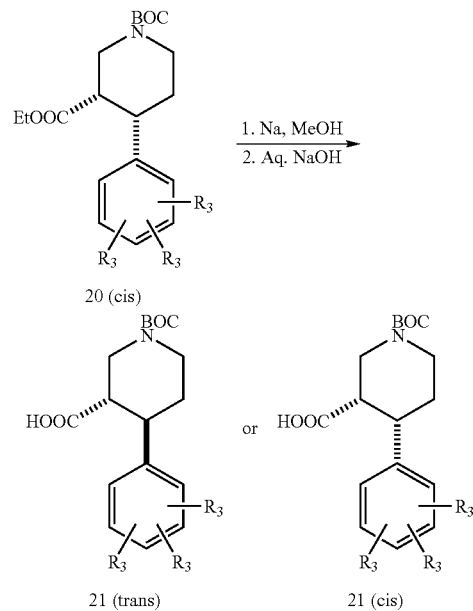

The synthesis of the N-BOC protected carboxylic acids of general formula 21 illustrated in reaction Scheme D is useful for the preparation of title compounds of structural formula I (Z=N) bearing a variety of $R^1$ substituents as noted above. For the synthesis of certain title compounds of structural formula I, for instance when it is desired that Z is nitrogen and $R^1$ is tert-butyl group, it is preferable to incorporate that $R^1$ substituent at an earlier stage of the synthesis. When it is desirable to synthesize a compound of general formula 21 wherein the BOC group is replaced with a substituent group $R^1$, a reaction sequence similar to the one illustrated in reaction Scheme D may be employed starting with a compound of general formula 17, which may be synthesized as shown in reaction Scheme E. An amine 22 bearing the desired $R^1$ substituent is first subjected to a Michael addition with excess ethyl acrylate in the presence of a solvent such as THF or ethanol. The resulting diester 23 is then converted to a 1-substituted-4-ketopiperidine-3-carboxylic ester 24 using an intramolecular Dieckmann reaction. The substituted piperidine 24 corresponds to a compound of general formula 17 shown in reaction Scheme D, wherein the BOC group is replaced with the desired $R^1$ substituent. The compounds of general formula 24 may then be converted to compounds of general formula 2 where the $R^1$ substituent replaces the BOC group using the methodology illustrated in reaction Scheme D.

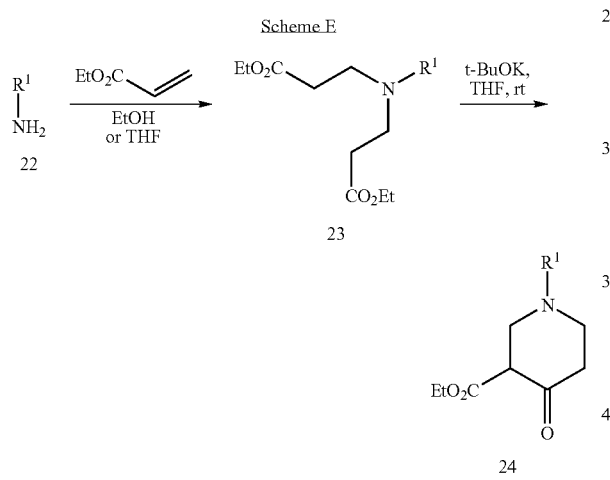

Reaction Schemes F and G illustrate the synthesis of the novel compounds of structural formula I (Z=C) when it is preferred to effect the amide bond coupling step prior to incorporation of the basic substituent $R^1$ as mentioned above. Reaction Scheme F illustrates a method for the synthesis of compounds of structural formula I which employs a piperidine of general formula 1 and a cycloalkanone carboxylic acid of general formula 25 as the partners in the amide bond coupling step. The piperidine of formula 1 and the carboxylic acid of formula 25 are first coupled to afford an amide of general formula 26 using the reagents and conditions described for the generalized amide coupling shown in reaction Scheme A. The $R^1$ substituent ($R^1$=$NR^7R^8$) may then be incorporated at the position of the carbonyl group by performing a reductive amination reaction with an amine of general formula 27. Typical conditions for effecting such a reductive amination include preforming an imine 28 from ketone 26 and amine 27 followed by reduction of the intermediate imine with reducing agents such as sodium borohydride, sodium cyanoborohydride or sodium triacetoxyborohydride. Formation of the intermediate imine 28 derived from piperidine 1 and acid 25 may occur spontaneously in solution or it may be promoted with agents such as titanium (IV) isopropoxide in a solvent such as methanol or with anhydrous magnesium sulfate in chloroform. The formation of the imine 28 is generally performed at temperatures between 0° C. and the reflux temperature of the solvent, frequently at room temperature. The imine formation step is generally allowed to proceed to completion over a period of several hours to 1 day prior to the reduction step which minimizes the formation of secondary alcohols formed by simple reduction of the keto group in compounds of general formula 26. The intermediate imine 28 may in some cases be isolated and purified, however it is generally preferred to use it directly in the reduction step. The reduction of the imine 28 is typically conducted in an alcoholic solvent such as methanol or ethanol at temperatures between 0° C. and room temperature, and the reduction is generally completed in several hours or less.

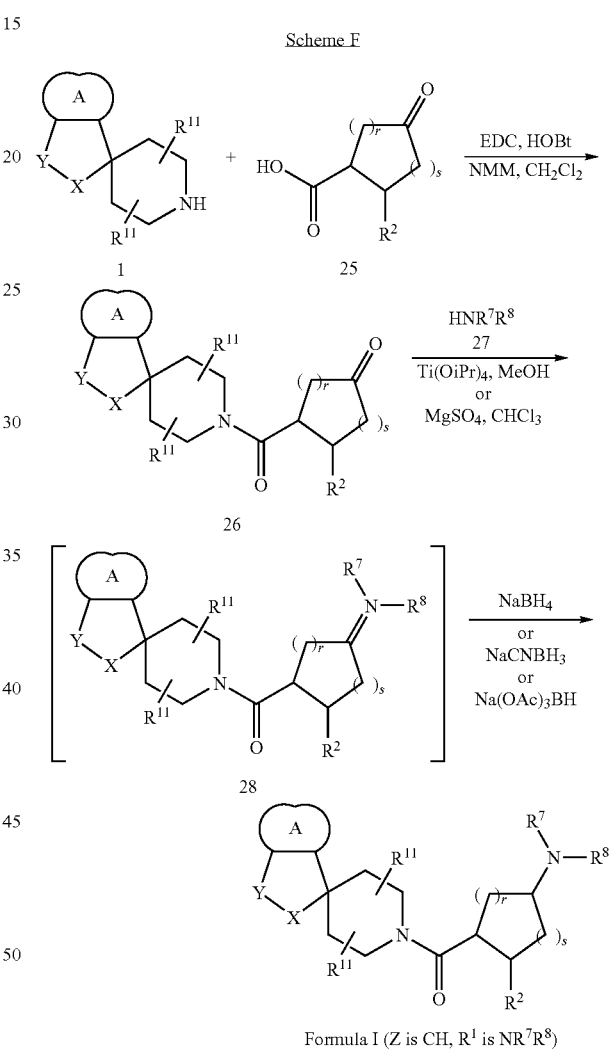

Reaction Scheme G illustrates a preferred method for the synthesis of compounds of structural formula I (Z is CH) which employs a piperidine of general formula 1 and a hydroxyl-substituted cycloalkyl carboxylic acid of general formula 29 as the partners in the amide bond coupling step. The amide bond coupling step between piperidine 1 and carboxylic acid 29 is performed first, typically using a carbodiimide reagent like EDC to promote the coupling as described above or by any of the other methods described in the discussion for reaction Scheme A. The hydroxyl-substituted amide 30 which is produced is then further synthetically modified to incorporate the $R^1$ substituent present in the title compounds of structural formula I (Z is CH). A variety of methods known to those skilled in organic synthesis may be used to incorporate the $R^1$ substituent. For instance, the hydroxyl group of compounds of general formula 30 may be oxidized using a variety of methods to afford carbonyl compounds of general formula 26. The resulting ketoamides of general formula 26 may then be converted to the title compounds of structural formula I (Z is CH) using the reductive amination method described in reaction Scheme F.

Occasionally, it may be preferable to utilize hydroxyl-substituted compounds of general formula 30 in a Fukuyama-Mitsunobu reaction (Fukuyama, T.; Cheung, M.; Jow, C.-K.; Hidai, Y.; Kan, T. *Tetrahedron Lett.* 1997, 33, 5831-4) sequence as shown in reaction Scheme H. In this method for the synthesis of the novel title compounds of structural formula I (Z is CH), the intermediate hydroxyl-substituted cycloalkylamide 30 is reacted with a 2,4-dinitrobenzenesulfonamide of general formula 31 in the presence of triphenylphosphine and an azodicarboxylate reagent such as DEAD. The reaction is performed in a suitable aprotic solvent such as benzene, toluene or tetrahydrofuran, typically at room temperature, and the reaction is generally complete in 0.5-3 hours. The product of this reaction is the secondary 2,4-dinitrobenzenesulfonamide of general formula 32, which may then be readily converted to a title compound of structural formula I (Z is CH) wherein $R^8$ is H. The deprotection of the sulfonamide group is accomplished by reaction of 32 with either a base like n-propylamine in a solvent like methylene chloride or by reaction of 32 with a nucleophilic reagent such as mercaptoacetic acid with triethylamine in methylene chloride. In either case the reaction is typically conducted at room temperature, for periods of 5 minutes to one hour. An advantage of the Fukuyama-Mitsunobu reaction sequence is that the stereochemistry of the carbon atom undergoing substitution is cleanly inverted. Thus if the hydroxyl-substituted cycloalkylamide 30 is a single diastereoisomer, then the product 32 will be a single diastereoisomer also. This is in contrast to the reductive amination strategy discussed in reaction Scheme F which generally affords a mixture of epimeric products.

The secondary amine of formula I (Z is CH, $R^1$ is $N(H)R^7$) shown in reaction Scheme G may then be further synthetically modified using a variety of methods known in organic synthesis to incorporate other embodiments of the $R^8$ substituent. For instance, a compound of structural formula I (Z is CH) where $R^8$=H may be subjected to a reductive amination reaction with an appropriate aldehyde or ketone using the conditions described in reaction Scheme F. Alternatively, a compound of structural formula I (Z is CH) where $R^8$ is H may be directly alkylated with an appropriate alkylating agent using the conditions described in reaction Scheme B.

Scheme G

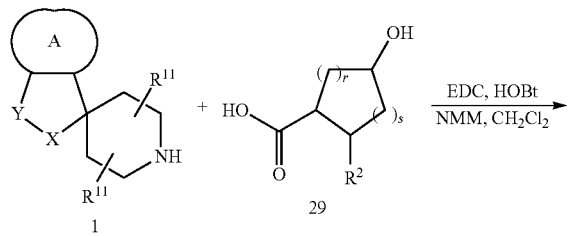

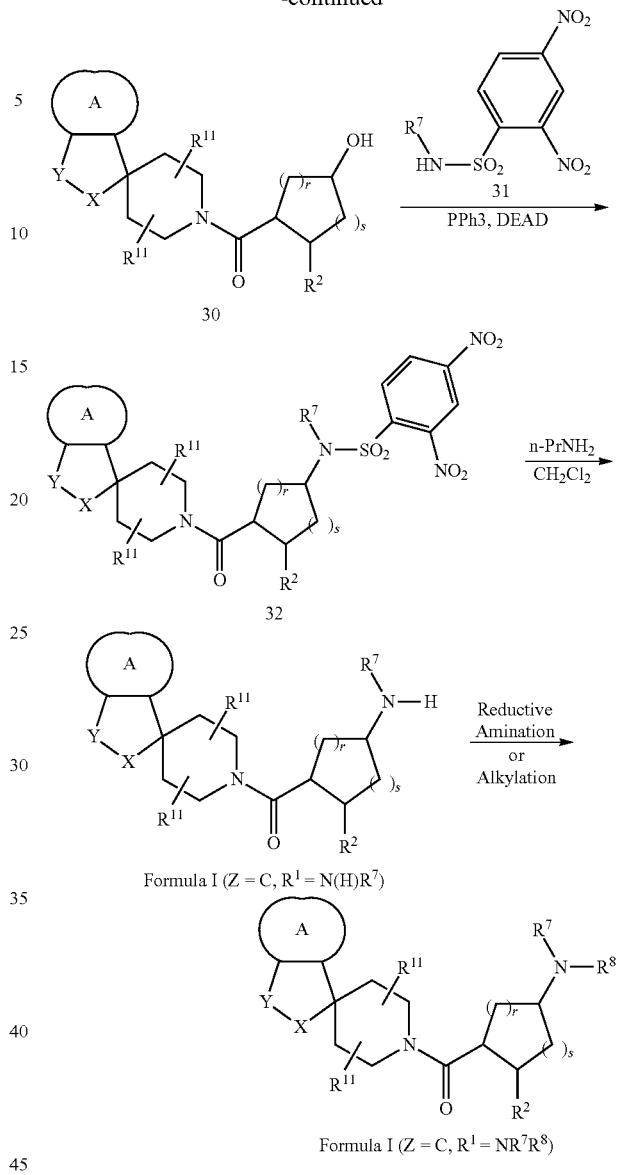

Enantiomerically pure compounds may be prepared from starting materials bearing a suitable covalently attached chiral auxiliary group using synthetic transformations similar to those outlined above. Reaction Scheme H illustrates the use of a covalently attached chiral oxazolidinone auxiliary for the preparation of enantiomerically pure cyclopentanones of general formula 41. In this synthetic method, cinnamyl oxazolidinones of general formula 35 are readily prepared from cinnamic acids and (S)-(−)-4-benzyl-2-oxazolidinone using published methodology (Ho, G.-J.; Mathre, D. J. *J. Org. Chem.* 1995, 60, 2271 and references cited therein). The acylation of chiral auxiliary 34 with cinnamic acids of formula 33 is performed by initial activation of the acid to afford a mixed anhydride. Typically acids of general formula 33 are reacted with an acid chloride such as pivaloyl chloride in the presence of a base such as triethylamine and in a suitable aprotic solvent such as THF. The intermediate cinnamyl-pivaloyl anhydride is converted to the product 35 by reaction with the oxazolidinone 34 in the presence of lithium chloride, an amine base such as triethylamine and in a solvent such as THF, and the reaction is conducted at temperatures between −20° C. and room temperature for periods of 1-24 hours. Alternatively, the oxazolidinone 34 may be deprotonated with a strong base such as n-butyllithium in THF at low temperatures such as −78° C. and then reacted with a mixed anhydride obtained from acid 33 and an acid chloride like pivaloyl chloride as noted above. The α,β-unsaturated acyloxazolidone of general formula 35 is subjected to the trimethylenemethane cycloaddition reaction (Trost, B. M.; Chan, D. M. T. *J. Am. Chem. Soc.* 1979, 101, 6429) with compound 36 to afford a cyclopentane derivatives of general formula 37 and 38. The cycloaddition is performed by reacting the α,β-unsaturated ester of general formula 35 with 2-[(trimethylsilyl)methyl]-2-propen-1-yl acetate 36 in the presence of a palladium(0) catalyst in a solvent such as tetrahydrofuran. A preferred palladium (0) catalyst for the cycloaddition may be generated by mixing palladium acetate and triisopropyl phosphite in the reaction mixture. The cycloaddition reaction is typically conducted at the reflux temperature of the solvent, for instance 65° C., and the reaction is usually completed in periods of 2-8 hours. The olefin geometry of the starting α,β-unsaturated ester of general formula 35 determines the relative stereochemistry of the two substituents on the five-membered ring. Thus a trans α,β-unsaturated ester 35 affords the trans-disubstituted products 37 and 38 as shown, whereas the corresponding cis isomer of compounds of general formula 35 affords the corresponding cis-disubstituted isomer of 37 and 38. The exocyclic olefin present in compounds of general formula 40 is oxidatively removed to afford a cyclopentanone derivative of general formula 41.

Compounds of general formulae 37 and 38 are readily separated from each other by conventional chromatographic methods or by recrystallization, and may then be converted to the compounds of general formula 41 individually. This process is illustrated at the bottom of reaction Scheme H for the case of the cyclopentane with the absolute stereochemistry shown in formula 39. The enantiomerically pure compounds of general formula 39 are first hydrolyzed to afford intermediate carboxylic acids and (S)-(−)-4-benzyl-2-oxazohdinone using a reagent such as lithium hydroperoxide, typically generated in situ, in a suitable solvent system such as aqueous tetrahydrofuran. The carboxylic acid formed is generally then converted to a methyl ester 40 using diazomethane, trimethylsilyldiazomethane or any of the esterification methods commonly employed in organic synthesis. The olefin present in the esters of general formula 40 is then subjected to oxidative cleavage to afford enantiomerically pure compounds of general formula 41. The methylene cyclopentane derivative of formula 40 is first oxidized to a 1,2-diol derivative using catalytic osmium tetraoxide in the presence of a stoichiometric reoxidant such as N-methylmorpholine-N-oxide and a solvent system such as acetone-water. The intermediate 1,2-diol which forms is generally not isolated, but is in turn subjected to cleavage with sodium periodate in a solvent system like methanol-water to afford ketones of general formula 41. Both steps in the oxidative cleavage sequence are generally completed during periods of several minutes to a few hours and the reaction steps are typically conducted at low temperatures, for instance between 0° C. and room temperature. Alternatively, the oxidative cleavage of olefins of general formula 40 may be accomplished using ozone, or by other methods known in organic synthesis. The cyclopentanones of general formula 41 may then be hydrolyzed, for instance using sodium hydroxide in methanol, to afford the carboxylic acids of general formula 42 (r=1, s=1). The acids of general formula 42 are finally converted to the novel title compounds of structural formula I (Z=C) using the methodology described above in reaction Schemes F and G.

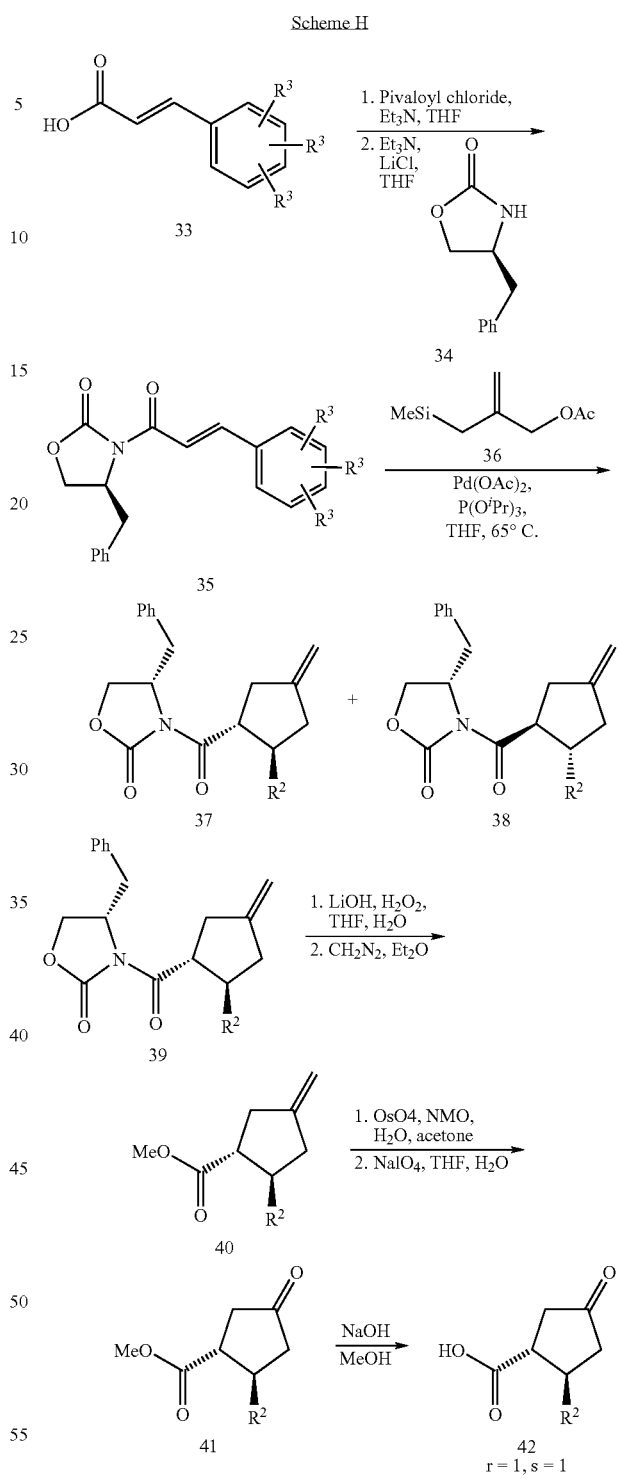

Scheme H

When it is desired to prepare individual enantiomers of the novel title compounds of structural formula I, it is possible to perform a resolution of the compounds of structural formula I using one of the methods known in the art of organic synthesis. For instance, enantiomerically pure compounds of formula I may be prepared by crystallization of diastereoisomeric salts formed from the racemic compounds of structural formula I and an optically active carboxylic acid. The two diastereoisomeric salts are separated from each other by fractional crystallization, then the enantiomerically pure compounds of structural formula I are regenerated by treatment of the purified salts with a base. Alternatively, racemic compounds of structural formula I may be resolved by preparative HPLC using commercially available chiral stationary phase columns. Another strategy for the preparation of enantiomerically pure compounds of structural formula I involves preparing enantiomerically pure compounds of general formula 2 prior to their use in the amide bond forming reaction outlined in reaction Scheme A. Racemic compounds of general formula 2, or intermediates used to prepare compounds of formula 2 as described in the previous reaction Schemes (i.e. acids 11, 14, 21, and 42, or esters 20 and 41) may also be resolved using the classical methods previously discussed.

Scheme I discloses examples of 4,4-disubstituted piperidine intermediates of general formula 1 used as indicated in the examples of the present invention. The 4,4-disubstituted piperidine intermediates of general formula I-1, 1-2 and I-3 in Scheme I, which may be employed to synthesize the compounds of this invention, may be prepared according to the methods disclosed in U.S. Pat. No. 5,804,578 (Sep. 8, 1998), U.S. Pat. No. 5,578,593 (Nov. 26, 1996), U.S. Pat. No. 6,472,398 (Oct. 29, 2002), U.S. Pat. No. 6,294,534 (Sep. 25, 2001), WO 01/70337, WO 99/64002, and WO 04/089307.

Scheme I

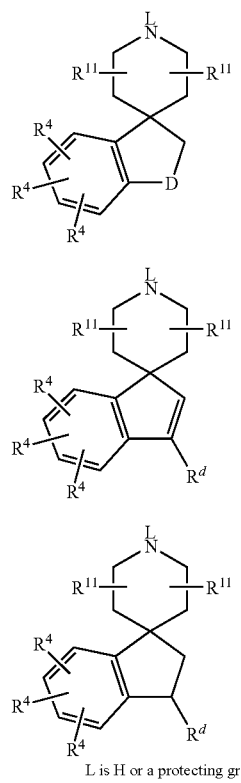

L is H or a protecting group
D is O, S, NR, NH, NS(O)$_2$R, S(O), or S(O)$_2$, or CH(R$^7$)
R$^7$ is (CH$_2$)$_n$ aryl, —C(O)R$^2$, —SO$_2$R$^2$, —C(O)NR$^2$)$_2$, —CO$_2$R$^2$,
—SO$_2$NR$^2$, or as defined in 5,804,578
R$^2$ is a defined in 5,804,578
R$^d$ is (CH$_2$)$_n$CO$_2$H, (CH$_2$)$_n$CO$_2$Me, —CON(R$^2$)$_2$, -OTs, -OTf, CN, —SMe,
tetrazole, pyridine, —Sn(Me)$_3$ or as defined in 5,804,578

Reaction Scheme J illustrates a preferred method for the synthesis of a compound of general formula 1 (X=C, Y=CHN(H)CBZ). In this method, a carboxylic acid such as 43 is subjected to the Curtius reaction to afford a product of general formula 44. The reaction is performed by reacting acid 43 with diphenylphosphoryl azide in the presence of a tertiary amine such as triethylamine or diisopropylamine in a solvent such as toluene. The rearrangment is typically conducted at the reflux temperature of the solvent, for instance 110° C., and the rearrangement is usually completed in periods of 1-5 hours. The intermediate isocyanate which forms is generally not isolated, but is in turn subjected to in-situ reaction with a suitable alcohol such as benzyl alcohol to afford a product of general formula 44. The N-BOC group can be removed by any of the known methods such as treatment with a protic acid such as hydrogen chloride in an inert organic solvent such as ethyl acetate or trifluoroacetic acid in methylene chloride. The product amine 45 can be used as a coupling partner in reaction Scheme A.

Scheme J

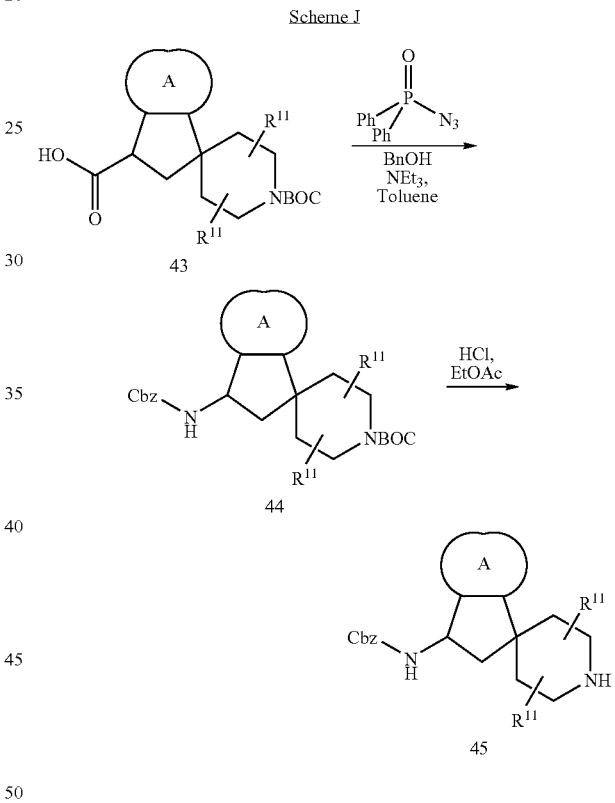

Reaction Scheme K illustrates general methods for the elaboration of the Y substituent following assembly of compounds of structural formula I (X=CH$_2$, Y=CHCO$_2$Me) as described in reaction Scheme A. For example, conversion of the methyl ester to the carboxylic acid of structural formula I (X=CH$_2$, Y=CHCO$_2$H) can be affected by dealkylation using potassium trimethylsilanolate at room temperature in an inert organic solvent such as tetrahydrofuran for a period of about one to about 24 hours to provide, after acidification, the corresponding carboxylic acid. In certain cases, a base-catalyzed hydrolysis known to those skilled in the art may be used to effect this same transformation. The acid may be reacted further to form an amide by treatment with a primary or secondary amine under a variety of amide coupling protocols such as those described in Scheme A to provide a compound of structural formula I (X=CH$_2$, Y=CHCONR$^7$R$^8$).

Scheme K

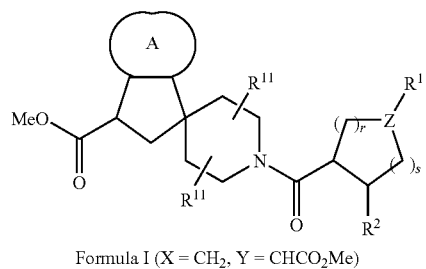

Formula I (X = CH$_2$, Y = CHCO$_2$Me)

→ NaOH, THF or (Me)$_3$SiOK, THF →

Scheme L

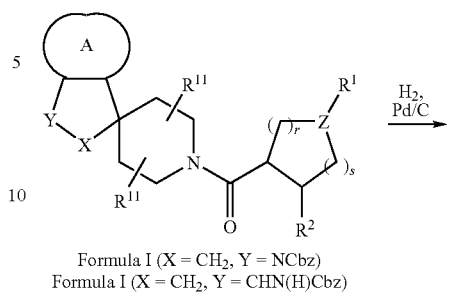

Formula I (X = CH$_2$, Y = NCbz)
Formula I (X = CH$_2$, Y = CHN(H)Cbz)

→ H$_2$, Pd/C →

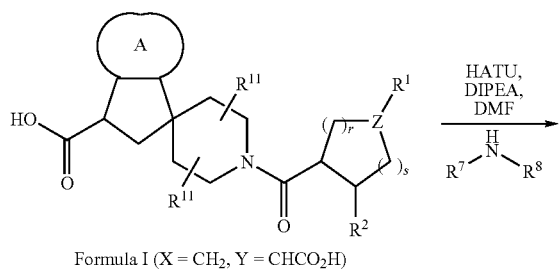

Formula I (X = CH$_2$, Y = CHCO$_2$H)

→ HATU, DIPEA, DMF; R$^7$N(H)R$^8$ →

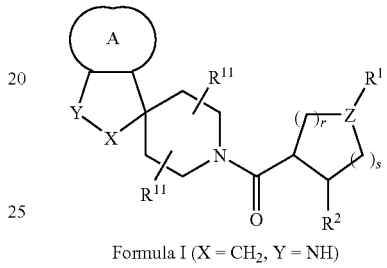

Formula I (X = CH$_2$, Y = NH)
Formula I (X = CH$_2$, Y = CHNH$_2$)

→ RCOCl (46), NEt$_3$, CH$_2$Cl$_2$ -or- HATU, DIPEA, DMF, RCO$_2$H (47) →

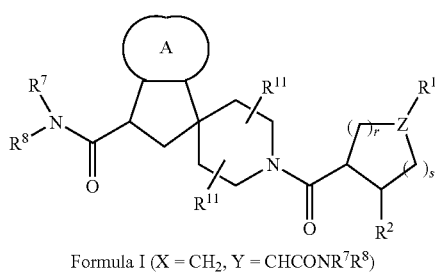

Formula I (X = CH$_2$, Y = CHCONR$^7$R$^8$)

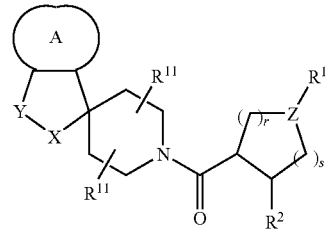

Formula I (X = CH$_2$, Y = NC(O)R)
Formula I (X = CH$_2$, Y = CHNHC(O)R)

R = R$^5$ or OR$^5$

Reaction Scheme L illustrates general methods for the elaboration of the Y substituent following assembly of compounds of structural formula I (X=CH$_2$, Y→N(H)CBZ or CHN(H)CBZ) as described in reaction Scheme A. The N-CBZ protected compound of structural formula I (X=CH$_2$, Y=N(H)CH or CHN(H)CBZ) is first deprotected by hydrogenolysis using a palladium-on-carbon catalyst in a solve system such as methanol, ethanol, acetic acid or mixtures thereof under a hydrogen atmosphere. The resulting compound of structural formula I (X=CH$_2$, Y=NH or CHNH$_2$) may then be subject to one several acylation methods known in organic chemistry. For instance, a compound of structural formula I (X=CH$_2$, Y=NH or CHNH$_2$) can be reacted with a carboxylic acid 47 under a variety of amide coupling protocols such as those described in the discussion for Scheme A to provide a product of structural formula I (X=CH$_2$, Y=NC(O)R or CHNHC(O)R). Alternatively, a compound of structural formula I (X=CH$_2$, Y=NH or CHNH$_2$) may be acylated using an acid chloride derivative 46. The acylation reaction is typically conducted in the presence of a tertiary amine like triethylamine, N,N-diiso-propylethylamine or N-methylmorpholine in an aprotic solvent such as methylene chloride or DMF to afford a product of structural formula I (X=CH$_2$, Y=NC(O)R or CHNHC(O)R) as shown in Scheme L.

Reaction Scheme M illustrates general methods for the elaboration of the Y substituent following assembly of compounds of structural formula I (X=CH$_2$, Y=NH) as described in the preceeding reaction Scheme L. For example, a compound of structural formula I (X=CH$_2$, Y=NH) may be subjected to one of several alkylation strategies known in organic chemistry. For instance, compound I (X=CH$_2$, Y=NH) may be utilized in a reductive amination reaction with a suitable carbonyl containing partner (67). The reductive amination is achieved by initial formation of an imine between the amine of formula I (X=CH$_2$, Y=NH) and either an aldehyde or ketone of formula 48. The intermediate imine is then treated with a reducing agent capable of reducing carbon-nitrogen double bonds such as sodium cyanoborohydride or sodium triacetoxyborohydride and an alkylated product of structural formula I (X=CH$_2$, Y=NR) is produced. Alternatively, a compound of structural formula I (X=CH$_2$, Y=NH) may be directly alkylated using an alkylating agent such as 49 in a polar aprotic solvent such as DMF. In this reaction, the substituent leaving group, LG, of compound 49 is a leaving group such as a halide, mesylate or triflate and the product is the compound of structural formula I (X=CH$_2$, Y=NR$^6$).

Scheme M

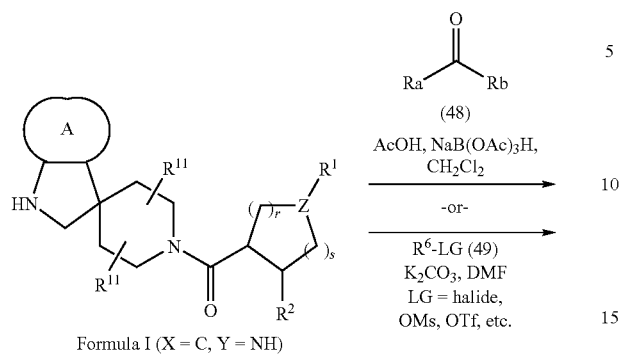

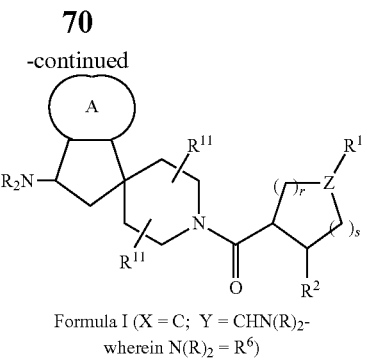

The following examples are provided to illustrate the invention and are not to be construed as limiting the scope of the invention in any manner.

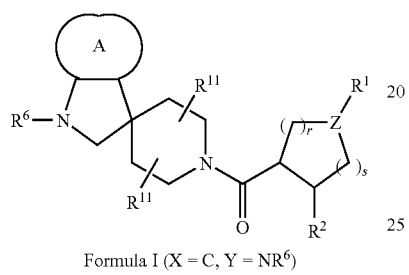

In a similar manner to the conditions described in reaction Scheme M, compounds of structural formula I (X=CH$_2$, Y=CHNH$_2$) can be elaborated to products of structural formula I (X=CH$_2$, Y=CHN(H)R), and can be further elaborated to products of structural formula I (X=CH$_2$, Y=CN(R)$_2$), as shown in Scheme N.

Scheme N

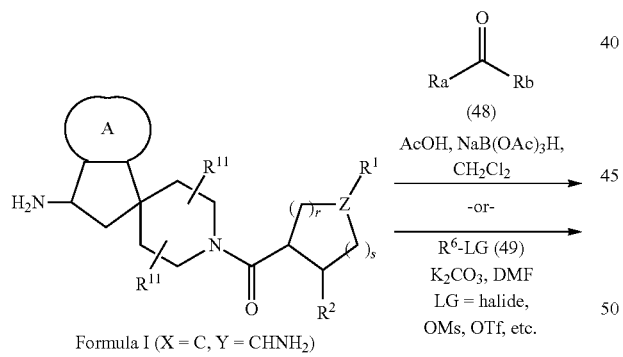

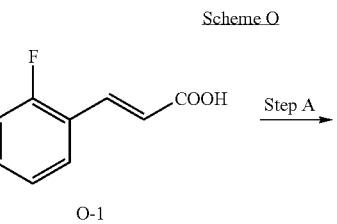

Scheme O

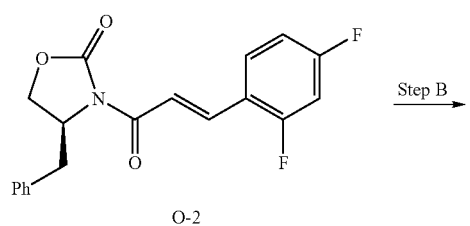

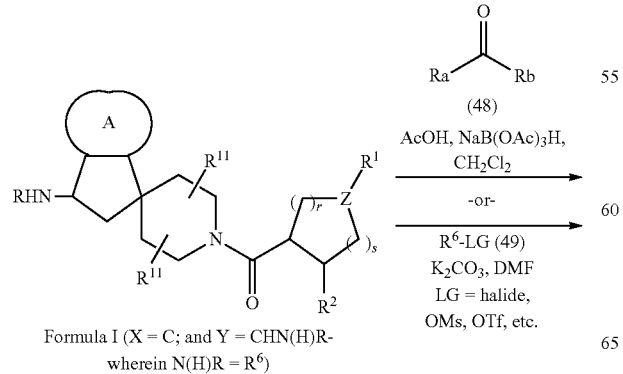

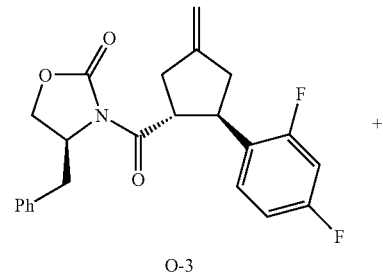

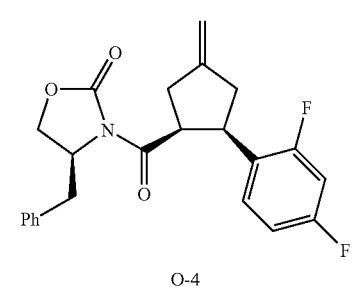

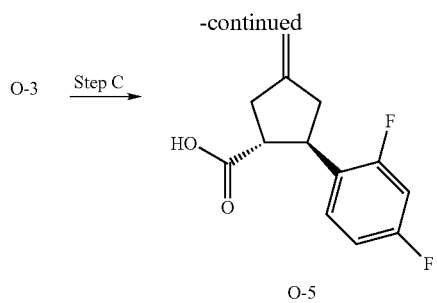

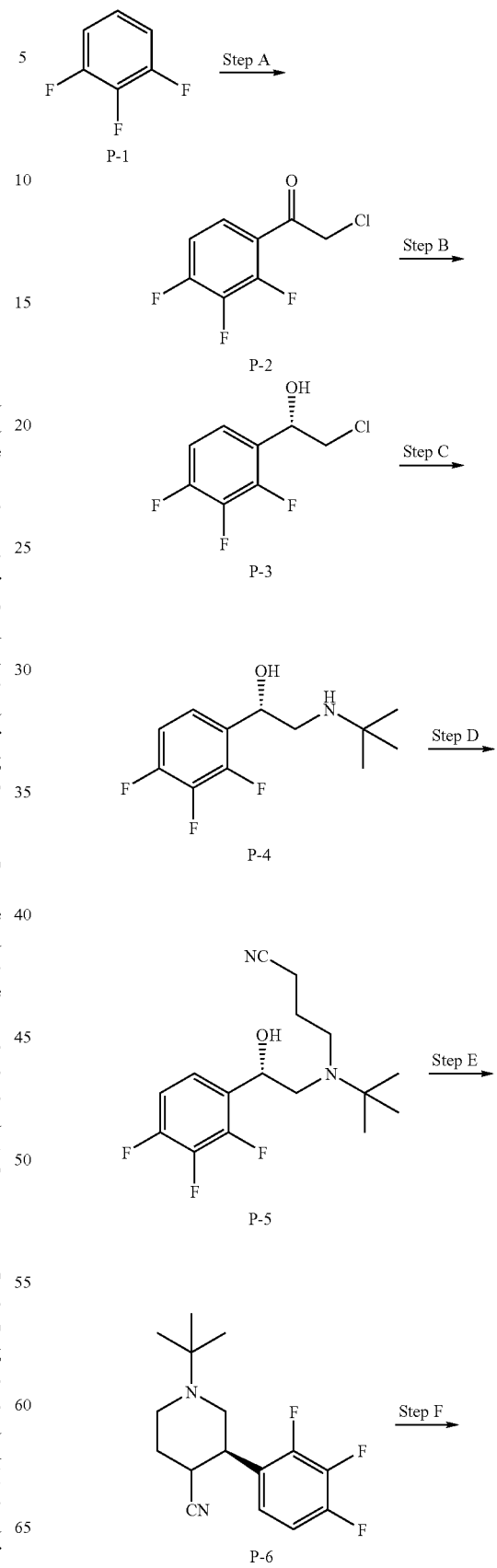

Preparation of Intermediate O-5: (3R,4R)—N-t-butyl-3-(2',3',4'-trifluorophenyl)piperidine-4-carboxylic Acid Step A: To a solution of trans-2,4-difluorocinnamic acid O-1 (7.6 g, 41.3 mmol, Aldrich) in THF (150 mL) was added triethylamine (17.3 mL, 123.8 mmol). The reaction mixture was cooled to −40° C. and trimethyl acetic chloride (5.1 mL, 47.3 mmol) was added slowly. After the reaction mixture was stirred at 40° C. for another 2 hours, lithium chloride (1.93 g, 45.40 mmol) was added, followed by s-4-benzyl-2-oxazolidinone (7.31 g, 41.3 mmol). After stirring at −40° C. for another 20 min., reaction mixture was allowed to warm up to room temperature and stirred at r.t. for 18 hrs. The reaction mixture was poured into aqueous of saturated ammonium chloride (180 mL); the phases were separated and the aqueous phase was extracted with ethyl acetate. The combined ethyl acetate extracts were washed with brine, dried over $MgSO_4$ and concentrated to give a residue. The resulting residue was purified by crystallization from EtOAc/hexane to give compound 0-2. ESI-MS calc. for $C_{19}H_{15}F_2NO3$: 343. Found: 344 (M+H), 366 (M+Na).

Step B: To a solution of Compound O-2 (2.3 g, 6.55 mmol) in THF (30 mL) was added palladium acetate (73.6 mg, 0.33 mmol) and 2-[(trimethylsilyl)methyl]-2-propenol-yl acetate (1.8 mL, 8.52 mmol). The reaction vessel was evacuated under vacuum and purged with nitrogen 3 times, then triisopropyl phosphate (0.45 mL, 1.97 mmol) was added. The reaction mixture was heated at 65° C. for 18 hrs, cooled to r.t. and concentrated to give a residue. The resulting residue was partitioned between ethyl acetate and water, and the aqueous layer was extracted with ethyl acetate. The combined extracts were washed with brine, dried over $MgSO_4$ and concentrated to give a residue. The resulting residue was purified by HPFC (2-30% ethyl acetate in hexane) to give a yellow oil 04 (0.89 g, fast elusion) and white solid O-3 (0.85 g, slow elusion). ESI-MS calc. for $C_{23}H_{21}F_2NO3$: 397. Found: 398 (M+H), 420 (M+Na).

Step C: To a solution of Compound O-3 (1.7 g, 4.28 mmole) in THF (24 mL) and water (6 mL) under nitrogen at 0° C. was added lithium hydroxide monohydrate (0.36 g, 8.56 mmole) and $H_2O_2$ (30% solution, 2.5 mL, 25.7 mmole). After stirring the reaction mixture at 0° C. for half an hour, the mixture was warmed up to r.t. and stirred for 1.5 hours. The solvent was removed, the pH was adjusted to pH 9-10 with a saturated $NaHCO_3$ solution and the mixture was extracted with $CH_2Cl_2$. The aqueous layer was acidified with HCl (2N) to pH 1-2, and the mixture was extracted with $CH_2Cl_2$. The combined methylene chloride layers were dried over $MgSO_4$ and concentrated to give colorless oil O-5. ESI-MS calc. for $C_{13}H_{12}F_2O2$: 238. Found: 239 (M+H).

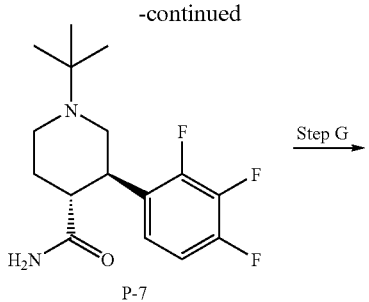

P-7

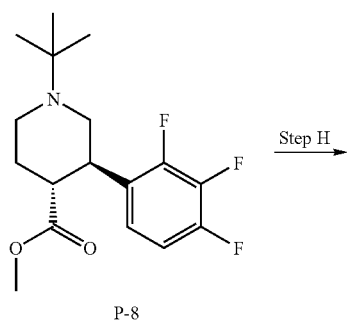

P-8

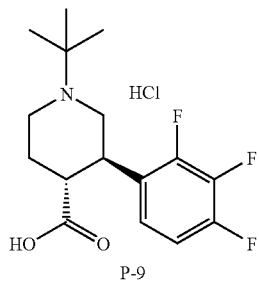

P-9

Preparation of Intermediate P-9 (3R,4R)—N-t-butyl-3-(2,'3',4'-trifluorophenyl)piperidine-4-carboxylic Acid Step A: To a solution of 1,2,3-trifluorobenzene P-1 (27.39 g, 207.4 mmol) and aluminum chloride (55 g, 414.8 mmol), was added dropwise chloroacetyl chloride (46.84 g, 414.8 mmol) over 10 minutes. The mixture was heated slowly to 65° C. for 2 hours and stirred at room temperature over night. The reaction mixture was then poured into 400 g of ice and extracted with methylene chloride (3×300 mL). The combined organic phases were washed with water (2×300 mL), brine, dried over MgSO$_4$, filtered and concentrated. Then 200 mL hexanes was added and the mixture was heated until all the solid dissolve. The mixture was cooled to room temperature and then to 0° C. in freezer to give crystals. The crystals were filtered, and washed with cold hexanes to provide compound P-2 (Rf=0.4 by ethyl acetate:hexanes=1:9).

Step B: To a solution of borane N,N-diethylaniline complex (12.90 g, 79.11 mmol) and (S)-2-methyl-CBS-oxazaborolidine (3.60 mL, 1 M in toluene) in MTBE (50 mL) was added dropwise a solution of P-2 (15.00 g, 71.79 mmol) in MTBE (30 mL) over 30 minutes at 40° C. The resulting reaction mixture was stirred at 40° C. for 2 hours, then cooled to room temperature and quenched by the addition of methanol (5 ml). After stirring 10 minutes, HCl (2.0 M, 8 mL) was added, and the solution was stirred for 10 minutes. The organic layer was separated and the aqueous layer was extracted with ether (3×80 mL). The combined organic phases were washed with water, brine, dried over MgSO$_4$, filtered and concentrated to afford sticky oil product P-3 which was used in the next step without further purification.

Step C: To a mixture of compound P-3 (15.14 g, 71.92 mmol), t-butyl amine (52.63 g, 719.2 mmol), and MeOH (15 mL) was added sodium hydroxide (3.16 g, 71.92 mmol) in one portion. The mixture was heated at 60° C. for 18 hours in a sealed vessel. After cooling to room temperature, the mixture was concentrated and the resulting residue was partitioned between water (50 mL) and ethyl acetate (100 mL). The organic layer was separated and the aqueous layer was extracted with ethyl acetate (3×100 mL). The combined organic phases were washed with brine, dried over MgSO$_4$, filtered and concentrated. The resulting residue was then recrystallized from heptane (30 mL) to afford compound P-4 (m/z (ES) (M+H)$^+$=248).

Step D: To a mixture of compound P-4 (15.3 g, 61.88 mmol), K$_2$CO$_3$ (25.66 g, 185.6 mmol), 4-bromo butyl nitrile (73.26 g, 495 mmol) and acetonitrile (60 mL) was heated in an oil bath at 115° C. for 15 hours in a sealed vessel. The resulting solid was filtered and washed with acetonitrile (60 mL). The filtrate was concentrated to give a residue, which was purified by MPLC (65M, 0 to 25% ethyl acetate in hexanes) to afford compound P-5 (Rf=0.2 by ethyl acetate: hexanes=1:4, m/z (ES) (M+H)$^+$=315).

Step E: A solution of compound P-5 (10.75 g, 34.20 mmol) and anhydrous THF (100 mL) was cooled to −15° C. (dry ice in acetonitrile bath) and diethylphosphoryl chloride (5.96 g, 34.54 mmol) was added. Then a solution of LiHMDS in THF (1M, 102.6 mL) was added dropwise over 30 minutes. The reaction temperature was controlled at −15° C. during the addition and the mixture was stirred further at this temperature for 2 hours. The reaction was quenched by adding water (50 mL). The organic layer was separated and the aqueous layer was extracted with ether (3×150 mL). The combined organic phases were washed with water, brine, dried over MgSO$_4$, filtered and concentrated to afford compound P-6 (m/z (ES) (M+H)$^+$=297) which was used in the next step without further purification.

Step F: A mixture of compound P-6 (34.20 mmol), 50% sodium hydroxide (7.87 g in 8.4 mL H$_2$O, 342 mmol) and ethanol (80 mL) was heated to reflux for 15 hours. After cooling to room temperature, the mixture was neutralized with HCl (conc, ~16 mL) to pH=6-7 and diluted with ethanol (50 mL). The resulting solid was filtered and washed with ethanol (3×10 mL). The filtrated was concentrated and the resulting residue compound P-7 (m/z (ES) (M+H)$^+$=315) was used in the next step without further purification.

Step G: A mixture of compound P-7 (34.20 mmol) and HCl/methanol solution (freshly prepared by adding 33 mL acetyl chloride into ice cold methanol 100 mL) was heated in an oil bath of 100° C. for 5 hours in a sealed vessel. After cooling to room temperature, the mixture was concentrated and the resulting residue was partitioned between ethyl acetate (100 mL) and NaHCO$_3$ (sat, 50 mL). The organic layer was separated and the aqueous layer was extracted with ethyl acetate (3×100 mL). The combined organic phases were washed with water, brine, dried over MgSO$_4$, filtered and concentrated. The resulting residue was purified by MPLC (65M, 0 to 40% ethyl acetate in hexanes) to afford product P-8 (Rf=0.3 by ethyl acetate:hexanes=2:3, m/z (ES) (M+H)$^+$=330).

Step H: A sealed vessel was charged with P-8 (1.94 g, 5.89 mmol) and HCl (Conc., 20 mL), flushed with nitrogen and heated in an oil bath of 100° C. for 2 hours. The mixture was concentrated and the resulting residue was dried by co-evaporation with toluene three times and put under high vacuum for 18 hours to afford the HCl salt of compound P-9 (m/z (ES) (M+H)$^+$=316).

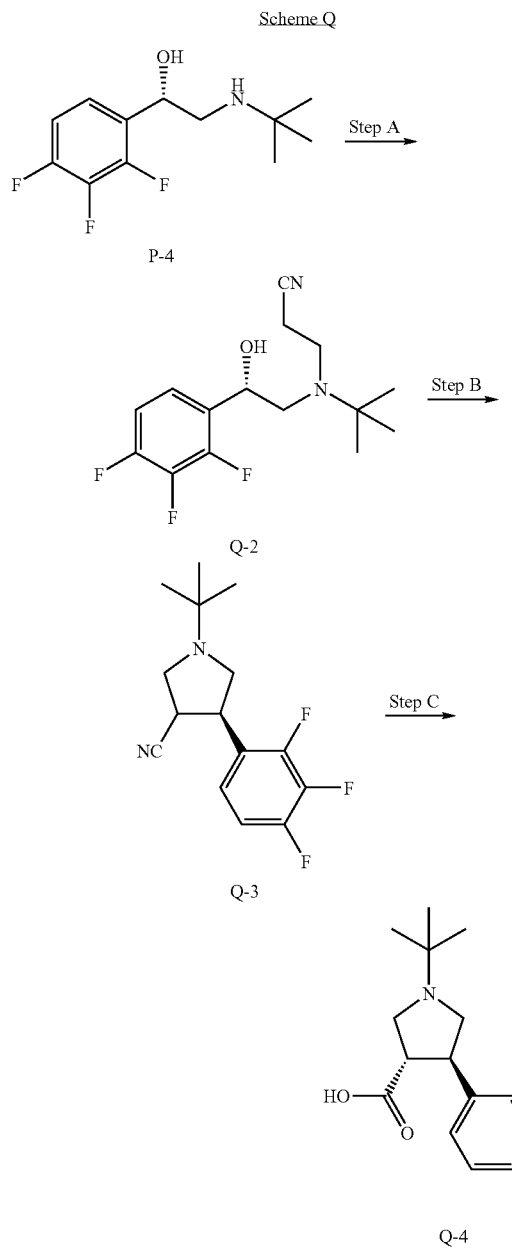

Preparation of Intermediate Q-4 (3S,4R)—N-t-butyl-4-(2',3',4'-trifluorophenyl)pyrrolidine-3-carboxylic Acid Step A: A solution of compound P-4 (0.560 g, 2.26 mmol) and acrylonitrile (1.20 g, 22.6 mmol) was heated in the sealed tube at 80° C. for 48 hours. The reaction mixture was concentrated to afford compound Q-2 (m/z (ES) (M+H)$^+$=301) which was used in the next step without further purification.

Step B: A mixture of compound Q-2 (0.632 g, 2.10 mmol) and anhydrous THF (6 mL) was cooled to −15° C. and diethylphosphoryl chloride (0.381 g, 2.21 mmol) was added, followed by addition of a solution of LiHMDS in THF (1M, 4.63 mL) over 30 minutes. The reaction temperature was controlled at −15° C. and the mixture was stirred at this temperature for 2 hours. The reaction was quenched by adding water (5 mL). The organic layer was separated and the aqueous layer was extracted with ether (3×15 mL). The combined organic phases were washed with water, brine, dried over MgSO$_4$, filtered and concentrated to afford compound Q-3 (m/z (ES) (M+H)$^+$=283) which was used in the next step without further purification.

Step C: A mixture of compound Q-3 (0.600 g, 2.10 mmol), ethanol (3 mL), and 50% NaOH (0.399 g in 0.4 m/L H$_2$O) was heated to reflux for 15 hours. The reaction mixture was neutralized by adding concentrated H$_2$SO$_4$ until pH=6.9. The resulting solid was filtered and washed with ethanol. The filtrate was concentrated and the resulting residue was dissolved in ethyl acetate (20 mL) and stirred for 10 minutes. The insoluable salt was filtered and washed with ethyl acetate (10 mL), then the filtrate was concentrated again to afford compound Q-4 (m/z (ES) (M+H)$^+$=302).

Preparation of Intermediate R-1 (3S,4R)—N-t-butyl-4-(2,4-difluorophenyl)pyrrolidine-3-carboxylic Acid

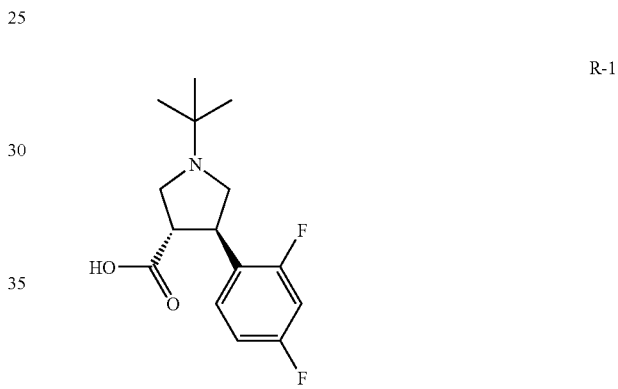

Intermediate R-1 was prepared using a synthetic procedure analogous to the procedure in Scheme Q using the difluorophenyl analog of P-4.

Scheme S

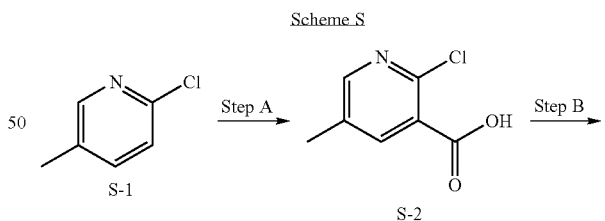

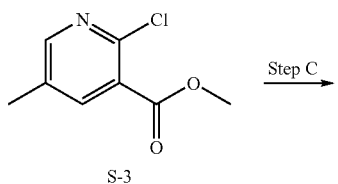

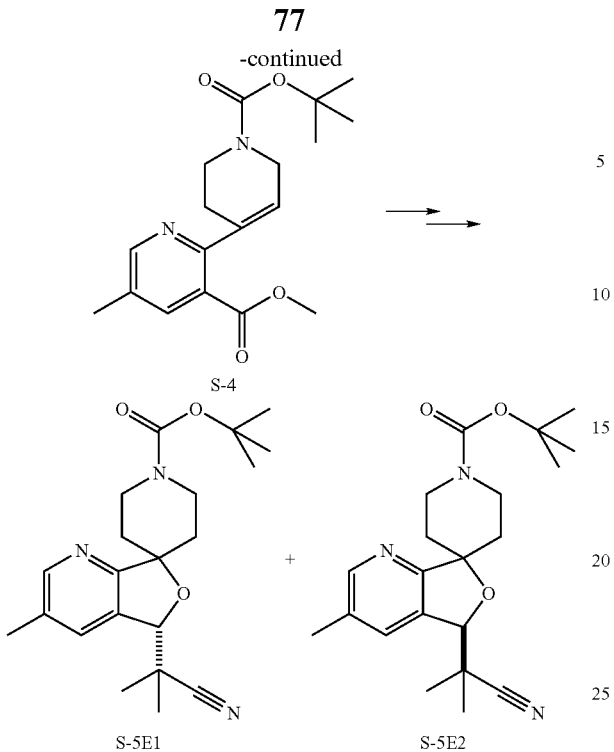

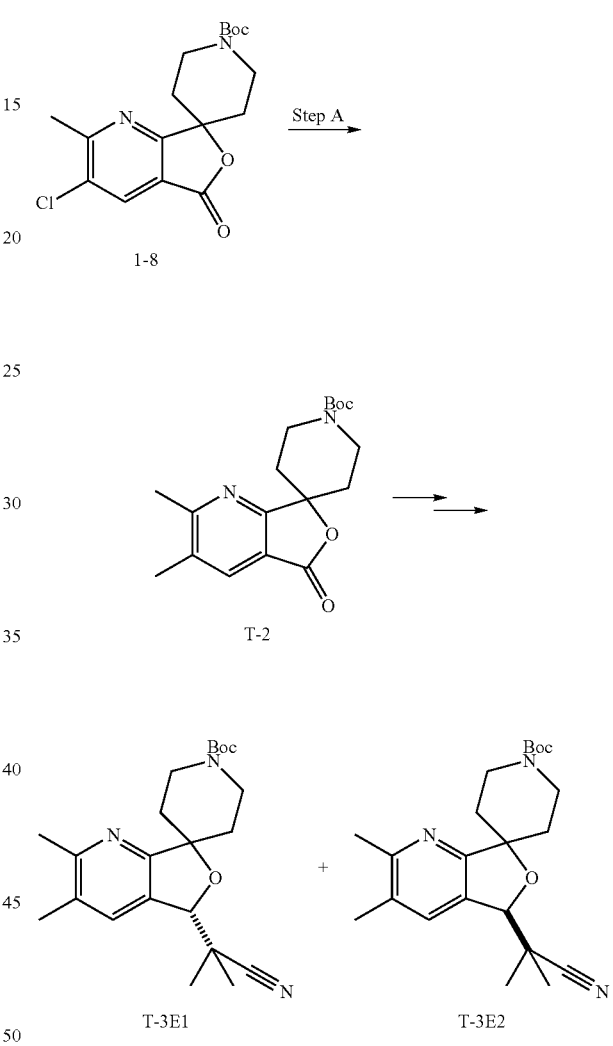

organic phases were washed with water, brine, dried over Na$_2$SO$_4$, filtered and concentrated. The resulting residue was purified by column chromatography (0% to 20% ethyl acetate in hexanes) to afford compound S-4 (m/z (ES) (M+H)$^+$=333).

Following a procedure analogous to the procedure in EXAMPLE 1 below, S-4 was converted to S-5 and the two enantiomers were separated to give compounds S-5E1 and S-5E2.

Step A: 2,2,6,6-Tetramethylpiperidine (88 mL, 0.52 mol) was added into a cooled (−78° C.) solution of n-BuLi (188 mL, 2.5 M in hexane, 0.47 mol) in anhydrous THF (1 L), and the solution was stirred for 30 minutes. Compound S-1 (60 g, 0.47 mol) was added in portions and the mixture stirred at −78° C. for 2.5 hours. The reaction solution was poured onto dry ice and was allowed to warm to r.t. The reaction mixture was extracted with water and the aqueous layer was acidified to pH~34 with 2 N HCl. The product was extracted with ether (3×1 L). The combined organic phases were washed with water (250 mL) and brine (250 mL), then dried over MgSO$_4$, filtered and concentrated under reduced pressure to afford compound S-2 ($^1$HNMR (CD$_3$OD), δ: 8.31 ppm (1H); 8.10 ppm (1H); 3.71 ppm (1H); 2.35 ppm (3H)).

Step B: To the cooled (0° C.) solution of compound S-2 (4.3 g, 25 mmol) in MeOH (75 mL) was added dropwise concentrated sulfuric acid (5 mL). The resulting reaction mixture was heated to reflux for 3 hours. After cooling to room temperature, the mixture was concentrated and the resulting residue was partitioned between CH$_2$Cl$_2$ (100 mL) and water (50 mL). The aqueous phase was neutralized to pH 7 with NaHCO$_3$. The organic layer was separated and the aqueous layer was extracted with CH$_2$Cl$_2$ (3×40 mL). The combined organic phases were washed with water, brine, dried over MgSO$_4$, filtered and concentrated to afford the compound S-3 (m/z (ES) (M+H)$^+$=186), which was used in the next step without further purification.

Step C: A mixture of compound S-3 (10 g, 54 mmol), tert-butyl 4-(4,4,5,5-tetramethyl-1,2,3-dioxaborolan-2-yl)-3,6-dihydropyridine-1(2H)-carboxylate (17 g, 55 mmol), Na$_2$CO$_3$ (17.2 g, 162 mmol), water (50 mL) and DMF (150 mL) was degassed for 15 minutes and then flushed with nitrogen. Then PdCl$_2$(dppf) (1.38 g, 1.9 mmol) was added and the reaction mixture was heated at 80° C. for 15 hours. After cooling to room temperature, the mixture was partitioned between ethyl acetate (250 mL) and water (200 mL). The organic layer was separated and the aqueous layer was extracted with ethyl acetate (3×100 mL). The combined Step A: To a mixture of compound 1-8 (8 g, 22.7 mmol), trimethyl boroxine (7.7 mL, 27.24 mmol, 50% in THF, 1.2 eq.), K$_2$CO$_3$ (9.4 g, 68.1 mmol, 3 eq.), and dioxane (200 mL) was added Pd(PPh$_3$)$_4$ (2.36 g, 2.04 mmol). The reaction mixture was refluxed overnight, then cooled to room temperature and partitioned between ethyl acetate (300 mL) and water (100 mL). The organic layer was separated and the aqueous layer was extracted by ethyl acetate (3×100 mL). The combined organic phases were washed with water, brine, dried over MgSO$_4$, filtered and concentrated. The resulting residue was purified by column chromatography to afford the product T-2 (m/z (ES) (M+H)$^+$=333).

Following a procedure analogous to the procedure in EXAMPLE 1 below, T-2 was converted to T-3 and the two enantiomers were separated to give compounds T-3 E1 and T-3 E2.

Scheme U

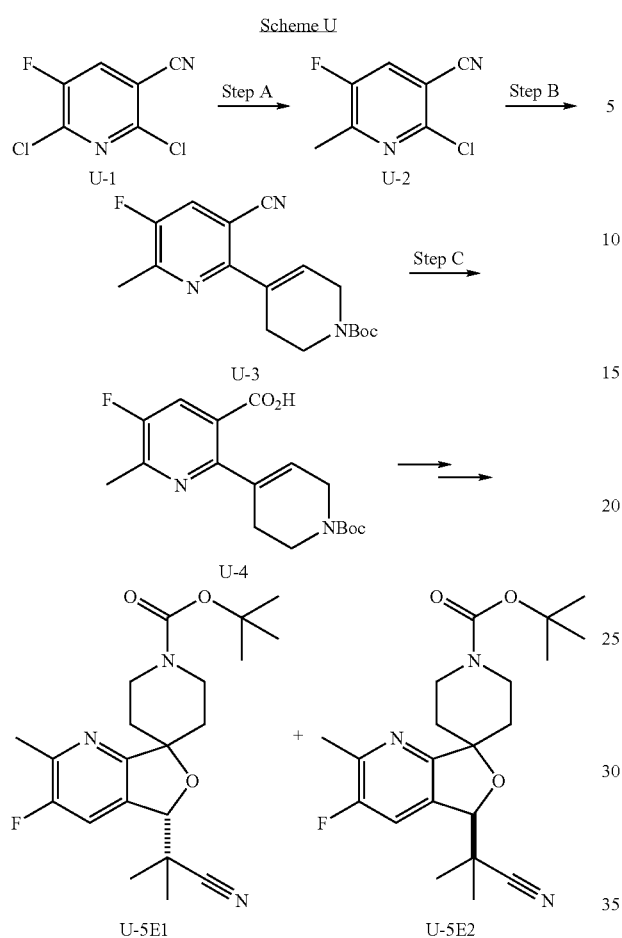

Step A: To a mixture of compound U-1 (10 g, 52.6 mmol), MeB(OH)$_2$ (3.16 g, 52.6 mmol), Na$_2$CO$_3$ (16.8 g, 158 mmol), and PdCl$_2$dppf (1.9 g, 2.64 mmol) were added dropwise H$_2$O (40 mL) and DMF (80 mL). The reaction mixture was heated to 80° C. for 3 hours, then filtered through a thin layer of Celite® and washed with ethyl acetate (200 mL). The filtrate was partitioned between H$_2$O (200 mL) and ethyl acetate (400 mL); the organic layer was separated and the aqueous layer were extracted with ethyl acetate (3×100 mL). The combined organic phases were washed with brine, dried over MgSO$_4$, filtered, concentrated. The resulting residue was purified by chromatography to afford product U-2 (m/z (ES) (M+H)$^+$= 171).

Step B: To a solution of compound U-2 (5.6 g, 33 mmol), 4-(4,4,5,5-tetramethyl-1,2,3-dioxoaborolan-2-yl)-3,6-dihydropyridine tert-butyl-1(2H)-carboxylate (12.2 g, 40 mmol), Na$_2$CO$_3$ (10.5 g, 99 mmol) and PdCl$_2$dppf (1.2 g, 1.65 mmol) was added dropwise H$_2$O (50 mL) and DMF (100 mL). The mixture was heated to 8° C. in an oil bath overnight, then filtered, and H$_2$O (200 mL) and ethyl acetate (400 mL) were added. The organic layer was separated, and the aqueous layer was extracted with ethyl acetate (3×100 mL). The combined organic phases were washed with brine, dried over MgSO$_4$, filtered and concentrated. The resulting crude product was purified by column chromatography to afford compound U-3 (m/z (ES) (M+H)$^+$=318).

Step C: A mixture of compound U-3 and concentrated HCl in a sealed vessel was heated in an oil bath of 100° C. for 15 hours. The mixture was then washed by acetonitrile (50 mL) and concentrated to give a residue. The residue was dissolved in dioxane (25 mL) and NaOH (5N, 10 mL), and (Boc)$_2$O was added in one portion. The resulting reaction mixture was stirred at room temperature for 30 minutes, then diluted with ethyl acetate (25 mL). The mixture was acidified to pH=3 with concentrated HCl. The organic layer was separated and the aqueous layer was extracted by ethyl acetate (3×20 mL). The combined organic phases were washed with brine, dried over MgSO$_4$, filtered and concentrated to afford crude product U-4 (m/z (ES) (M+H)$^+$=337) which was used directly in the next step without further purification. Following a procedure analogous to the procedure in EXAMPLE 1 below, U-4 was converted to U-5 and the two enantiomers were separated to give compounds U-5E1 and U-5E2.

Scheme V

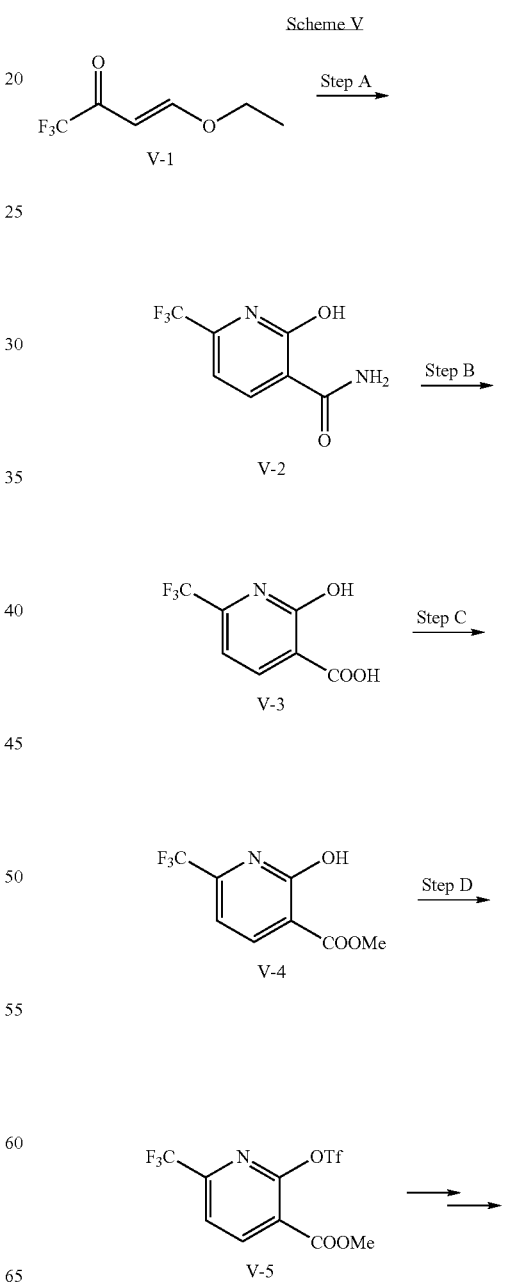

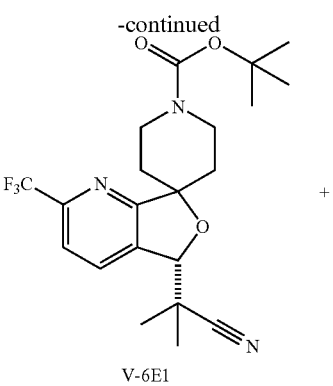

V-6E1

+

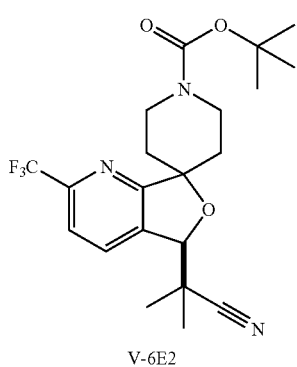

V-6E2

Step A: To a solution of anyhydrous methanol (50 mL), sodium methoxide/methanol solution (61.47 mmol) and malonamide (4.50 g, 44.08 mmol) was added (E)-4-ethoxy-1,1,1-trifluoro-3-butene-2-one V-1 (7.781 g, 46.28 mmol) and the mixture was heated to reflux for 2 hours. When the reaction was quenched by addition of water and the aqueous layer pH was adjusted to pH 1-3 with HCl. The mixture was concentrated to give compound V-2 (m/z (ES) (M+H)$^+$=207), which was used in the next step without further purification.

Step B: A mixture of compound V-2 (5.87 g, 28.48 mmol) and concentrated HCl (50 mL) was heated to 103° C. for 2 hours, then concentrated and the resulting residue V-3 (m/z (ES) (M+H)$^+$=208) was used in the next step without further purification.

Step C: A solution of compound V-3 (5.89 g, 28.44 mmol) in MeOH (60 mL) was cooled in an ice bath, then $H_2SO_4$ (Conc., 5 mL) was added dropwise over 5 minutes. The resulting reaction mixture was heated at 70° C. for 15 hours, then the solvent was removed and the resulting residue was partitioned between water (100 mL) and ethyl acetate (200 mL). The organic layer was separated and aqueous layer was extracted with ethyl acetate (3×100 mL). The combined organic phases were washed with water, brine, dried over $MgSO_4$, filtered and concentrated to give compound V-4 (m/z (ES) (M+H)$^+$=222), which was used in the next step without further purification.

Step D: A mixture of compound V-4 (5.80 g, 26.23 mmol), methylene chloride (50 mL), DMAP (0.32 g, 2.63 mmol) and triethyl amine (3.19 g, 31.47 mmol) was cooled to −78° C. Then trifluoromethanesulfonic anhydride (8.66 g, 30.69 mmol) was added dropwise over 5 minutes. The resulting reaction mixture was stirred at −78° C. for 30 min, then allowed to warm up to 0° C. and stirred for 2 hours. The reaction mixture was then poured into ice water (50 mL). The organic layer was separated and the aqueous layer was extracted with ethyl acetate (3×50 mL). The combined organic phases were washed with brine, dried over $MgSO_4$, filtered and concentrated. The resulting residue was purified by MPLC (65M, 0 to 10% ethyl acetate in hexanes) to afford product V-5 (m/z (ES) (M+H)$^+$=354).

Following a procedure analogous to the procedure in EXAMPLE 1 below, V-5 was converted to V-6 and the two enantiomers were separated to give compounds V-6E1 and V-6E2.

Scheme W

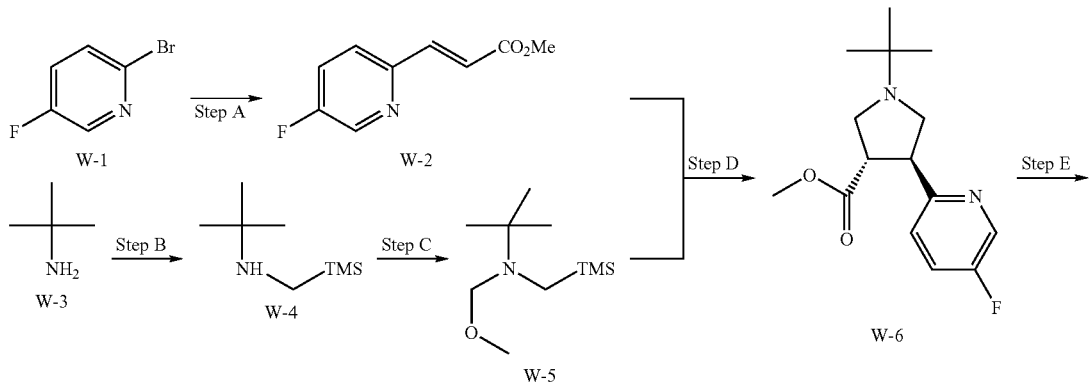

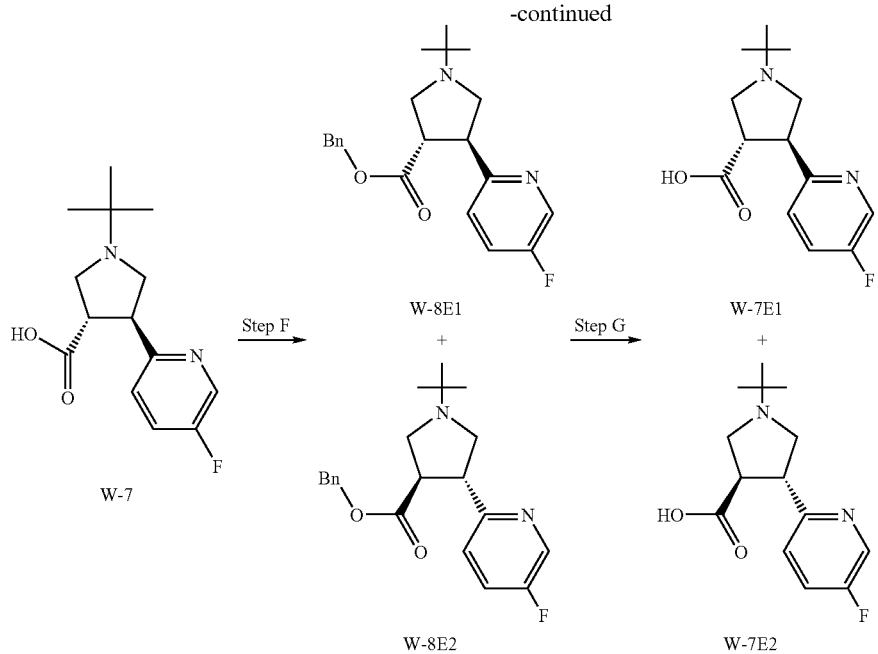

Step A: A suspension of 2-bromo-5-fluoropyridine W-1 (9.0 g, 68.4 mmol), Pd(dppf)Cl$_2$ (5 g, 6.84 mmol), tetrabutylammonium iodide (30 g, 82 mmol) and K$_2$CO$_3$ (28 g, 205 mmol) in N,N-dimethylformide (130 mL) was degassed via three vacuum/nitrogen ingress cycles, and then methyl acrylate (17.6 g, 205 mmol) was added. The mixture was stirred at 100° C. overnight, then water was added and the aqueous layer was extracted with Et$_2$O (3×100 ml). The combined organic phases were washed with brine, dried over MgSO$_4$, filtered and concentrated. The resulting residue was purified by column chromatography (0% to 5% ethyl acetate in hexanes) to afford the product W-2.

Step B: To a solution of t-butylamine W-3 (100 g, 1.36 mol) in DMSO (60 mL) was added chloromethylsilane (83.8 g, 0.68 mol). The mixture was refluxed at 100° C. overnight, and then quenched with water. The aqueous layer was extracted with Et$_2$O (3×100 ml), and the combined organic phases were washed with 1% Na$_2$CO$_3$, dried over MgSO$_4$, filtered and concentrated. The resulting residue was distilled at 130~135° C. under normal pressure to obtain W-4 as a colorless liquid.

Step C: To a 0° C. solution of 37% aqueous formaldehyde (7.2 g, 88.7 mmol) (adjusted pH~8 with 10% aqueous NaOH) was added dropwise W-4 (10 g, 62.9 mmol). After stirring for 10 min at 0° C., 7.4 mL of methanol was added in one portion. Potassium carbonate (4.9 g) was added to the mixture to absorb the aqueous phase. The mixture was stirred at 0° C. for 1 hr, then the aqueous phase was decanted, and an additional 2.5 g of potassium carbonate were added. The mixture was stirred at room temperature overnight. Ether was added to the mixture and the solution was dried over potassium carbonate, filtered, and concentrated at 10° C. under reduced pressure. The residue was distilled at reduced pressure (~20 nm Hg) to give W-5.

Step D: To a solution of W-2 (0.6 g, 3.33 mmol) and W-5 (2.03 g 9.99 mmol) in dichloromethane (20 mL) was added dropwise TFA (2.2 g, 19 mmol). The mixture was warmed up to 80° C. and stirred overnight. After cooling to room temperature, the solvents were removed under reduced pressure. The resulting residue was quenched with saturated NaHCO$_3$, and the aqueous layer was extracted with EtOAc (3×50 mL). The combined organic phases were washed with brine, dried over MgSO$_4$, filtered and concentrated. The resulting residue was purified by column chromatography (0% to 4% methanol in dichloromethane) to afford the product W-6.

Step E: The compound W-6 (3.0 g, 10.7 mmol) was treated in THF—H$_2$O (1:1, 10.6 mL) with LiOH.H$_2$O (1.35 g, 32.1 mmol) at ambient temperature for 6 h. The mixture was then concentrated to remove tetrahydrofuran, and the aqueous layer was extracted with dichloromethane (2×). The aqueous layer was acidified with 1M HCl to pH~4 and extracted with EtOAc (4×). The combined organic phases were washed with brine, dried over MgSO$_4$, filtered and concentrated to obtain W-7,1-tert-butyl-4-(5-fluoropyridin-2-yl)pyrrolidine-3-carboxylic acid. $^1$HNMR (400 MHz, MeOD, ppm) δ: 8.35-8.36 (d, J=3.2 Hz, 1H), 7.43-7.51 (m, 2H), 3.81-3.84 (m, 1H), 3.47-3.55 (m, 2H), 3.27-3.36 (m, 2H), 3.14-3.17 (m, 1H), 1.43 (s, 9H).

Step F: A suspension of W-7 (4.0 g, 15.0 mmol) and NaOH (0.9 g, 15.1 mmol) in N,N-dimethylformide (100 mL) was stirred for 10 min, and then benzyl bromide (3.56 mL, 30 mmol) was added. The mixture was stirred for 15 h, then diluted with EtOAc and washed with water (3×). The organic layer was washed with brine, dried and concentrated to obtain trans racemic mixture, which were separated by chiral HPLC to afford W-8E1 and W-8E2. $^1$HNMR (400 MHz, CDCl$_3$, ppm) δ: 8.38-8.39 (d, J=4.0 Hz, 1H), 7.17-7.32 (m, 7H), 5.07-45.09 (q, 2H), 3.74-3.77 (q, 1H), 3.44-3.46 (q, 1H), 3.13-3.20 (m, 3H), 2.85-2.88 (m, 1H), 1.10 (s, 9H).

Step G: Compound W-8E1 (0.9 g, 2.53 mmol) in THF (20 mL) was hydrogenated at normal pressure at room temperature with palladium-on-charcoal (0.1 g) catalyst. After stirring overnight, the catalyst was filtered off and the filtrate was evaporated to afford the target compound W-7E1. $^1$HNMR (400 MHz, MeOD, ppm) δ: 8.44-8.45 (d, J=3.6 Hz, 1H), 7.48-7.55 (m, 2H), 3.90-4.00 (q, 1H), 3.62-3.77 (m, 4H), 3.18-3.20 (q, 1H), 1.43 (s, 9H).

W-7E2 was prepared using the same procedure as for W-7E1.

Scheme X
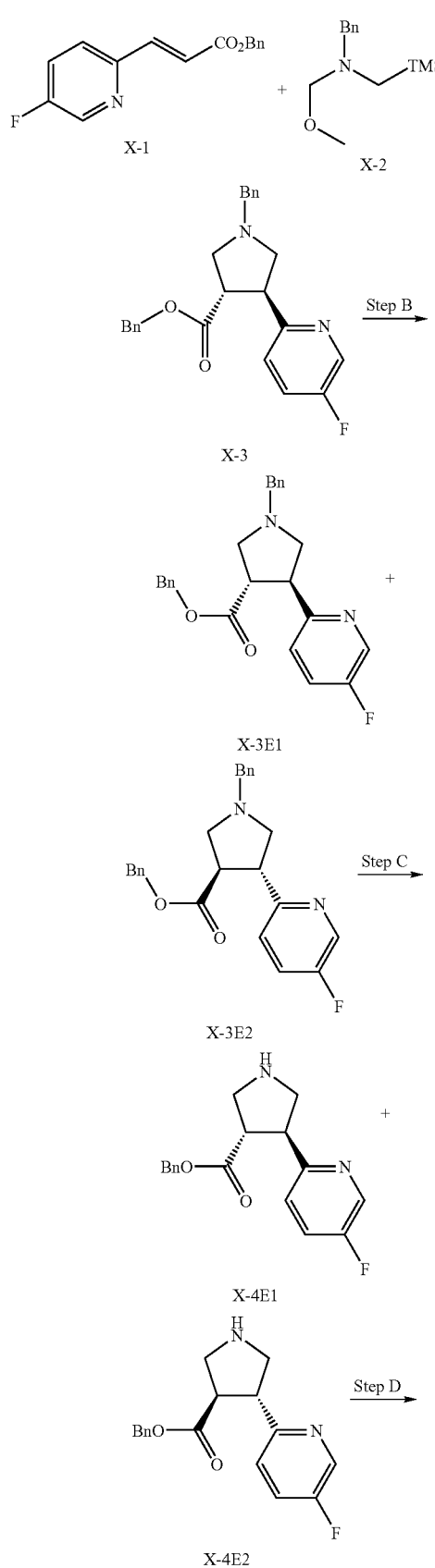
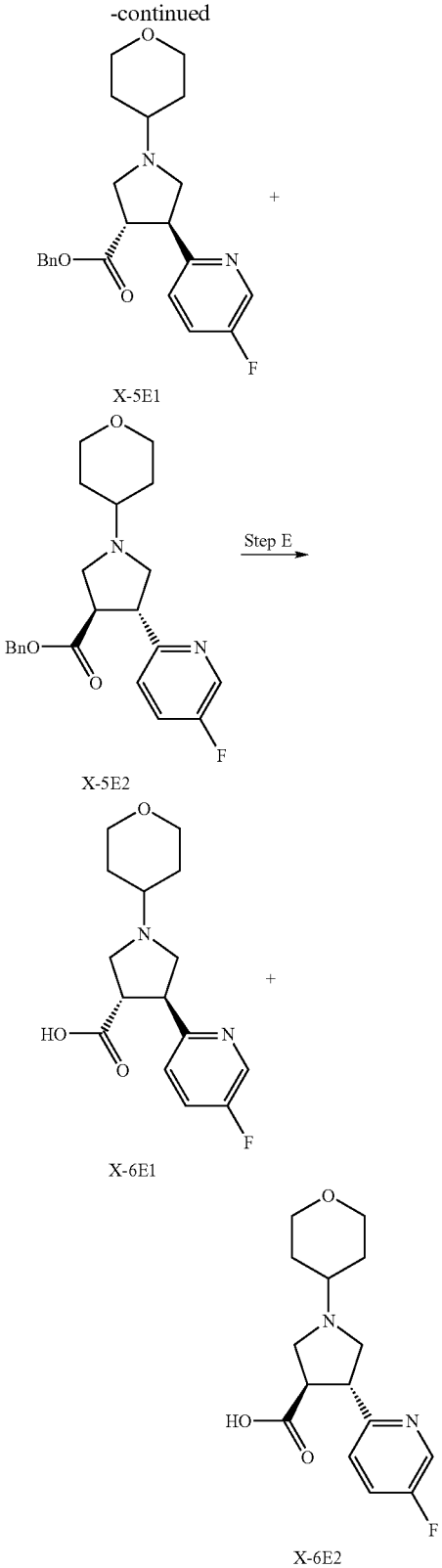
Step A: To a solution of X-1 (3.3 g, 12.8 mmol, prepared using a procedure analogous to the procedure to make W-2) and X-2 (6.08 g, 25.9 mmol prepared using a procedure analogous to the procedure to make W-5) in DCM (200 mL) was added dropwise TFA (13.1 g, 115.2 mmol). The mixture stirred in a sealed tube at 80° C. overnight. After cooling to room temperature, solvents were removed under reduced pressure. The residue was quenched with saturated NaHCO$_3$, and the aqueous layer was extracted with EtOAc (3×). The combined organic phases were washed with brine, dried over MgSO$_4$, filtered and concentrated. The resulting residue was purified by column chromatography (0% to 4% methanol in DCM) to afford the product X-3 (m/z (ES) (M+H)$^+$=391) as a racemic mixture.

Step B: The racemic mixture of product X-3 from Step A was separated into two single enantiomers by Chiral AD column using 30% ethanol in hexane to afford X-3 E1 (RT=15.8 min on chiral AD-H column using 30% ethanol in hexane) and X-3 E2 (RT=18.0 min on chiral AD-H column using 30% ethanol in hexane).

Step C: To a 25 mL one neck round bottom flask was charged X-3 E1 (300 mg, 0.768 mmol) and 1,2-dichloroethane (3 mL). Then 1-chloroethyl chloroformate (220 mg, 1.537 mmol) was added and the resulting mixture was heated to 90° C. for 6 hours. After cooling to room temperature, methanol (2 mL) was added and the resulting mixture was heated to 85° C. for 30 min. Then the mixture was concentrated and co-evaporated with toluene three times to afford product X-4E1 (m/z (ES) (M+H)$^+$=301) which was used directly to next step without further purification.

Using the same procedure as in Step C, X-4E2 (m/z (ES) (M+H)$^+$=301) was prepared.

Step D: To a 25 mL one necked round bottomed flask was charged X-4E1 (0.231 g, 0.769 mmol), tetrahydro-4-pyranone (0.385 g, 3.846 mmol), methylene chloride (6 mL), molecular sieve 4A (1 g). Then sodium triacetoxyborohydride (1.304 g, 6.153 mmol) was added and the mixture was stirred at room temperature for 72 hours. The mixture was then filtered through a thin layer of celite and washed with ethyl acetate (4×5 mL). The filtrate was then washed with water, dried over MgSO$_4$, filtered and concentrated. The resulting residue was purified by MPLC (40 g silica gel, 0 to 50% ethyl acetate in hexanes and then 5% MeOH in CH$_2$Cl$_2$) to afford product X-5E1 as an oil (m/z (ES) (M+H)$^+$=385). Using the same procedure as in Step D, X-5E2 (m/z (ES) (M+H)$^+$=385) was prepared.

Step E: A 25 mL round bottom flask was charged with X-5E1 (0.211 g, 0.549 mol), EtOAc (4 mL) and Pd/C (10%, 60 mg). The system was vacuumed and refilled with hydrogen four times and then the reaction mixture was stirred under a hydrogen atmosphere for 15 hours over night. The mixture was then filtered through a thin layer of celite and washed with ethyl acetate (3×4 mL), and concentrated to afford product X-5E1 (m/z (ES) (M+H)$^+$=295).

Using the same procedure as in Step E, X-6E2 (m/z (ES) (M+H)$^+$—295) was prepared.

Scheme Y

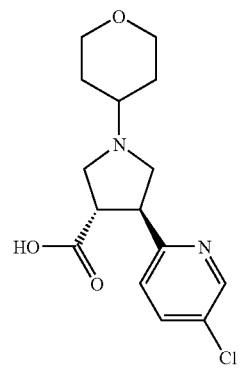

Y-1E1

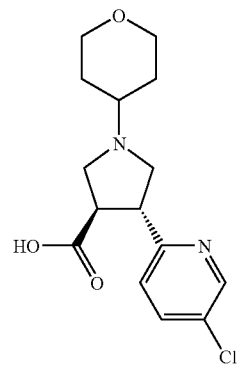

Y-1E2

Intermediate Y-1E1 and Y-1E2 were prepared using a synthetic procedure analogous to the procedure in Scheme X using the 5-chloro-2-bromopyridine analog of W-1.

Example 1

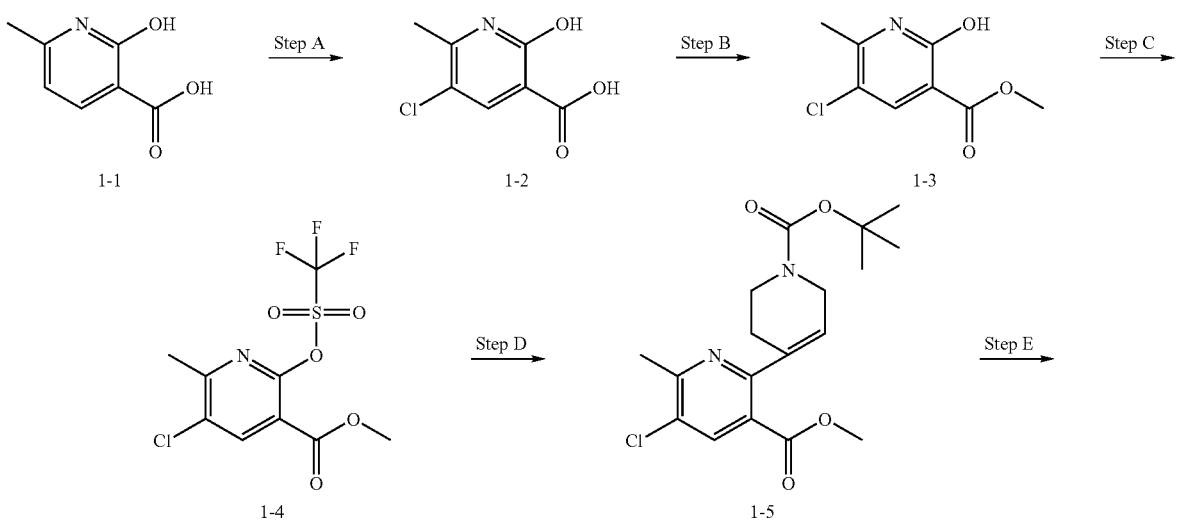

-continued
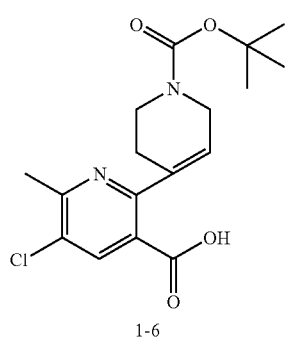 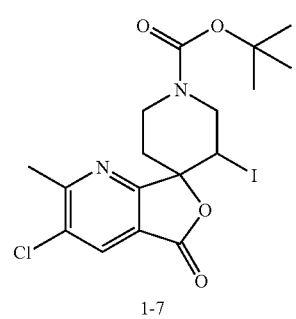 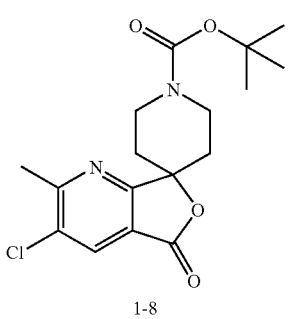
1-6 → Step F → 1-7 → Step G → 1-8
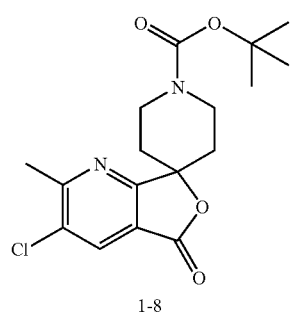 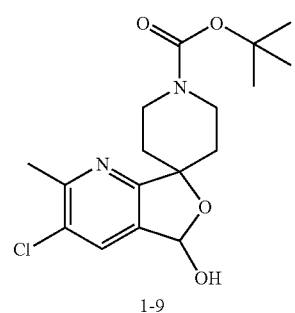
1-8 → Step H → 1-9 → Step I →
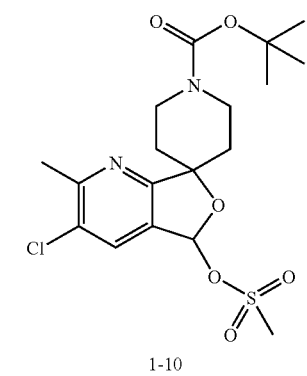 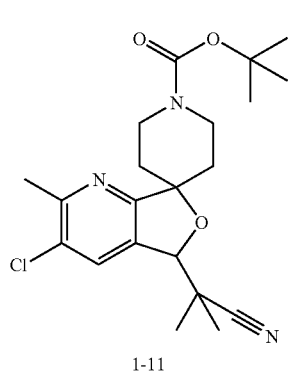
1-10 → Step J → 1-11 → Step K →
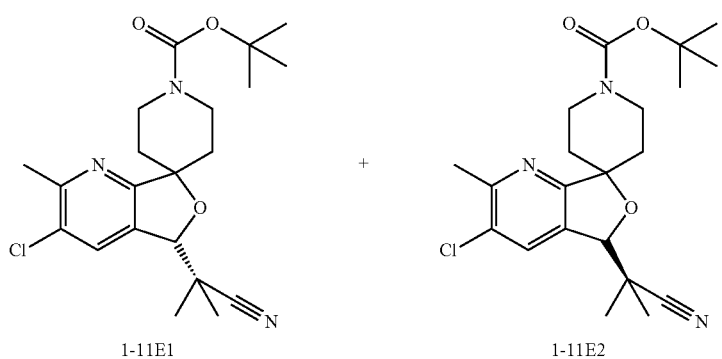
1-11E1 + 1-11E2

-continued
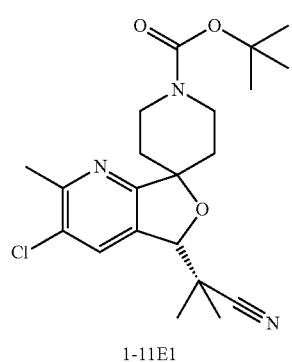
1-11E1
Step L
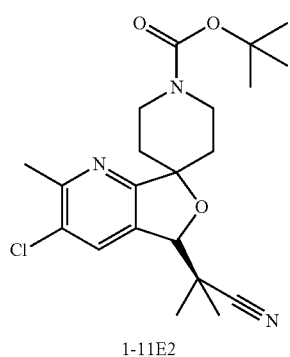
1-11E2
Step N
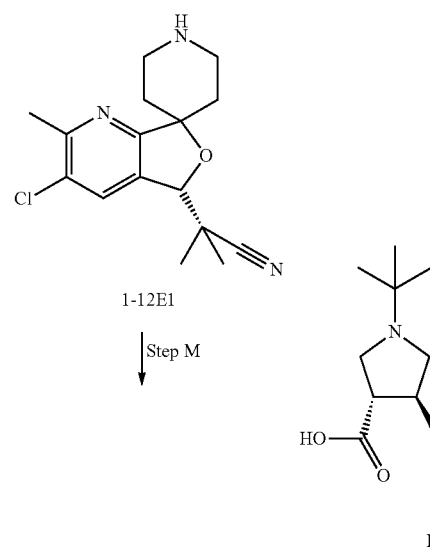
1-12E1
Step M
R-1
1-12E2
Step O
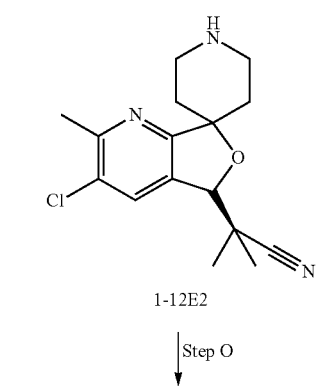
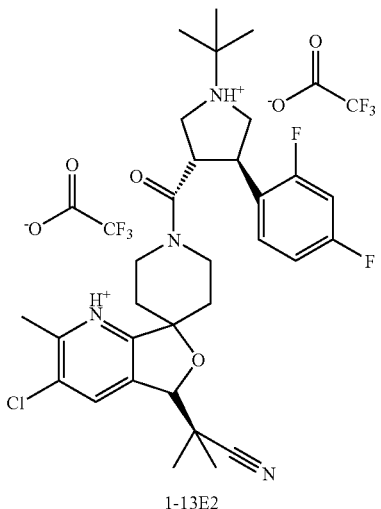
1-13E1
1-13E2

Step A: A solution of NaOCl (1.2 L, of 5%) was cooled to 0° C. in ice bath. 2-hydroxy-6-methylpyridine-3-carboxylic acid 1-1 (100 g, 0.65 mol) was added in small portions. The resulting homogenous mixture was stirred at 0° C. for 1 hour and then at 10° C. for 5 hours. Another portion NaOCl (300 mL, of 5%) was added at 0° C. and the mixture was stirred at 10° C. overnight. The solution was acidified to pH=1 with 12N HCl, and the resulting solid was filtered, washed with water, and oven dried to afford white solid product 1-2 (m/z (ES) (M+H)$^+$=188).

Step B: To a solution of compound 1-2 (9.9 g, 53 mmol) in MeOH (150 mL) was added dropwise sulfuric acid (10 mL) over 5 min. The resulting reaction mixture was heated to reflux for 3 hours. After cooling to room temperature, the mixture was concentrated to give a residue, which was partitioned between $CH_2Cl_2$ (200 mL) and water (100 mL). $NaHCO_3$ was added until the aqueous layer was neutral (pH=7). The layers were separated and the aqueous layer was extracted with $CH_2Cl_2$ (3×100 mL). The combined organic phases were washed with water, brine, dried over $MgSO_4$, filtered and concentrated to afford white solid product 1-3 (m/z (ES) (M+H)$^+$=202) which was used in next step without further purification.

Step C: A mixture of methyl 5-chloro-2-hydroxy-6-methylpyridine-3-carboxylate 1-3 (10.32 g, 51.2 mmol), methylene chloride (50 mL), DMAP (0.625 g, 5.12 mmol) and triethyl amine (6.21 g, 614 mmol) was cooled to −78° C. Then trifluoromethanesulfonic anhydride (16.90 g, 59.89 mmol) was added dropwise over 5 min. The resulting reaction mixture was stirred at −78° C. for 30 minutes, then allowed to warm up to 0° C. and stirred for 2 hours. The reaction mixture was poured into ice water (50 mL). The resulting organic layer was separated and the aqueous layer was extracted by ethyl acetate (3×50 mL). The combined organic phases were washed with brine, dried over $MgSO_4$, filtered and concentrated. The resulting residue was purified by MPLC (65M, 0 to 10% ethyl acetate in hexanes) to afford white solid product 1-4 (m/z (ES) (M+H)$^+$=334).

Step D: To a mixture of compound C-4 (13.9 g, 41.7 mmol), tert-butyl 4-(4,4,5,5-tetramethyl-1,2,3-dioxaborolan-2-yl)-3,6-dihydropyridine-1(2H)-carboxylate (13.6 g, 44 mmol, prepared as described in Rohr, M; etc. *Heterocycles* 1996, 43, 2131), sodium carbonate (13.25 g, 0.125 mol), $H_2O$ (40 mL) and DMF (120 mL) was added $PdCl_2$(dppf) (1.07 g, 1.46 mmol). The reaction mixture was heated at 80° C. for 15 hours, then cooled to room temperature and partitioned between ethyl acetate (200 mL) and water (100 mL). The organic layer was separated and the aqueous layer was extracted with ethyl acetate (3×100 mL). The combined organic phases were washed by water, brine, dried over $MgSO_4$, filtered and concentrated. The resulting residue was purified by column chromatography (0% to 20% ethyl acetate in hexanes) to afford the white solid product 1-5 (m/z (ES) (M+H)$^+$=367).

Step E: A mixture of compound 1-5 (10.9 g, 29.8 mmol), MeOH (47 mL) and NaOH (5N, 6.55 g in 31 mL $H_2O$) was heated to 60° C. for 1 hour. Then the reaction mixture was concentrated to half volume. After the mixture was acidified to pH=2 with concentrated HCl, the mixture was extracted with ethyl acetate (3×35 mL). The combined organic phases were washed with water, brine, dried over $MgSO_4$, filtered and concentrated to afford white solid product 1-6 (m/z (ES) (M+H)$^+$=353) which was used in the next step without further purification.

Step F: To a solution of compound 1-6 (4.38 g, 12.4 mmol) along with $CH_3CN$ (30 mL) and $NaHCO_3$ (sat, 150 mL) was added dropwise a solution of $I_2$ (4.09 g, 16.02 mmol) and KI (10.29 g, 62.01 mmol) in water (60 mL) over 30 min. The resulting mixture was stirred at room temperature for 18 hours, then ethyl acetate (600 mL) was added, followed by a solution of $NaS_2O_4$ (15%, 60 mL). The mixture was stirred for 20 minutes, then the organic layer was separated and the aqueous layer was extracted with ethyl acetate (3×1100 mL). The combined organic phases were washed with water, brine, dried over $MgSO_4$, filtered and concentrated to afford white solid product 1-7 (m/z (ES) (M+H)$^+$=479) which was used directly in the next step.

Step G: A mixture of compound 1-7 (5.00 g, 10.44 mmol), AIBN (0.086 g, 0.55 mmol) and toluene (40 mL) was heated to 80° C. and stirred while $Bu_3SnH$ (9.00 g, 20.9 mmol) was added dropwise. Then mixture was heated in an oil bath of 80° C. for 3 hours, then concentrated. The resulting residue was purified by MPLC (65M, 0 to 25% ethyl acetate in hexanes with 20 column volumn) to afford white solid product 1-8 (m/z ES) (M+H)$^+$=353).

Step H: A solution of compound 1-8 (3.32 g, 9.41 mmol) and toluene (10 mL) was cooled to −78 C, then a solution of DIBAL in tolene (1M, 21.64 mmol) was added dropwise over 20 minutes. The reaction mixture was stirred at −78 C for 2 hours, then quenched by addition of methanol (1 mL), followed by water (20 mL) and NaOH (5N, 6 mL). The reaction mixture was extracted with ethyl acetate (3×50 mL) and the combined organic phases were washed with brine, dried over $MgSO_4$, filtered and concentrated to white solid product 1-9 (m/z (ES) (M+H)$^+$=355).

Step I: To a mixture of 1-9 (0.402 g, 1.13 mmol), methylene chloride (5 mL) and TEA (0.344 g, 3.40 mmol) was added dropwise methanesulfonyl chloride (0.195 g, 1.70 mmol) over 1 min. The resulting reaction mixture was stirred at room temperature for 2 hours, then concentrated, dried under high vacuum and used in the next step without further purification.

Step J: A solution of THF (6 mL) was cooled to −78° C., LDA (2.0 M in THF/toluene, 4.6 mL, 10.2 mmol) was added, followed by the dropwise addition of isobutylnitrile (0.782 g, 11.32 mmol) over 5 min. The reaction mixture was stirred at −78° C. for 30 min, then a solution of 1-10 (0.490 g, 1.13 mmol) in THF (6 mL) was added dropwise over 5 min. The resulting reaction mixture was stirred at −78° C. for 1 hour, then quenched with saturated $NH_4Cl$ (5 mL). The organic layer was separated and the aqueous layer was extracted with ethyl acetate (3×). The combined organic phases were washed by water, brine, dried over $MgSO_4$, filtered and concentrated. The resulting residue was purified by MPLC (25S, 10 to 25% ethyl acetate in hexanes) to afford product 1-11 (m/z (ES) (M+H)$^+$=406).

Step K: The chiral separation of the mixture of enantiomers 1-11 to give the two individual enantiomers 1-11E1 and 1-11E2 was achieved using a preparative chiral AD column with 2% EtOH in heptane as the eluting solvent to afford 1-11E1 (10.31 min, 4% EtOH in heptane on Chiral AD-H column, m/z (ES) (M+H)$^+$=406) and 1-11E2 (31.13 min, 4% EtOh in heptane on Chiral AD-H column, m/z (ES) (M+H)$^+$=406).

Step L: A mixture of compound 1-11 E1 (0.020 g, 0.049 mmol) and HCl (Conc. 0.5 mL) in methanol (1 mL) was stirred at 40° C. for 30 min. Then the mixture was concentrated and the resulting residue was co-evaporated with toluene three times to afford compound 1-12E1 (m/z (ES) (M+H)$^+$=306).

Step M: To a mixture of compound 1-12E1 (0.049 mmol), acid R-1 (0.014 g, 0.049 mmol) and Hunig's base (0.032 g, 0.246 mmol) was added HOAT (0.007 g, 0.049 mmol) and HATU (0.026 g, 0.069 mmol). The resulting reaction mixture was stirred at room temperature for 2 hours, then concentrated and the residue was dissolved in methanol (1 mL), filtered through a syringe filtered and washed with methanol (2 mL). The filtrate was concentrated and the resulting residue was purified by RP HPLC (YMC column, 20% to 80% acetonitrile in water) to afford the TFA salt of compound 1-13E1 (m/z (ES) (M+H)$^+$=571).

Step N: Using a procedure similar to the procedure in Example 1, Step L, 1-12E2 (m/z (ES) (M+H)$^+$=306) was prepared.

Step O: Using a procedure similar to the procedure in Example 1, Step M, 1-13E2 (m/z (ES) (M+H)$^+$=571) was prepared.

Following a procedure analogous to the procedure described in Example 1 and the appropriate reagents, the following compounds were prepared:

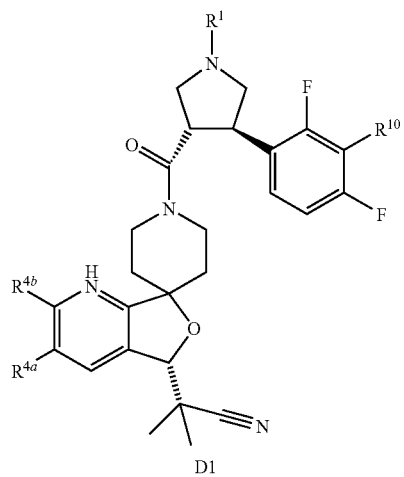

D1

+

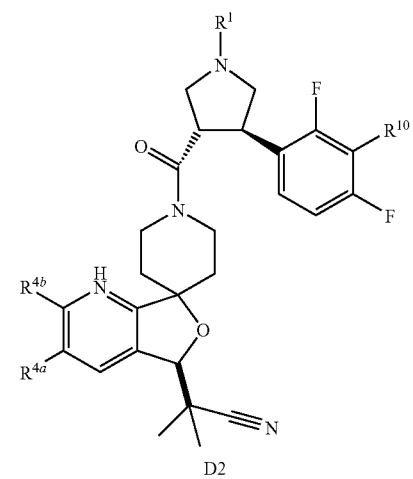

D2

| Example | R$^{4b}$ | R$^{4a}$ | R$^1$ | R$^{10}$ | D1 or D2 | Parent Ion m/z (M + H) |
|---|---|---|---|---|---|---|
| 2 | Me | Cl | t-Butyl | F | D1 | 589 |
| 3 | Me | Cl | t-Butyl | F | D2 | 589 |
| 4 | Me | Cl | 4-tetrahydro-pyranyl | H | D1 | 599 |
| 5 | Me | Cl | Hydroxy-t-butyl | H | D1 | 587 |
| 6 | CF$_3$ | H | 4-tetrahydro-pyranyl | H | D1 | 619 |
| 7 | Me | F | t-Butyl | H | D1 | 555 |
| 8 | Me | F | t-Butyl | H | D2 | 555 |
| 9 | Me | F | 4-tetrahydro-pyranyl | H | D1 | 583 |

Example 10

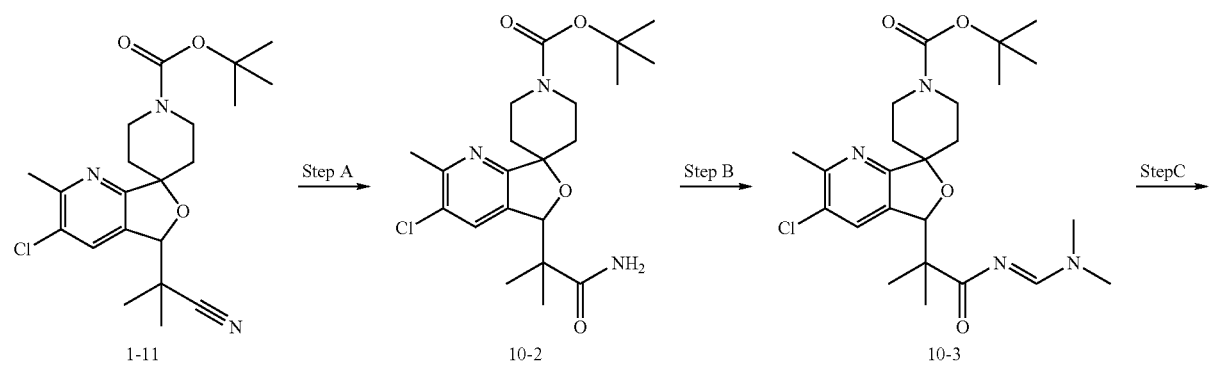

-continued
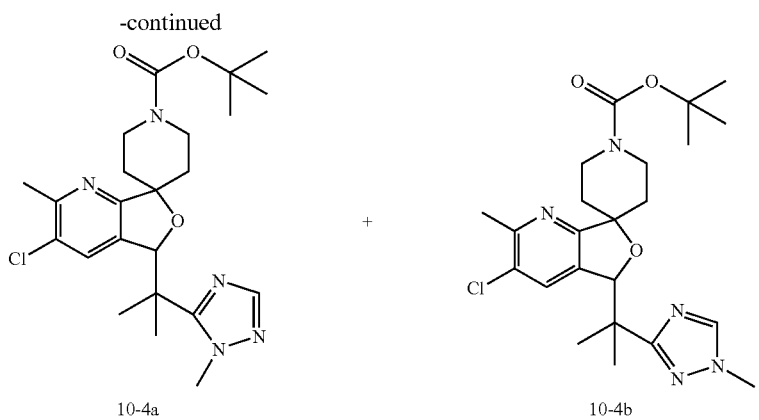
10-4a    +    10-4b
Step D
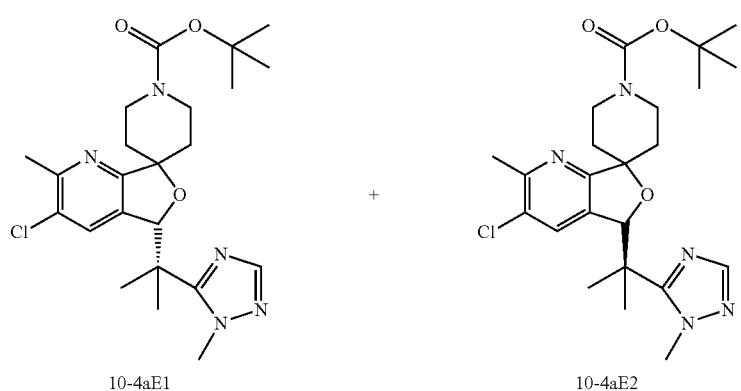
10-4aE1    +    10-4aE2
Step E    Step G
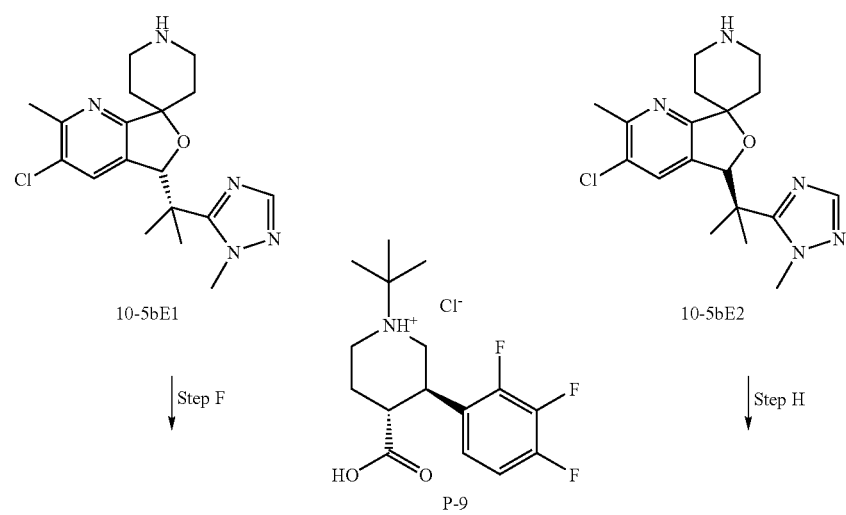
10-5bE1    P-9    10-5bE2
Step F    Step H -continued

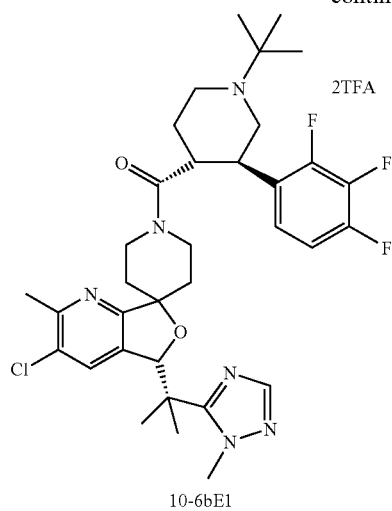

10-6bE1

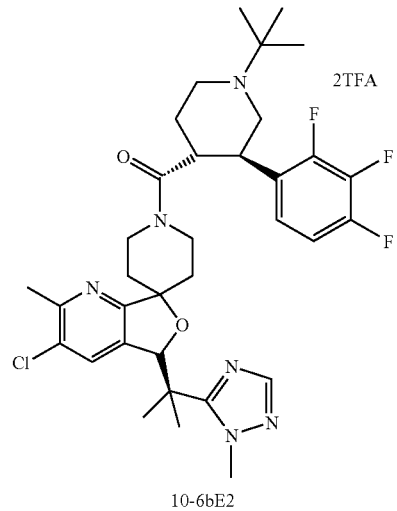

10-6bE2

Step A: A mixture of compound 1-11 (13.71 g, 33.77 mmol), potassium hydroxide (17.06 g, 304 mmol), isopropanol (170 mL) and water (17 mL) in a sealed vessel was heated in an oil bath of 85° C. for 15 hours. The mixture was then cooled to 0° C. in an ice water bath and stirred for 30 minutes. The resulting solid was filtered and washed with isopropanol (20 mL) and water (20 mL×2). The filtrate was concentrated to the water volume and the solid was filtered and washed with water (3×). The two crops of white solid was combined to afford product 10-2 (m/z (ES) (M+H)$^+$=424).

Step B: A mixture of compound 10-2 (9.10 g, 21.46 mmol) and N,N-dimethylforamide dimethyl acetal was heated in an oil bath of 120° C. for 1 hour. After cooling to room temperature, the excess DMF-DMA was removed by rotary evaporation and the residue was dried by co-evaporation with toluene three times to afford sticky oil product 10-3 (m/z (ES) (M+H)$^+$=449) which is used in the next step without further purification.

Step C: A mixture of compound 10-3 (10.28 g, 21.47 mmol) and HOAc (50 mL) was cooled to 0° C., then methyl hydrazine (1.088 g, 23.61 mmol) was added dropwise in 1 min under vigorous stirring. The resulting reaction mixture was heated to 95° C. for 1 hour. After cooling to room temperature, the solvent was removed and the resulting residue was partitioned between ethyl acetate (200 mL) and saturated NaHCO$_3$ (100 mL). The organic layer was separated and the aqueous layer was extracted with ethyl acetate (3×100 mL). The combined organic phases were washed with water, brine, dried over MgSO$_4$, filtered and concentrated. The resulting residue was then purified by MPLC (65M column, 0 to 60% ethyl acetate in hexanes) to afford compound 10-4a (Rf=0.4 by ethyl acetate:hexanes=3:2, m/z (ES) (N+H)$^+$=462) and compound 10-4b (Rf=0.15 by ethyl acetate:hexanes=3:2, m/z (ES) (M+H)$^+$=462).

Step D: The enantiomeric mixture of compound 10-4a was dissolved in 50% IPA in heptane, loaded onto ChiralPak AD column and eluted with 7% EtOH in heptane to afford two enantiomers, 10-4aE1 (RT=15.40 min by 7% EtOH in heptane on Chiral AD column, m/z (ES) (M+H)$^+$=462) and 104aE2 (RT=22.12 min by 7% EtOH in heptane on Chiral AD column, m/z (ES) (M+H)$^+$=462).

Step E: A mixture of compound 10-4aE1 (0.016 g, 0.035 mmol) and concentrated HCl (0.5 mL) in methanol (1 mL) was stirred at 40° C. for 30 min. The mixture was then concentrated and the residue was co-evaporated with toluene three times to afford compound 10-5aE1 (m/z (ES) (M+H)$^+$=362).

Step F: To a mixture of compound 10-5aE1 (0.035 mmol), acid P-9 (0.016 g, 0.045 mmol) and Hunig's base (0.022 g, 0.173 mmol) was added HOAT (0.005 g, 0.035 mmol) and HATU (0.018 g, 0.048 mmol). The resulting reaction mixture was stirred at room temperature for 2 hours, then concentrated. The resulting residue was dissolved in methanol (1 mL), filtered through a syringe and washed with methanol (2 mL). The filtrate was concentrated and the resulting residue was purified by RP HPLC (YMC column, 20% to 80% acetonitrile in water) to afford the TFA salt of compound 10-6aE1 (m/z (ES) (M+H)$^+$=659).

Step G: The similar procedure to Step E was applied for the preparation of 10-5aE2 (m/z (ES) (M+H)$^+$=362)

Step H: The similar procedure to Step F was applied for the preparation of 10-6E2 (m/z (ES) (M+H)$^+$=659).

Following a procedure analogous to the procedure described in Example 10 and the appropriate reagents, the following compounds were prepared:

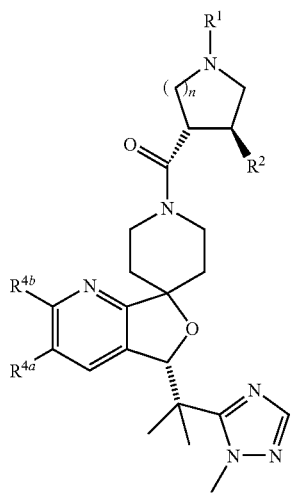
D1
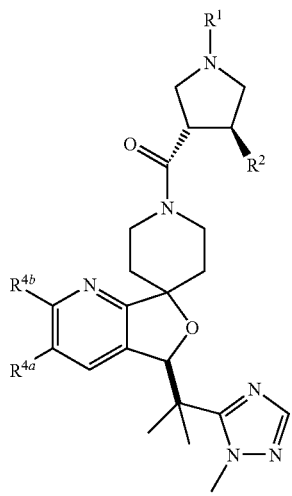
D2
| Example | R4b | R4a | R1 | R2 | n | D1 or D2 | Parent Ion m/z (M + H) |
|---|---|---|---|---|---|---|---|
| 11 | Me | Cl | 4-Tetrahydro-pyranyl | 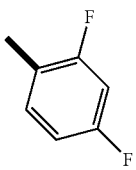 | 1 | D1 | 655 |
| 12 | Me | Cl | t-Butyl | 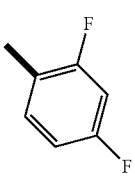 | 1 | D1 | 627 |
| 13 | Me | Cl | t-Butyl | 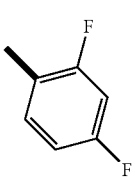 | 1 | D2 | 627 |

-continued
| | | | | | | | |
|---|---|---|---|---|---|---|---|
| 14 | Me | Cl | Hydroxy-t-butyl | 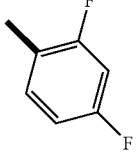 | 1 | D1 | 643 |
| 15 | H | Me | t-Butyl | 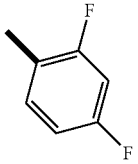 | 1 | D1 | 593 |
| 16 | H | Me | t-Butyl | 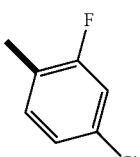 | 1 | D1 | 609 |
| 17 | Me | Cl | t-Butyl | 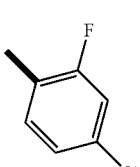 | 1 | D1 | 643 |
| 18 | Me | Me | t-Butyl | 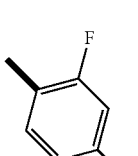 | 1 | D1 | 607 |
| 19 | Me | Me | t-Butyl | 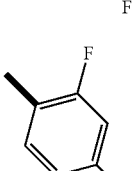 | 1 | D1 | 623 |
| 20 | $CF_3$ | H | t-Butyl | 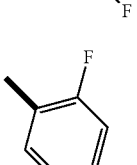 | 1 | D1 | 647 |
| 21 | Me | Me | t-Butyl | 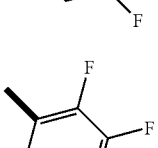 | 2 | D1 | 639 |
| 22 | $CF_3$ | H | t-Butyl | 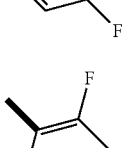 | 1 | D2 | 647 |

-continued
| 23 | Me | F | t-Butyl | 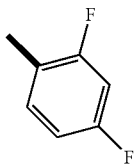 | 1 | D1 | 611 |
| 24 | Me | F | t-Butyl | 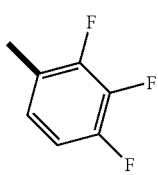 | 2 | D1 | 643 |
| 25 | Me | F | 4-Tetrahydro-pyranyl | 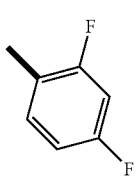 | 1 | D1 | 639 |
| 26 | Me | Cl | t-Butyl | 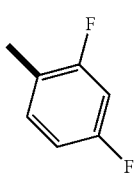 | 2 | D1 | 641 |
| 27 | Me | Cl | t-Butyl | 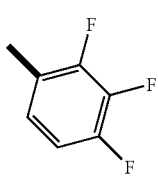 | 1 | D1 | 645 |
| 28 | Me | Cl | t-Butyl | 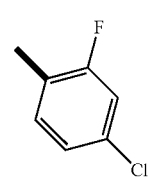 | 2 | D1 | 657 |

Example 29

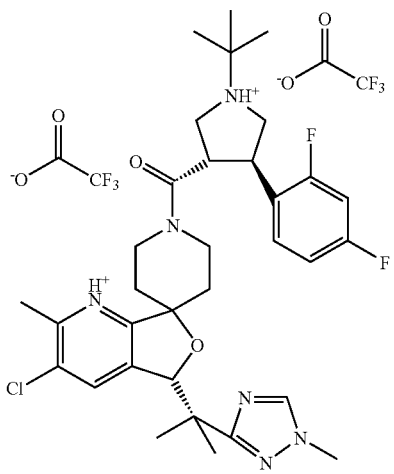

29D1

Compound 29D1 was prepared following a procedure analogous to the procedure described in Example 10 and using the appropriate reagents.

Example 30

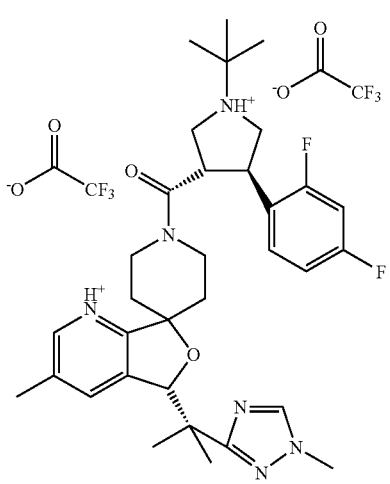

30D1

Compound 20D1 was prepared following a procedure analogous to the procedure described in Example 10 and using the appropriate reagents.

Example 31

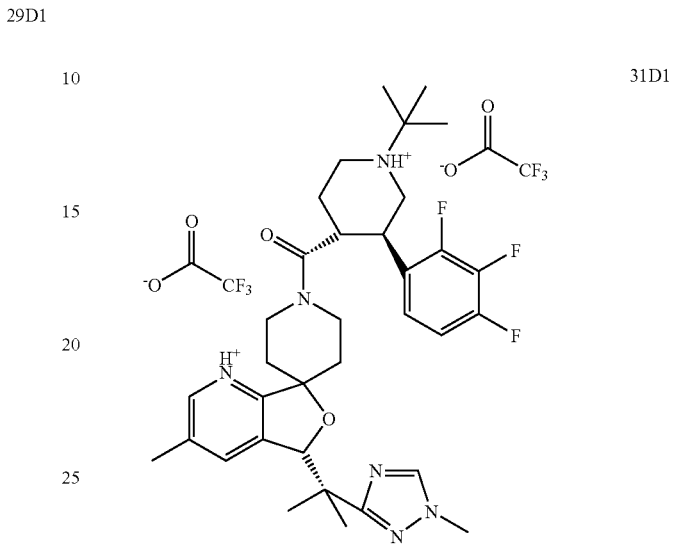

31D1

Compound 31D1 was prepared following a procedure analogous to the procedure described in Example 10 and using the appropriate reagents.

Example 32

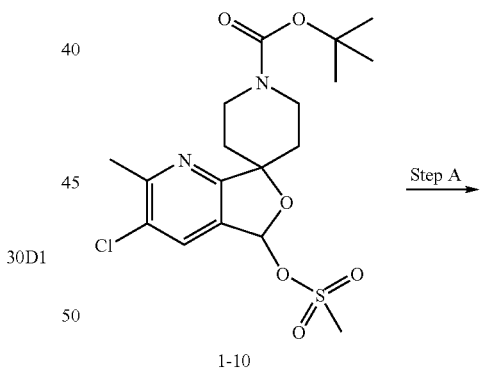

1-10

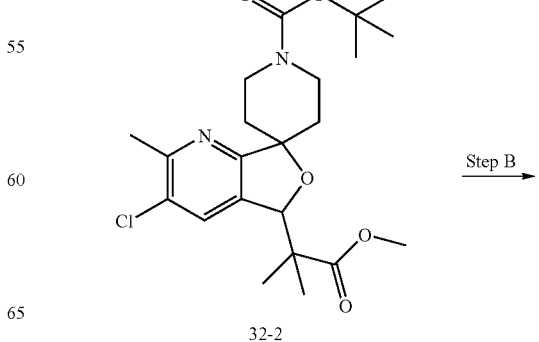

32-2

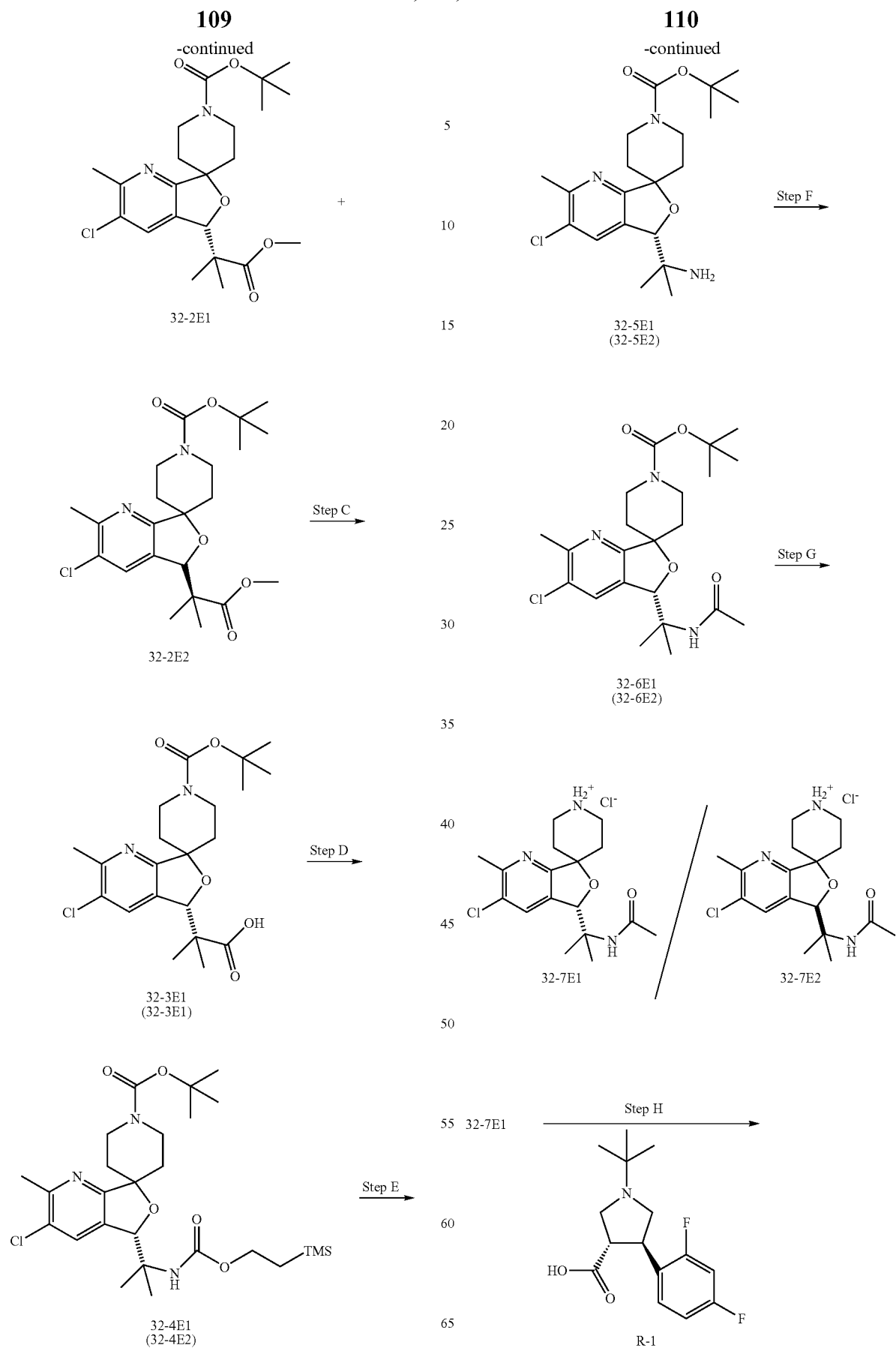

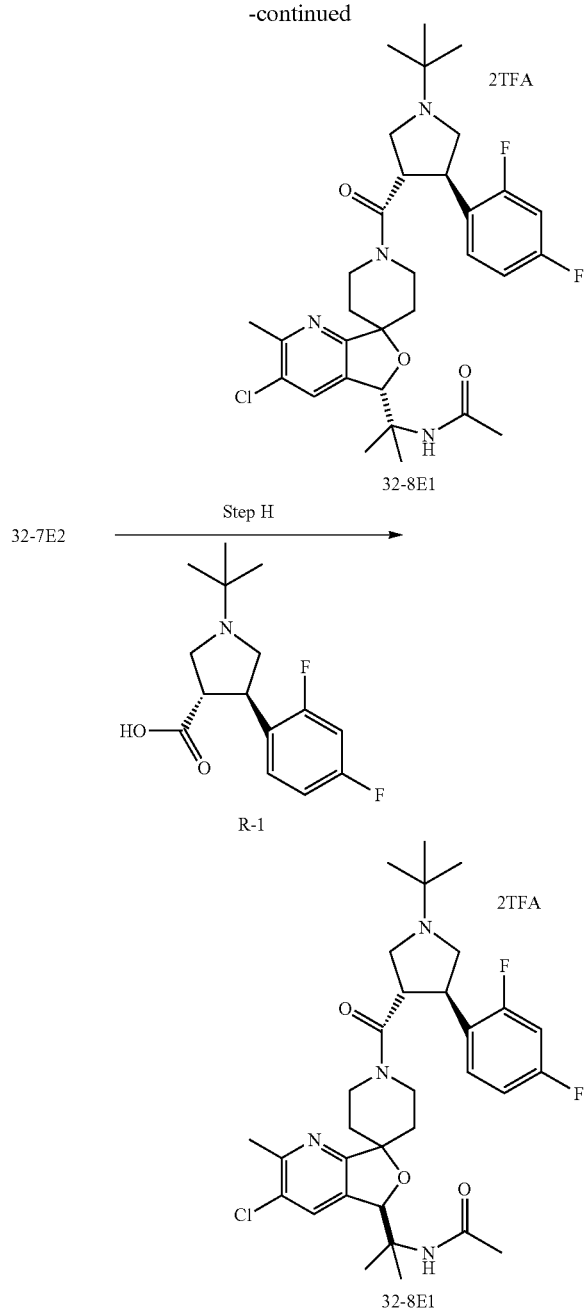

Step A: A solution of THF (6 mL), was cooled to −78° C., then LDA in THF (2M, 12.39 mL) was added, followed by the dropwise addition of methyl isobutyrate (2.81 g, 27.53 mmol) over 1 minute. The mixture was stirred at −78° C. for 30 minutes, then a solution of compound 1-10 (1.19 g, 2.73 mmol) in THF (6 mL) was added dropwise over 5 minutes. The reaction mixture was stirred at −78° C. for 1 hour, then quenched with saturated NH$_4$Cl (5 mL). The organic layer was separated and the aqueous layer was extracted by ethyl acetate (3×10 mL). The combined organic phases were washed with water, brine, dried over MgSO$_4$, filtered and concentrated. The resulting residue was purified by MPLC (25M, 10 to 25% ethyl acetate in hexanes) to afford compound 32-2 (m/z (ES) (M+H)$^+$=439).

Step B: The enantiomeric mixture of compound 32-2 was separated into individual enantiomers with a Chiral AD column using 0.5% IPA in heptane as the eluent to give enantiomer 32-2 E1 (Chiral AD column 3% IPA in heptane with retention time 7.73 min) and 32-2 E2 (Chiral AD column 3% IPA in heptane with retention time 10.89 min).

Step C: To a mixture of compound 32-2 E1 (0.312 g, 0.711 mmol) in methanol (3 mL) was added dropwise NaOH (5N, 1 μL). The resulting reaction mixture was stirred at room temperature for 30 minutes, then additional NaOH (5N, 1 mL) was added and the reaction was heated in an oil bath of 40° C. for 3 hours. The mixture was concentrated by rotary evaporation to half volume. The resulting residue was diluted with water (5 mL) and ethyl acetate (10 mL), and the mixture was acidified to pH=2 with HCl (12N, 900 uL). The organic layer was separated and the aqueous layer was extracted with ethyl acetate (3×10 mL). The combined organic phases were washed with brine, dried over MgSO$_4$, filtered and concentrated to afford compound 32-3 E1 (m/z (ES) (M+H)$^+$=425). Using the procedure of Example 32, Step C, 32-3 E2 (m/z (ES) (M+H)$^+$=425) may be prepared.

Step D: To a mixture of compound 32-3 E1 (0.234 g, 0.551 mmol), toluene (2 mL) and TEA (0.167 g, 1.65 mmol) was added diphenylphosphonyl azide (DPPA, 0.227 g, 0.826 mmol). The reaction mixture was heated at 80° C. for 30 minutes and then TMS-ethanol (0.195 g, 1.652 mmol) was added dropwise over 1 minute. The resulting reaction mixture was then heated to 80° C. for 15 hours, cooled to room temperature and quenched by addition of water (4 mL). The organic layer was separated and the aqueous layer was extracted with ethyl acetate (3×10 mL). The combined organic phases were washed with water, brine, dried over MgSO$_4$, filtered and concentrated. The resulting residue was purified by MPLC (25 s, 0 to 30% ethyl acetate in hexanes) to afford compound 32-4E1 (m/z (ES) (M+H)$^+$=541). Using the procedure of Example 32 Step D, 32-4E2 (m/z (ES) (M+H)$^+$=541) was prepared.

Step E: To a mixture of compound 32-4E1 (0.290 g, 0.537 mmol) and THF (2 mL) was added dropwise a solution of TBAF in THF (1M, 2 mL) over 3 minutes. The resulting reaction mixture was stirred at room temperature for 3 hours, then quenched with water (4 mL) and ethyl acetate (4 mL). The organic layer was separated, and the aqueous layer was extracted with ethyl acetate (3×5 mL). The combined organic phases were washed with brine, dried over MgSO$_4$, filtered and concentrated to afford compound 32-5E1 (m/z (ES) (M+H)$^+$=396) which was used in the next step. Using the procedure of Example 32 Step E, 32-5E2 (m/z (ES) (M+H)$^+$=396) was prepared.

Step F: To a mixture of compound 32-5E1 (0.537 mmol) in CH$_2$Cl$_2$ (2 mL) and TEA (0.163 g, 1.61 mmol) was added dropwise acetyl chloride (0.063 g, 10.805 mmol) over 1 min. The resulting mixture was stirred at room temperature for 1 hour, then quenched with water (2 mL). The organic layer was separated and the aqueous layer was extracted with ethyl acetate (3×). The combined organic phases were washed with saturated NaHCO$_3$ (3 mL), brine, dried over MgSO$_4$, filtered and concentrated. The resulting residue was purified by MPLC (12M, 0 to 50% ethyl acetate in hexanes) to afford compound 32-6E1(Rf=0.2 by ethyl acetate:hexanes=2:3, m/z (ES) (M+H)$^+$=438). Using the procedure of Example 32 Step F, 32-6E2 (m/z (ES) (M+H)$^+$=438) was prepared.

Step G: A mixture of compound 32-6E1 (0.031 g, 0.071 mmol) and concentrated HCl (0.5 mL) in methanol (1 mL) was stirred at 40° C. for 30 minutes. Then the mixture was concentrated and the residue was co-evaporated with toluene three times to afford compound 32-7E1 (m/z (ES) (M+H)$^+$=338). Using the procedure of Example 32 Step G, 32-7E2 (m/z (ES) (M+H)$^+$=338) was prepared.

Step H: To a mixture of compound 32-7E1 (0.071 mmol), acid R-1 (0.022 g, 0.078 mmol) and Hunig's base (0.046 g, 0.354 mmol) was added HOAT (0.010 g, 0.071 mmol) and HATU (0.038 g, 0.099 mmol). The resulting reaction mixture was stirred at room temperature for 2 hours, then concentrated. The resulting residue was dissolved in methanol (1 mL), filtered through a syringe, and washed with methanol (2 mL). The filtrate was concentrated and the resulting residue was purified via a RP HPLC (YMC column, 20% to 80% acetonitrile in water) to afford the TFA salt of compound 32-8D1 (m/z (ES) (M+H)$^+$=603). Using the procedure of Example 32 Step H, 32-8D2 (m/z (ES) (M+H)$^+$=603) was prepared.

Example 33

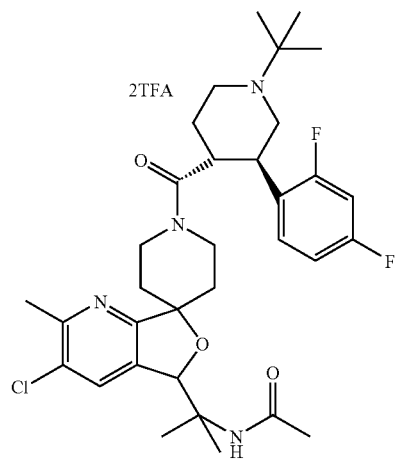

33D1

Compound 33D1 was prepared following a procedure analogous to the procedure described in Example 32 and using the appropriate reagents.

Example 34

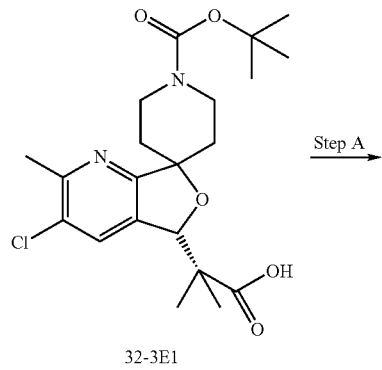

32-3E1

Step A

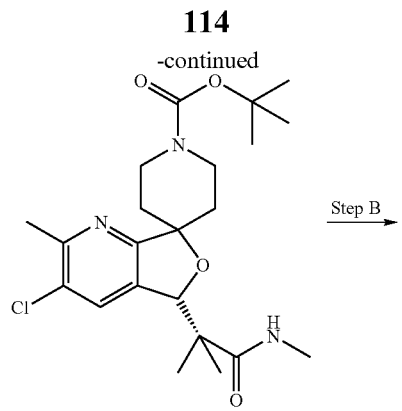

34-2E1

Step B

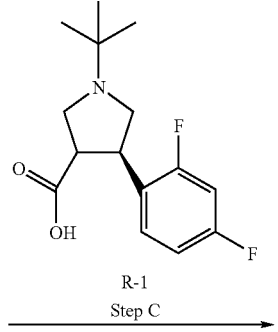

R-1

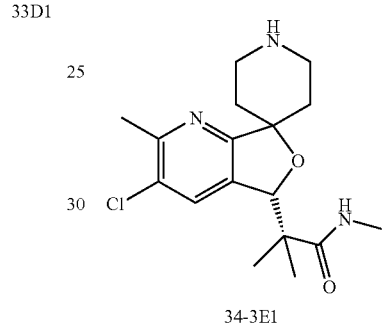

34-3E1

Step C

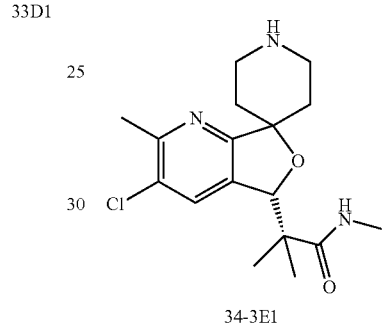

34-4D1

Step A: To a solution of compound 32-3 E1 (0.087 g, 0.205 mmol) in CH$_2$Cl$_2$ (2 mL) was added HATU (0.093 g, 0.246 mmol). The resulting reaction mixture was stirred for 10 minutes, then a solution of methylamine (0.032 g, 1.024 mmol) in THF was added dropwise in 1 minute. The resulting reaction mixture was stirred at room temperature for 30 minutes. One additional equivalent of HATU and MeNH$_2$ was added. The reaction mixture was stirred at room temperature for 15 hours, then concentrated and the resulting residue was purified by Prep TLC (2000 nM, ethyl acetate:hexanes=2:3) to afford compound 34-2 E1 (m/z (ES) (M+H)$^+$=438).

Step B: A mixture of compound 34-2 E1 (0.024 g, 0.055 mmol) and concentrated HCl (0.5 mL) in methanol (1 mL) was stirred at 40° C. for 30 minutes. The mixture was concentrated and the resulting residue was co-evaporated with toluene three times to afford compound 34-3 E1 (m/z (ES) (M+H)$^+$=338).

Step C: To a mixture of compound 34-3 E1 (0.055 mmol), acid R-1 (0.017 g, 0.060 mmol) and Hunig's base (0.035 g, 0.274 mmol) was added HOAT (0.007 g, 0.055 mmol) and HATU (0.029 g, 0.077 mmol). The resulting reaction mixture was stirred at room temperature for 2 hours, then concentrated. The resulting residue was dissolved in methanol (1 mL), filtered through a syringe, and washed with methanol (2 mL). The filtrate was concentrated and the resulting residue was purified by RP HPLC (YMC column, 20% to 80% acetonitrile in water) to afford the TFA salt of compound 34-4D1 (m/z (ES) (M+H)$^+$=603).

Following a procedure analogous to the procedure described in Example 34 and the appropriate reagents, the following compounds were prepared:

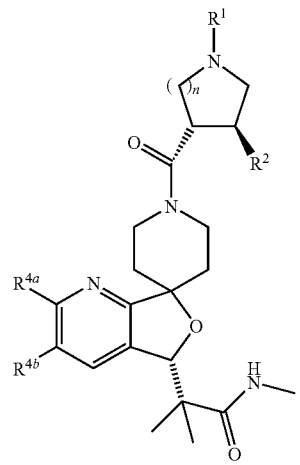

D1

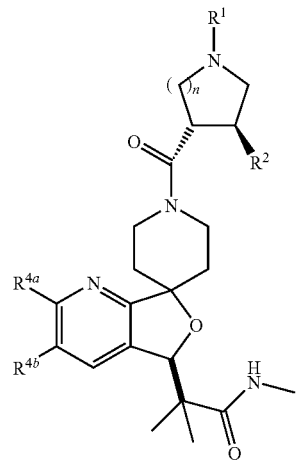

D2

| Example | R4b | R4a | R1 | R2 | n | D1 or D2 | Parent Ion m/z (M + H) |
|---------|-----|-----|-----|-----|---|----------|------------------------|
| 35 | Me | Cl | t-Butyl | 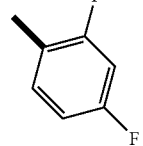 | 1 | D2 | 603 |

-continued

| 36 | Me | F | t-Butyl | (2,4-difluorophenyl) | 1 | D1 | 587 |
| 37 | Me | F | t-Butyl | (3-F, 5-Cl phenyl) | 1 | D2 | 627 |
| 38 | Me | F | t-Butyl | (2,4-difluorophenyl) | 2 | D1 | 601 |
| 39 | Me | Cl | Hydroxy-t-butyl | (2,4-difluorophenyl) | 1 | D1 | 643 |

Example 40

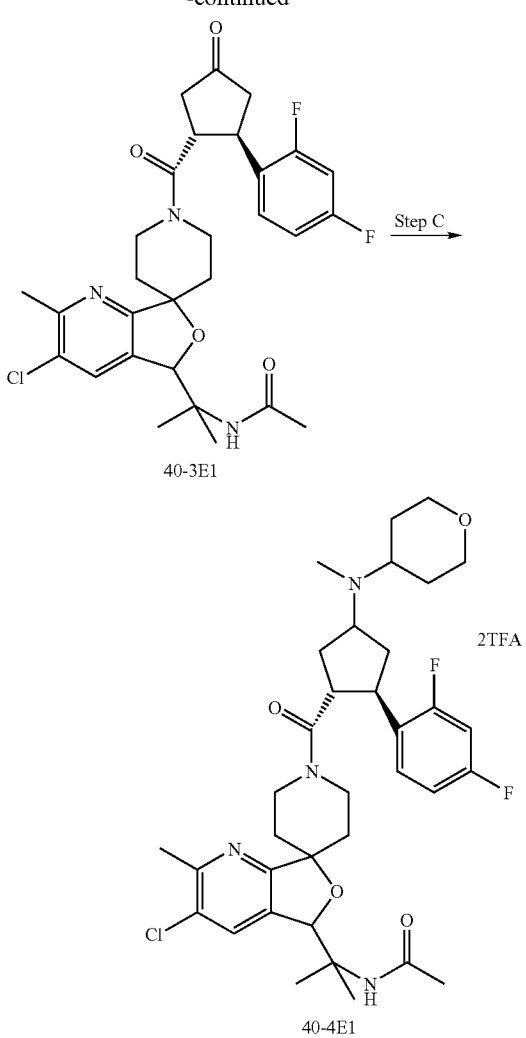

Step A: To a mixture of compound 32-7E1 (0.066 mmol), acid 0-5 (0.00.017 g, 0.073 mmol) and Hunig's base (0.043 g, 0.331 mmol) was added HOAT (0.009 g, 0.066 mmol) and HATU (0.035 g, 0.093 mmol). The resulting reaction mixture was stirred at room temperature for 2 hours, then the reaction mixture was concentrated and the residue was dissolved in methanol (1 mL), filtered through a syringe and washed with methanol (2 mL). The filtrate was concentrated and the resulting residue was purified by preparative TLC (2000 nm, ethyl acetate:hexanes=3:2) to afford compound 40-2 E1 (m/z (ES) (M+H)$^+$=559).

Step B: To a solution of compound 40-2 E1 (0.037 g, 0.066 mmol) in THF:H$_2$O (4:1, 1:0.25 mL) was added a solution of OsO$_4$ in t-butanol (2.4%, 0.001 g). The resulting mixture was stirred for 1 minute, then a solution of sodium metaperiodinate in water (0.071 g, 0.331 mmol in 1 mL) was added dropwise over 2 min. The resulting reaction mixture was stirred at room temperature for 15 hours, then quenched with a mixture of saturated NaHCO$_3$ (3 mL) and Na$_2$S$_2$O$_3$ (15%, 3 mL). The reaction mixture was extracted with ethyl acetate (3×5 mL), washed with water, brine, dried over MgSO$_4$, filtered and concentrated to afford compound 40-3 E1 (m/z (ES) (M+H)$^+$=561), which was used in the next step without further purification.

Step C: A mixture of compound 40-3 E1 (0.066 mmol), methyl-4-pyranylamine HCl salt (0.079 g, 0.529 mmol), CH$_2$Cl$_2$ and TEA (0.067 g, 0.661 mmol) was stirred for 30 minutes, then newly activated powder molecular sieves 4A (0.2 g) were added followed by sodium triacetyloxyborohydride (0.112 g, 0.529 mmol). The reaction mixture was stirred at room temperature for 15 hours, then diluted by methanol (5 mL) and filtered. The filtrate was concentrated, and the resulting residue was partitioned between water and ethyl acetate. The organic layer was separated and the aqueous layer was extracted by ethyl acetate (3×10 mL). The combined organic phases were dried over MgSO$_4$, filtered and concentrated. The resulting residue was purified by RP-HPLC (YMC reverse phase column, 20 to 80% acetonitrile in water) to afford the TFA salt of compound 40-4E1 (m/z (ES) (M+H)$^+$= 659).

Following a procedure analogous to the procedure described in Example 40 and the appropriate reagents, the following compounds were prepared:

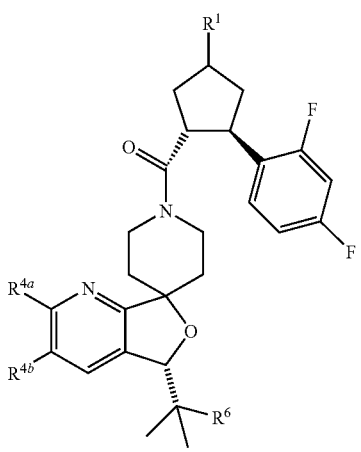

D1

-continued
D2
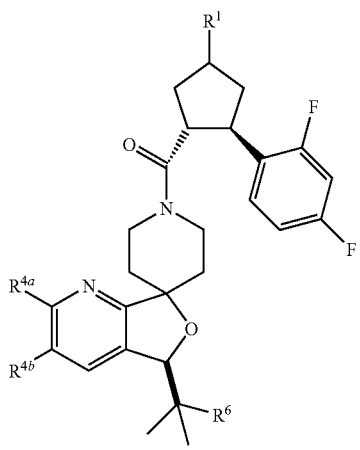
| Example | R4a | R4b | R1 | R6 | D1 or D2 | Parent Ion m/z (M + H) |
|---|---|---|---|---|---|---|
| 41 | Me | Cl | N-methyl-tetrahydropyran-4-yl | NHC(O)CH₃ | D2 | 659 |
| 42 | Me | Cl | N-methyl-tetrahydropyran-4-yl | C(O)NHCH₃ | D1 | 659 |
| 43 | Me | Cl | N-methyl-tetrahydropyran-4-yl | C(O)NHCH₃ | D2 | 659 |
| 44 | Me | Cl | morpholine | CN | D1 | 599 |
| 45 | Me | Cl | 3-fluoropyrrolidine | CN | D1 | 601 |
| 46 | Me | Cl | 2-oxa-5-azabicyclo[2.2.1]heptane | CN | D1 | 611 |
| 47 | Me | Cl | 2-oxa-5-azabicyclo[2.2.1]heptane | 1,2-dimethyl-1H-1,2,4-triazol-5-yl | D1 | 667 |

-continued
| # | R1 | R2 | amine | Ar | method | mass |
|---|----|----|-------|-----|--------|------|
| 48 | Me | Cl | 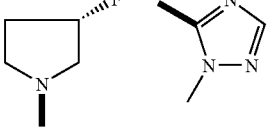 | 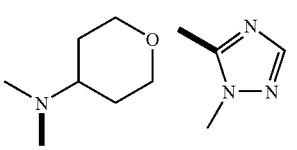 | D1 | 657 |
| 49 | Me | Cl | 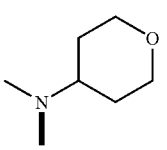 | 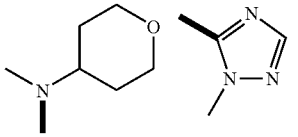 | D1 | 683 |
| 50 | Me | Cl | 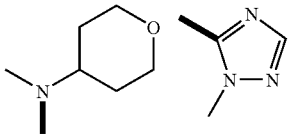 | CN | D1 | 627 |
| 51 | Me | Me | 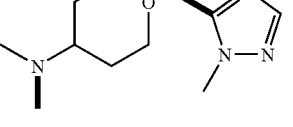 | 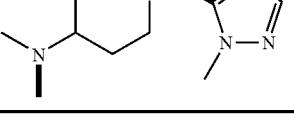 | D1 | 661 |
| 52 | CF₃ | H | | | D1 | 701 |
| 53 | H | Me | | | D1 | 649 |
| 54 | Me | F | | | D1 | 667 |
Example 55
-continued
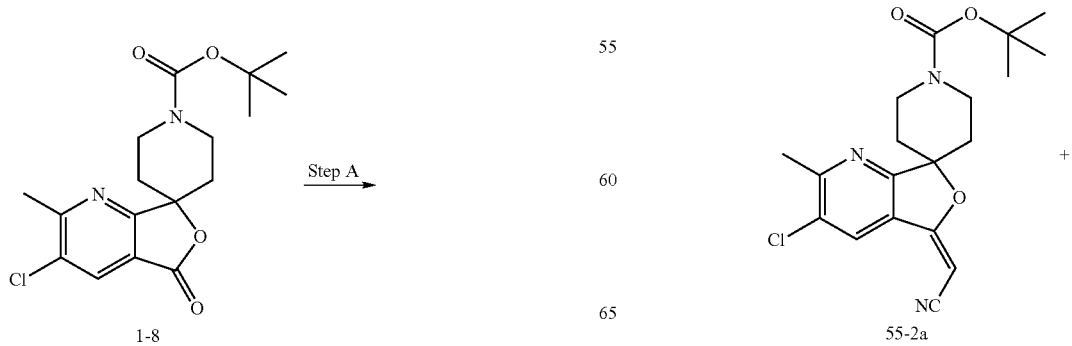

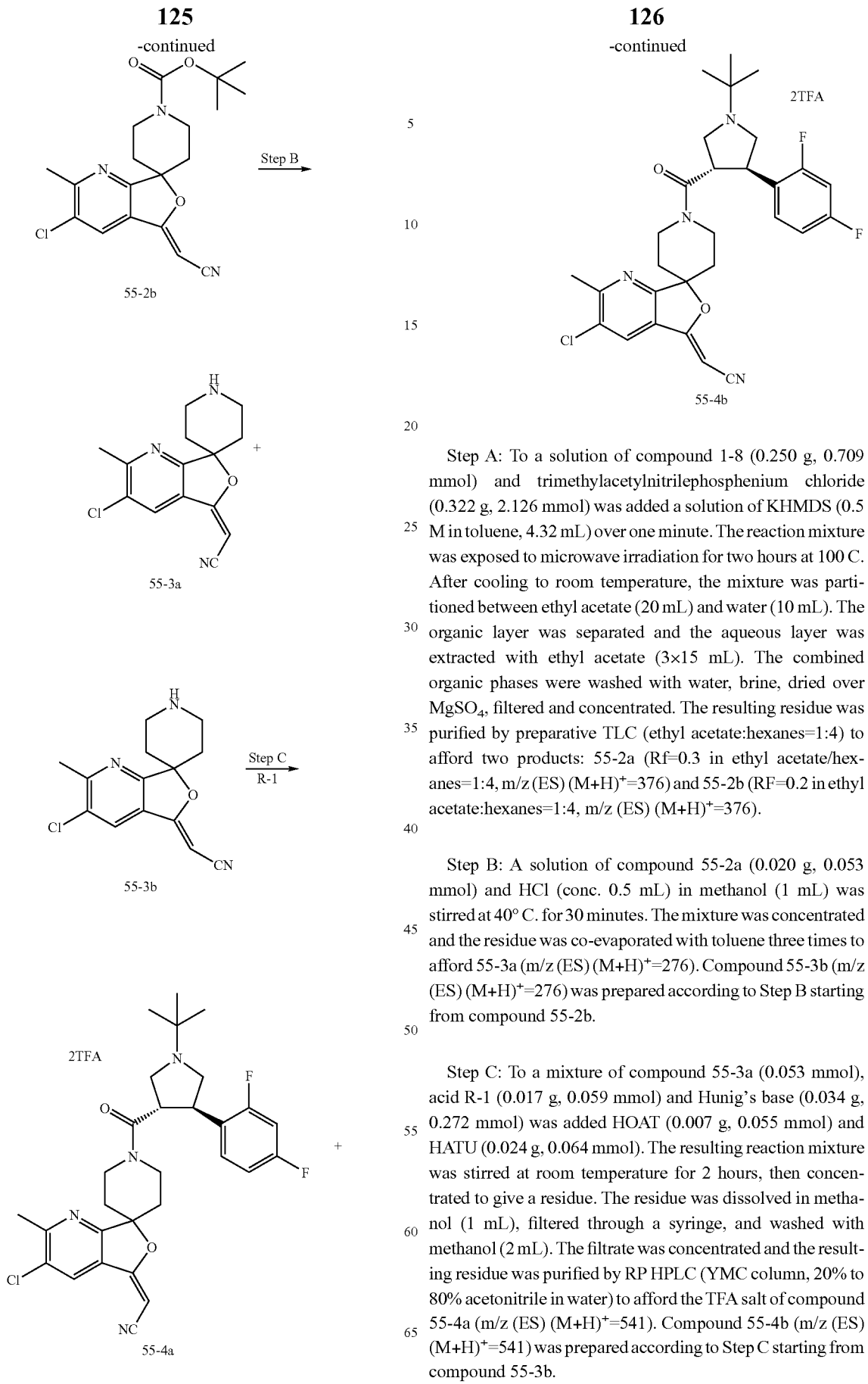

Step A: To a solution of compound 1-8 (0.250 g, 0.709 mmol) and trimethylacetylnitrilephosphenium chloride (0.322 g, 2.126 mmol) was added a solution of KHMDS (0.5 M in toluene, 4.32 mL) over one minute. The reaction mixture was exposed to microwave irradiation for two hours at 100 C. After cooling to room temperature, the mixture was partitioned between ethyl acetate (20 mL) and water (10 mL). The organic layer was separated and the aqueous layer was extracted with ethyl acetate (3×15 mL). The combined organic phases were washed with water, brine, dried over MgSO$_4$, filtered and concentrated. The resulting residue was purified by preparative TLC (ethyl acetate:hexanes=1:4) to afford two products: 55-2a (Rf=0.3 in ethyl acetate/hexanes=1:4, m/z (ES) (M+H)$^+$=376) and 55-2b (RF=0.2 in ethyl acetate:hexanes=1:4, m/z (ES) (M+H)$^+$=376).

Step B: A solution of compound 55-2a (0.020 g, 0.053 mmol) and HCl (conc. 0.5 mL) in methanol (1 mL) was stirred at 40° C. for 30 minutes. The mixture was concentrated and the residue was co-evaporated with toluene three times to afford 55-3a (m/z (ES) (M+H)$^+$=276). Compound 55-3b (m/z (ES) (M+H)$^+$=276) was prepared according to Step B starting from compound 55-2b.

Step C: To a mixture of compound 55-3a (0.053 mmol), acid R-1 (0.017 g, 0.059 mmol) and Hunig's base (0.034 g, 0.272 mmol) was added HOAT (0.007 g, 0.055 mmol) and HATU (0.024 g, 0.064 mmol). The resulting reaction mixture was stirred at room temperature for 2 hours, then concentrated to give a residue. The residue was dissolved in methanol (1 mL), filtered through a syringe, and washed with methanol (2 mL). The filtrate was concentrated and the resulting residue was purified by RP HPLC (YMC column, 20% to 80% acetonitrile in water) to afford the TFA salt of compound 55-4a (m/z (ES) (M+H)$^+$=541). Compound 55-4b (m/z (ES) (M+H)$^+$=541) was prepared according to Step C starting from compound 55-3b.

Example 56

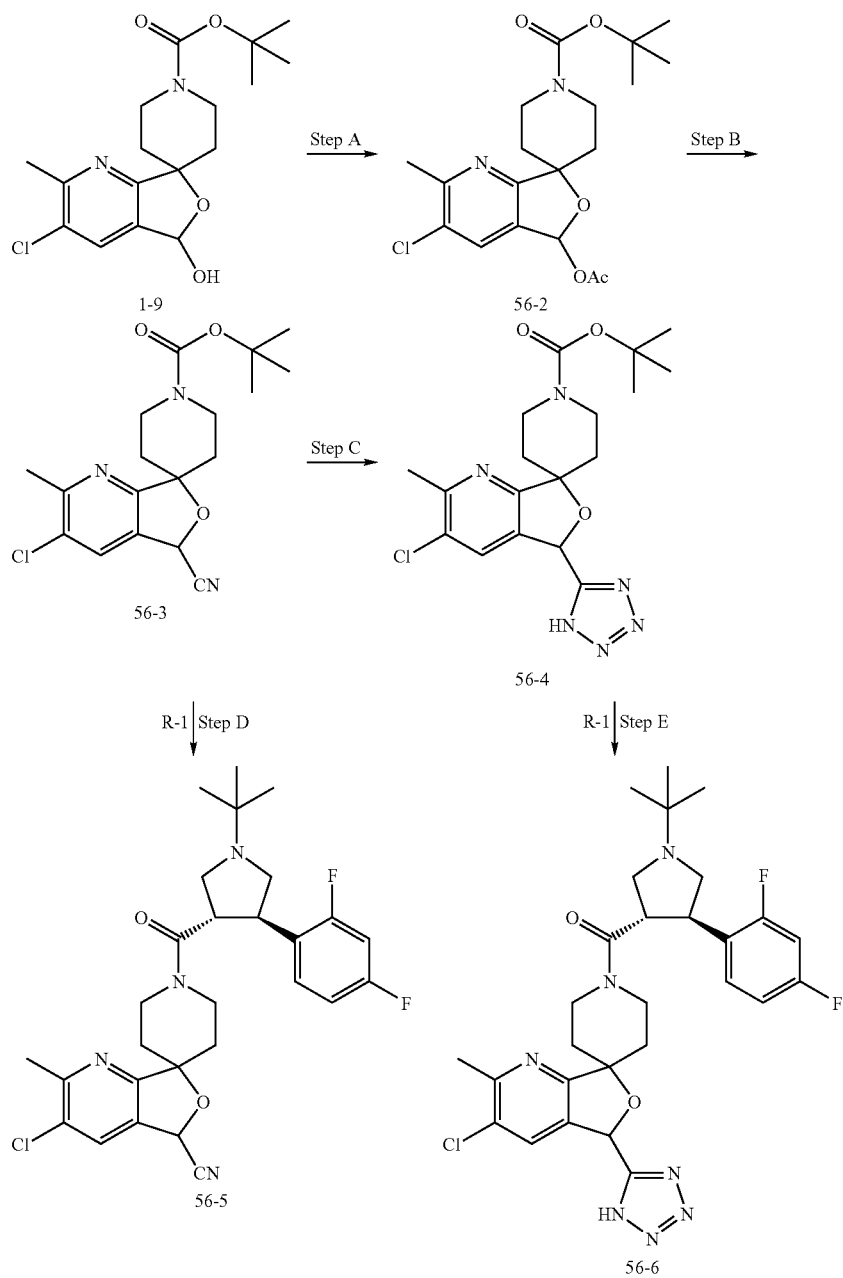

Step A: To a mixture of compound 1-9 (1.35 g, 3.81 mmol), CH$_2$Cl$_2$ (10 mL) and TEA (1.16 g, 11.41 mmol) was added dropwise acetyl anhydride (0.583 g, 5.71 mmol) over 2 min. The reaction mixture was then stirred at room temperature for 24 hours, then concentrated. The resulting residue was purified by MPLC (12M, 0 to 40% ethyl acetate in hexanes) to afford compound 56-2 (Rf=0.4 by 20% ethyl acetatein hexanes, m/z (ES) (M+H)$^+$=397).

Step B: A mixture of compound 56-2 (0.132 g, 0.333 mmol), CH$_2$Cl$_2$ (1 mL) and TMSCN 0.049 g, 0.499 mmol) was cooled to 0° C. in ice water bath, followed by the dropwise addition of boron trifluoro etherate (0.005 g, 0.033 mmol) over 1 min. The resulting reaction mixture was stirred at 0° C. for 20 minutes, then concentrated and the resulting residue was purified by MPLC (12M, 0 to 40% ethyl acetate in hexanes) to afford compound 56-3 (m/z (ES) (M+H)$^+$=364).

Step C: A mixture of compound 56-3 (0.051 g, 0.140 mmol), sodium azide (0.109 g, 1.68 mmol), ammonium chloride (0.090 g, 1.68 mmol) and DMF (1 mL) in a sealed tube was exposed to microwave irradiation at 100° C. for 10 min. The reaction mixture was diluted with water (2 mL) and neutralized with 1N HCl to pH=4, and extracted with ethyl acetate (3×10 mL). The combined organic phases were washed with water, brine, dried over MgSO$_4$, filtered and concentrated to afford product 56-4 (m/z (ES) (M+H)$^+$=407) which was used in the next step without further purification.

Step D: A mixture of compound 56-3 (0.030 g, 0.082 mmol) in methylene chloride (1.5 mL) was cooled to 0° C. in ice water. Borontrifluoride etherate (3 eq) was added dropwise, and the resulting reaction mixture was stirred at 0° C. for 30 min. The reaction was quenched with saturated NaHCO$_3$ (3 mL); the organic layer was separated and the aqueous layer was extracted by methylene chloride (3×3 mL). The combined organic layers were washed with brine, dried over MgSO$_4$, filtered and concentrated to give the free amine. To a mixture of the free amine, acid R-1 and Hunig's base (0.053 mg, 0.412 mmol) was added HATU (0.038 g, 0.099 mmol) and HOAT (0.011 g, 0.082 mmol). The resulting reaction mixture was stirred at room temperature for 2 hours, then concentrated to give a residue. The residue was dissolved in methanol (1 mL), filtered through a syringe and washed with methanol (2 mL). The filtrate was concentrated and the resulting residue was purified by RP HPLC (YMC column, 20% to 80% acetonitrile in water) to give the TFA salt of compound 56-5 (m/z (ES) (M+H)$^+$=529).

Step E: Using a procedure analogous to the procedure in Step D and starting with compound 56-4, the TFA salt of compound 56-6 (m/z (ES) (M+H)$^+$=571) was obtained.

Example 57

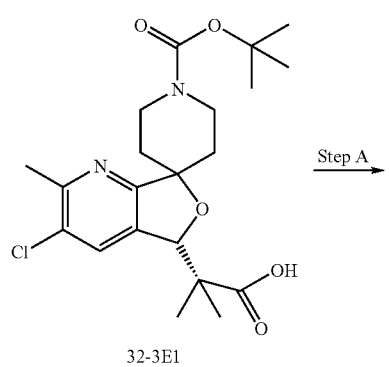

32-3E1

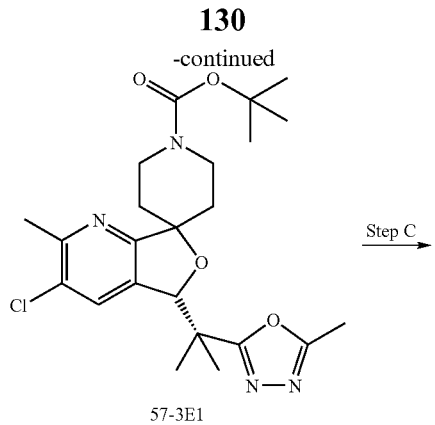

57-3E1

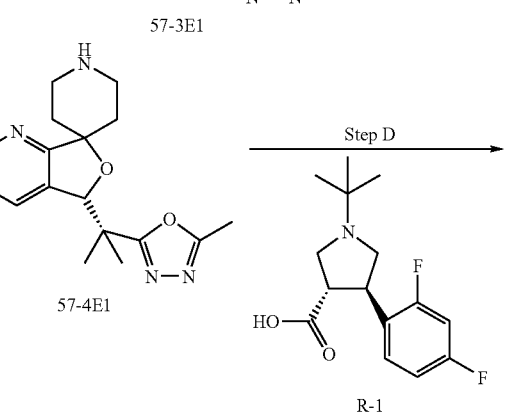

57-4E1

R-1

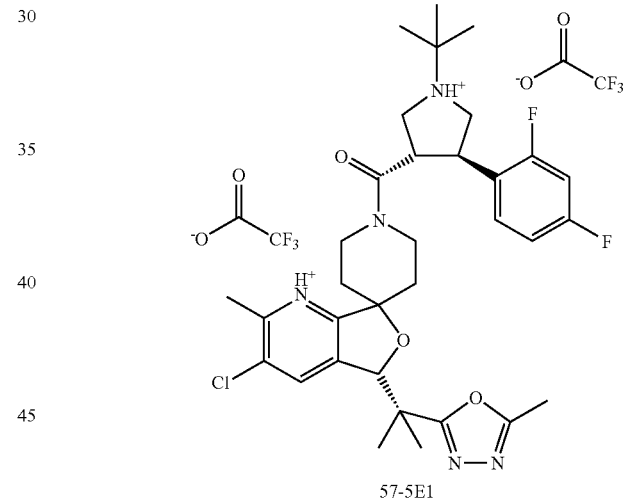

57-5E1

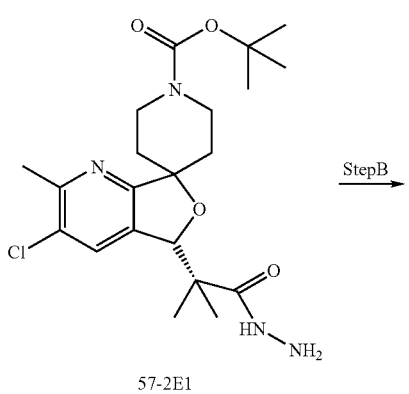

57-2E1

Step A: A mixture of compound 32-3 E1 (0.06 g, 0.14 mmol), HOAT (0.029 g, 0.21 mmol), EDC (41 mg, mmol) and DMF (1.5 mL) was cooled in an ice bath of 0° C. for 30 minutes under nitrogen, then hydrazine (0.07 g, 23.61 mmol) was added dropwise with vigorous stirring. The resulting reaction mixture was gradually warmed to room temperature and stirred for 16 hours. The reaction was then quenched with water (10 mL) and ethyl acetate (20 mL). The organic layer was separated and the aqueous layer was extracted with ethyl acetate (3×20 mL). The combined organic phases were washed by water, brine, dried over MgSO$_4$, filtered and concentrated to give 57-2 E1 (m/z (ES) (M+H)$^+$=439), which was used directly to next step without further purification.

Step B: To a 50 mL sealed vessel was charged with compound 57-2 E1 (0.057 g, 0.13 mmol) and triethyl orthoacetate (1.5 mL). The vessel was then flushed with nitrogen, sealed with screw cap, and heated in an oil bath of 145° C. for 3 hours. After cooling to room temperature, the reaction mixture was partitioned between ethyl acetate (20 mL) and NaHCO$_3$(saturated, 10 mL). The organic layer was separated and the aqueous layer was extracted with ethyl acetate (3×10 mL). The combined organic phases were washed with water, brine, dried over MgSO$_4$, filtered and concentrated to give a residue. The residue was purified by Preparative TLC to afford product 57-3 E1 as a white solid (Rf=0.2 by ethyl acetate:hexanes=2:3, m/z (ES) (M+H)$^+$=463).

Step C: Compound 57-3 E1 (0.02 g, 0.043 mmol) was treated with 4 N HCl in dioxane (1 mL) at room temperature for 30 minutes. Then the reaction mixture was concentrated and the resulting residue was co-evaporated with three times with toluene to afford compound 57-4E1 (m/z (ES) (M+H)$^+$= 363).

Step D: A mixture of compound 57-4E1 (0.043 mmol), methylene chloride (1 mL), acid R-1 (0.015 g, 0.048 mmol) and Hunig's base (0.016 g, 0.13 mmol) was stirred until all of the solid dissolved. HOAT (0.065 g, 0.048 mmol) and HATU (0.02 g, 0.052 mmol) were then added and the resulting reaction mixture was stirred at room temperature for 2 hours. The reaction mixture was concentrated and the resulting residue was dissolved in methanol (1 mL) and filtered through a syringe and washed with methanol (2 mL). The filtrate was concentrated and the resulting residue was purified by RP HPLC (YMC column, 20% to 80% acetonitrile in water) to afford the TFA salt of compound 57-5E1 (m/z (ES) (M+H)$^+$= 628).

Example 58

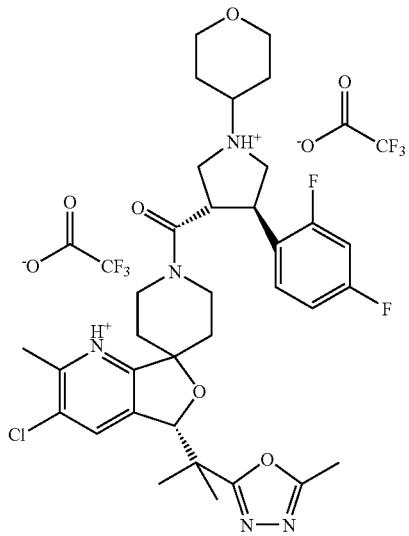

58E1

Compound 58E1 was prepared following a coupling procedure analogous to the procedure described in Example 57-5E1 and using the appropriate acid.

Example 59

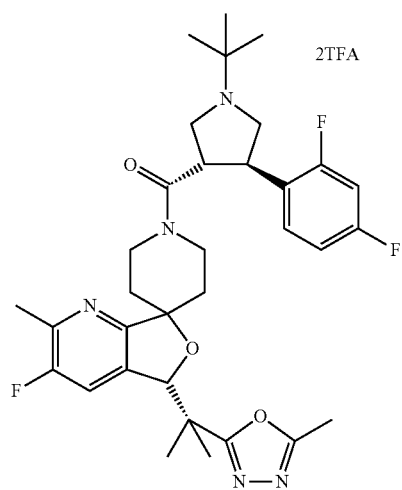

59E1

Compound 59E1 (m/z (ES) (M+H)$^+$=612) was prepared following a procedure analogous to the procedure described in Example 57 and using the appropriate acid.

Example 60

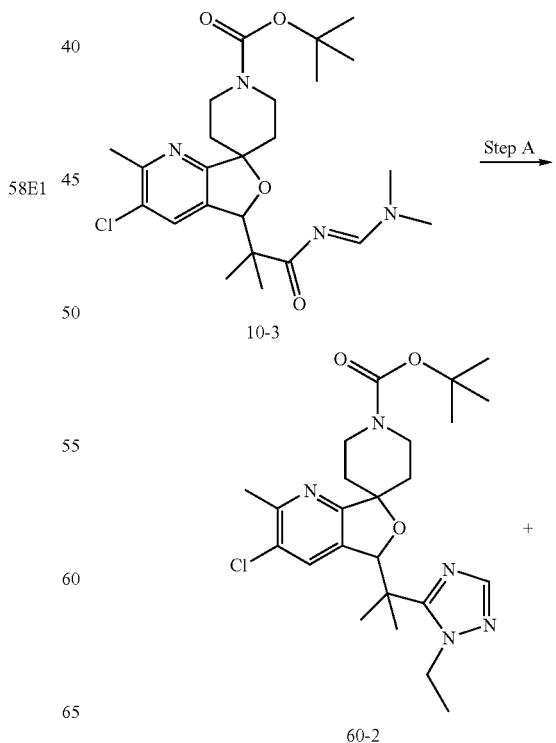

-continued
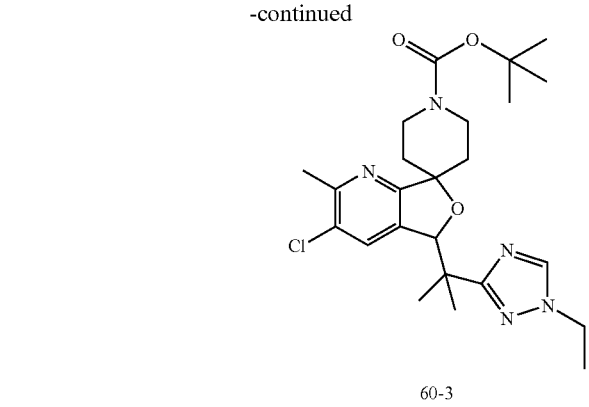
60-3
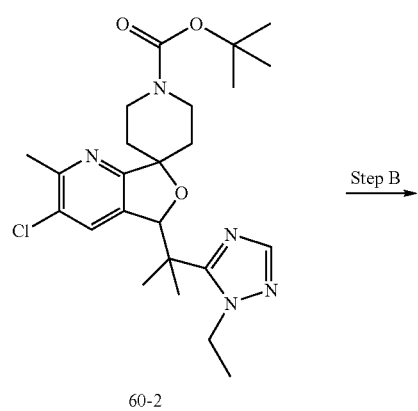
60-2
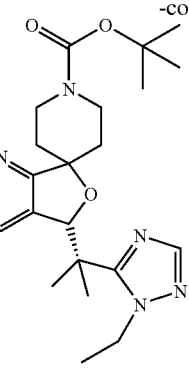
60-2 E1
Step B
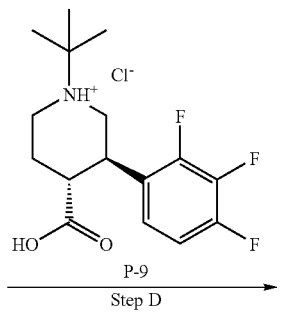
60-2 E1
+
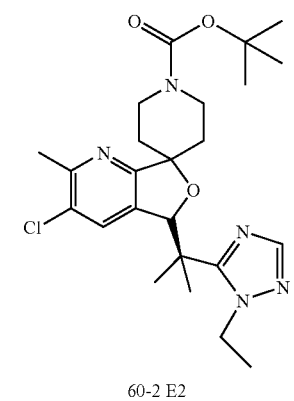
60-2 E2
-continued
60-2 E1
Step C
60-4 E1
P-9
Step D
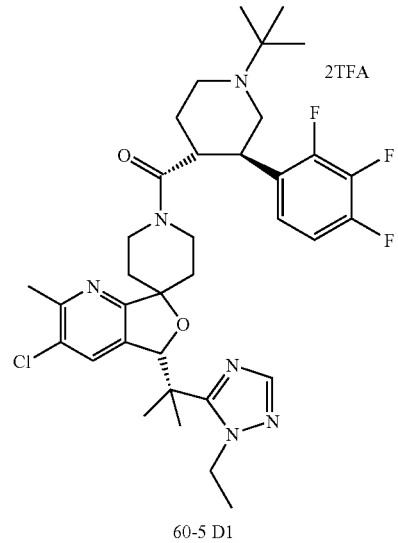
60-5 D1
Step A: To a 50 mL one neck round bottom flask was charged with 10-3 (256 mg, 0.534 mmol) along with HOAc (3 mL). The mixture was cooled to 0° C. in an ice-water bath. Ethyl hydrazine (34% aqueous solution, 189 uL, 1.069 mmol) was then added dropwise over 2 minutes. The resulting reaction mixture was then stirred and gradually heated to 95° C.

for 1 hour. After cooling to room temperature, the solvent was removed, and the resulting residue was partitioned between ethyl acetate (10 ml) and saturated NaHCO$_3$ (60 mL). The organic layer was separated and the aqueous layer was extracted with ethyl acetate (3×10 mL). The combined organic phases were washed with water, brine, dried over MgSO$_4$, filtered and concentrated. The resulting residue was then purified by MPLC (12 g silica gel, 0 to 60% ethyl acetate in hexanes) to afford foamy solid product 60-2 (Rf=0.2 by ethyl acetate:hexanes=1:4, m/z (ES) (M+H)$^+$=476) and regio isomer 60-3 (4.6%, Rf=0.05 by ethyl acetate:hexanes=1:4, m/z (ES) (M+H)$^+$=476) as racemic mixtures.

Step B: The racemic mixture of 60-2 was separated using chiral AD column using 7% ethanol in heptane to afford product 60-2 E1 (100% ee, Rt=17.4 min by chiral AD column using 7% ethanol in heptane) and 60-2 E2 (100% ee, Rt=22.3 min by Chiral AD column using 7% ethanol in heptane).

Step C: A mixture of compound 60-2 E1 (0.016 g, 0.035 mmol) and concentrated HCl (0.5 mL) in methanol (1 mL) was stirred at 40° C. for 30 min. The mixture was then concentrated and the resulting residue was co-evaporated with toluene three times to afford compound 60-4 E1.

Step D: To a mixture of compound 60-4 E1 (0.035 mmol), acid P-9 (0.016 g, 0.045 mmol) and Hunig's base (0.022 g, 0.173 mmol) was added HOAT (0.005 g, 0.035 mmol) and HATU (0.018 g, 0.048 mmol). The resulting reaction mixture was stirred at room temperature for 2 hours, and concentrated. The resulting residue was dissolved in methanol (1 mL), filtered through a syringe and washed with methanol (2 mL). The filtrate was concentrated and the resulting residue was purified by RP HPLC (YMC column, 20% to 80% acetonitrile in water) to afford compound 60-5 D1 as a TFA salt (m/z (ES) (M+H)$^+$=673).

Example 61

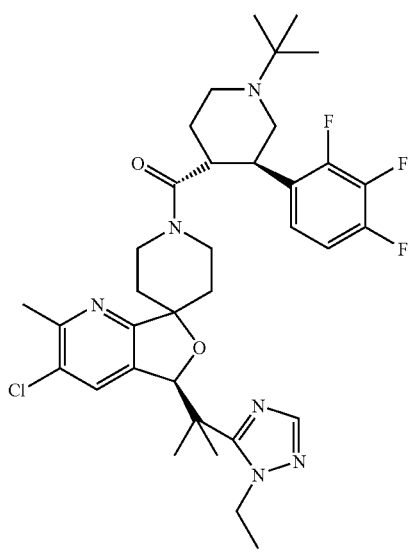

Example 61-D1 was prepared using an analogous procedure to that used to prepare Example 60; (m/z (ES) (M+H)$^+$=673).

Example 62

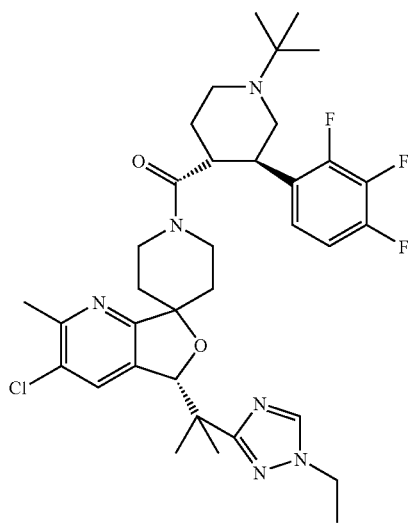

Example 62-D1 was prepared using an analogous procedure to that used to prepare Example 60; (m/z (ES) (M+H)$^+$=673).

Example 63

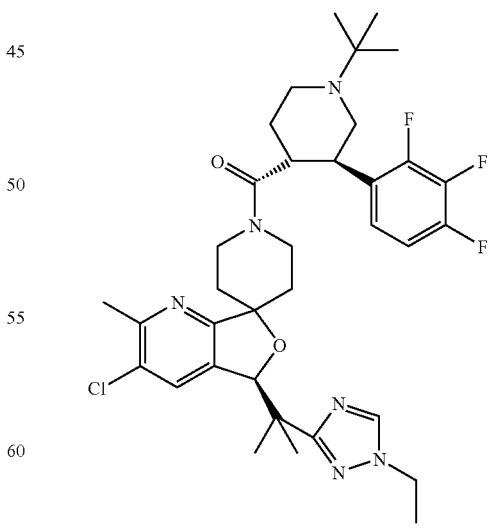

Example 63-D2 was prepared using an analogous procedure to that used to prepare the Example 60; (m/z (ES) (M+H)$^+$=673).

Example 64
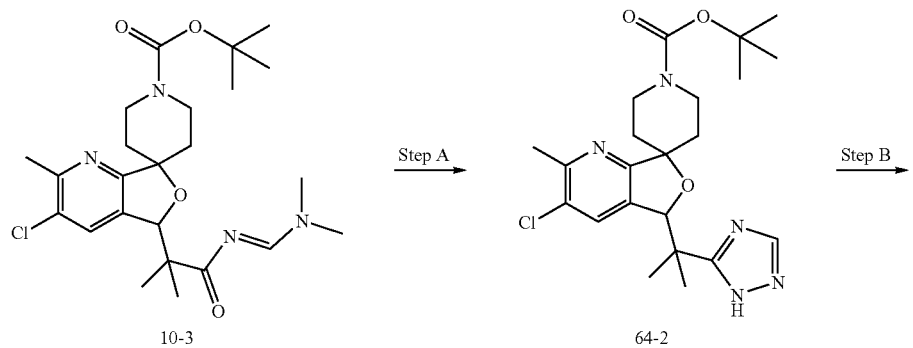
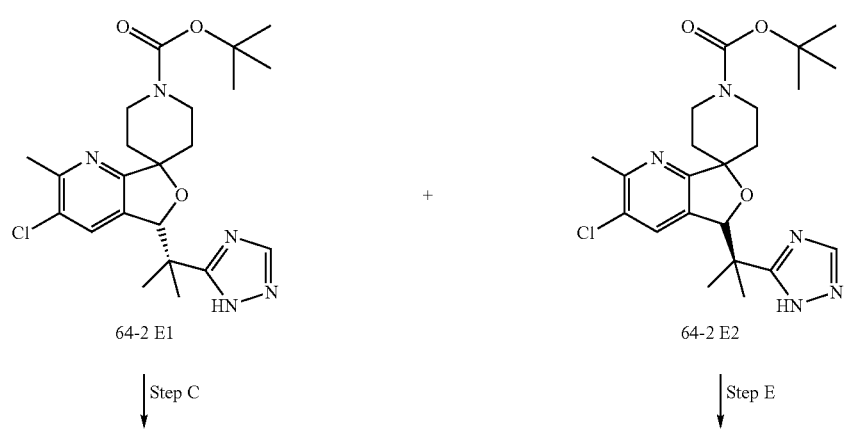
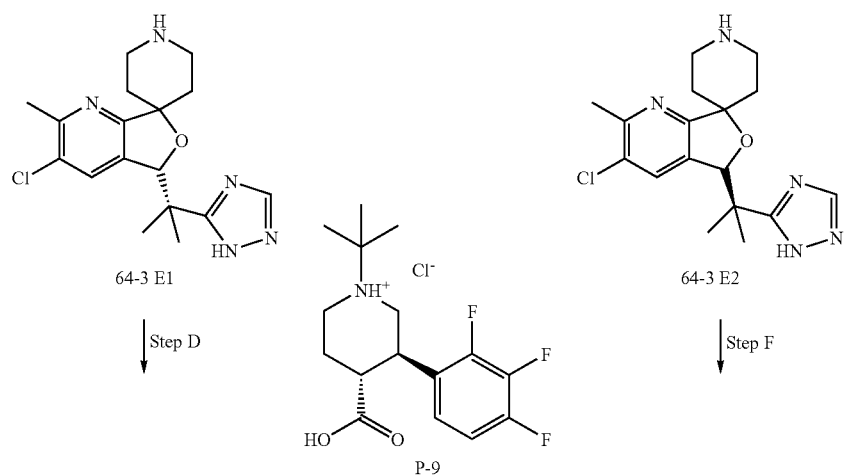

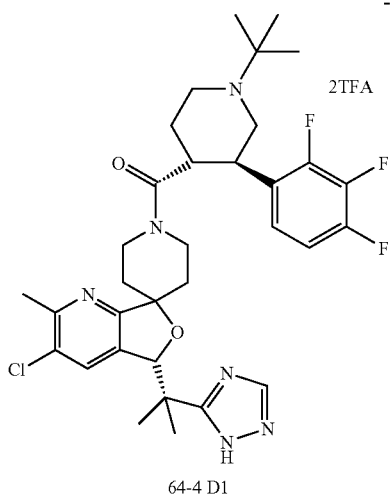

64-4 D1

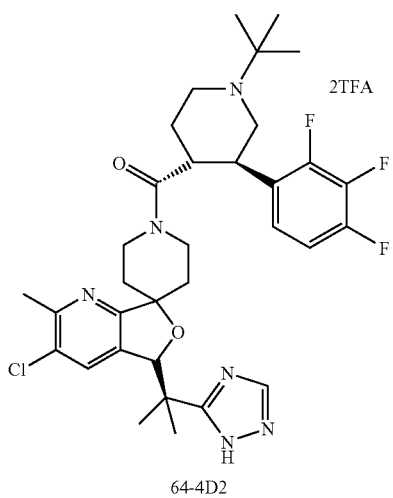

64-4D2

Step A: A 50 mL one neck round bottom flask was charged with 10-3 (94 mg, 0.196 mmol) along with HOAc (3 mL). The mixture was cooled to 0° C. in an ice-water bath. Hydrazine (98%, 12 mg, 1.069 mmol) was then added dropwise over 2 min. The resulting reaction mixture was stirred and gradually heated to 95° C. for 1 hour. After cooling to room temperature, the solvent was removed by rotary evaporation. The resulting residue was then partitioned between ethyl acetate (10 ml) and NaHCO$_3$ (sat, 60 mL). The organic layer was separated and the aqueous layer was extracted with ethyl acetate (3×10 mL). The combined organic phases were washed with water, brine, dried over MgSO$_4$, filtered and concentrated. The resulting residue was then purified by Prep TLC (2000 μm, ethyl acetate:hexanes=2:3) to afford product 64-2 (m/z (ES) (M+H)$^+$=448) as a racemic mixture.

Step B: The racemic mixture of 64-2 in Step A was separated with chiral AD column using 7% ethanol in heptane to afford product 64-2 E1 (100% ee, Rt=by chiral AD column using 7% ethanol in heptane) and 64-2 E2 (100% ee, Rt=by Chiral AD column using 7% ethanol in heptane).

Step C: A mixture of compound 64-2 E1 (0.022 g, 0.049 mmol) and concentrated HCl (0.5 mL) in methanol (1 mL) was stirred at 40° C. for 30 min. The mixture was then concentrated and the resulting residue was co-evaporated with toluene three times to afford compound 64-3 E1.

Step D: To a mixture of compound 64-3 E1 (0.049 mmol), acid P-9 (0.022 g, 0.064 mmol) and Hunig's base (0.031 g, 0.245 mmol) was added HOAT (0.007 g, 0.049 mmol) and HATU (0.022 g, 0.059 mmol). The resulting reaction mixture was stirred at room temperature for 2 hours, then concentrated. The resulting residue was dissolved in methanol (1 mL), filtered through a syringe and washed with methanol (2 mL). The filtrate was concentrated and the resulting residue was purified by RP HPLC (YMC column, 20% to 80% acetonitrile in water) to afford compound 64-4 DI (m/z (ES) (M+H)$^+$=645) as the TFA salt.

Step E: A procedure similar to the procedure of Step C was used for the preparation of 64-3 E2 (m/z (ES) (M+H)$^+$=348)

Step F: A procedure similar to the procedure of Step D was used for the preparation of 64-4D2 (m/z (ES) (M+H)$^+$=645).

Example 65

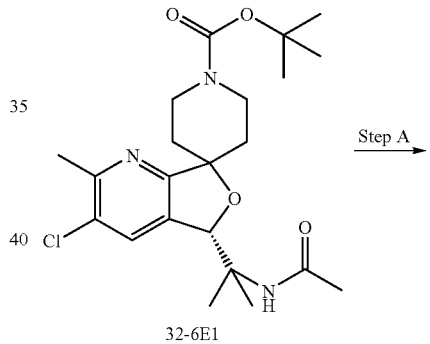

32-6E1

Step A

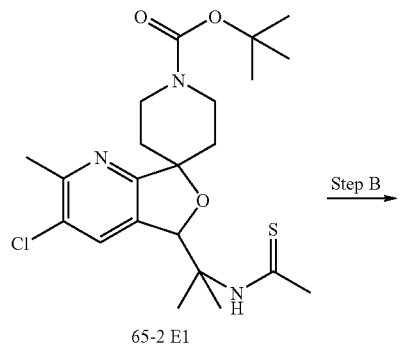

65-2 E1

Step B

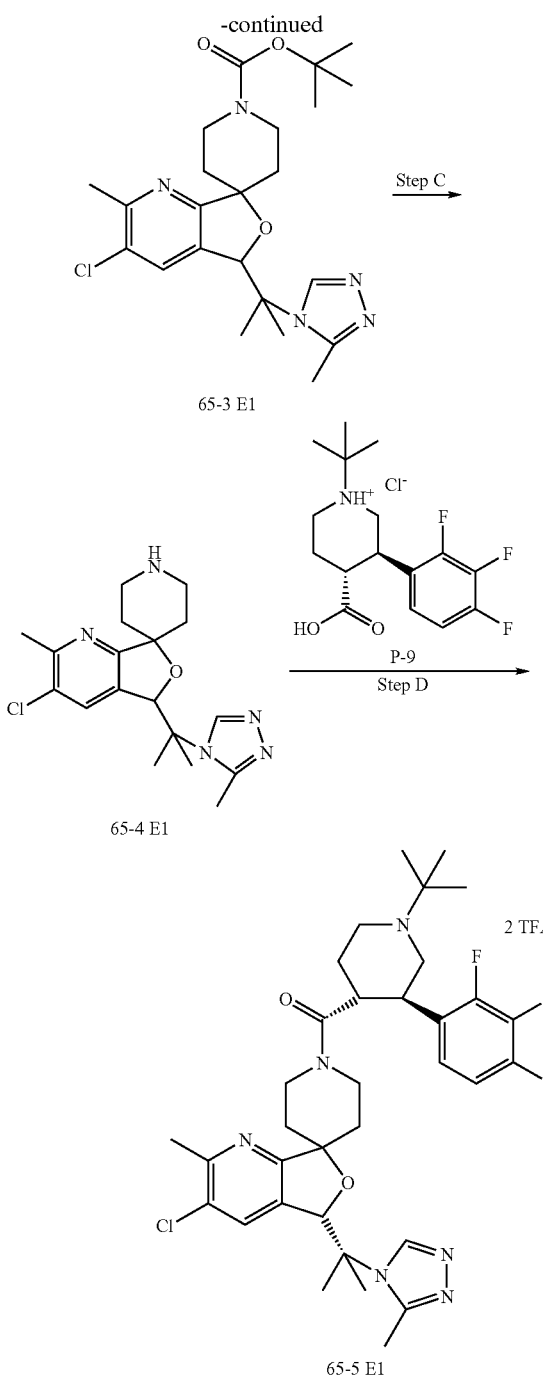

65-3 E1

65-4 E1

65-5 E1

Step A: To a 25 mL one neck round bottom flask was charged 32-6 E1 (101 mg, 0.23 mmol), Lawesson's reagent (93 mg, 0.231 mmol) and toluene (10 mL). The resulting reaction mixture was stirred under nitrogen at 100° C. for 1 hour. The reaction mixture was then cooled to room temperature and quenched with water (10 mL). The organic layer was separated and the aqueous layer was extracted by ethyl acetate (3×5 ml). The combined organic phases were washed with water, brine, dried over MgSO$_4$, filtered and concentrated. The resulting residue was purified by Prep TLC (2000 μm, 20% ethyl acetate in hexanes) to afford foamy solid product 65-2 E1 (Rf=0.2 by ethyl acetate:hexanes=1:4, m/z (ES) (M+H)$^+$=454).

Step B: To a 25 mL round bottom flask was charged 65-2 E1 (99 mg, 0.218 mmol), anhydrous acetonitrile (2 mL), acetyl hydrazide (52 mg, 0.872 mmol), followed by mercury acetate (264 mg, 0.829 mmol). The resulting reaction mixture was then stirred at room temperature for two days, then filtered through a syringe and washed with acetonitrile (3×2 mL). The filtrate was concentrated and the residue was purified by Prep TLC (2000 μm, ethyl acetate:hexanes=3:2) to afford product 65-3-E1 (Rf=0.1 by ethyl acetate:hexanes=3:2, m/z (ES) (M+H)$^+$=462).

Step C: A mixture of compound 65-3E1 (0.025 g, 0.054 mmol) and concentrated HCl (0.5 mL) in methanol (1 mL) was stirred at 40° C. for 30 min. The mixture was then concentrated and the resulting residue was co-evaporated with toluene three times to afford compound 65-4 E1.

Step D: To a mixture of compound 65-4 E1 (0.054 mmol), acid P-9 (0.021 g, 0.060 mmol) and Hunig's base (0.035 g, 0.271 mmol) was added HOAT (0.008 g, 0.060 mmol) and HATU (0.025 g, 0.065 mmol). The resulting reaction mixture was stirred at room temperature for 2 hours, then concentrated. The resulting residue was dissolved in methanol (1 mL), filtered through a syringe and washed with methanol (2 mL). The filtrate was concentrated and the resulting residue was purified by RP HPLC (YMC column, 20% to 80% acetonitrile in water) to afford the TFA salt of compound 65-5 DI (m/z (ES) (M+H)$^+$=659).

Example 66

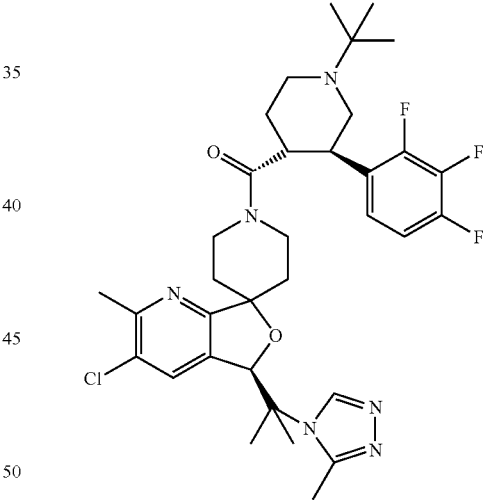

66-D2

66-D2 was prepared using a procedure analogous to the procedure used to prepare 65-5D1; (m/z (ES) (M+H)$^+$=659).

Example 67

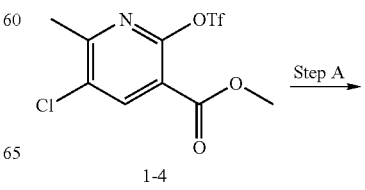

1-4

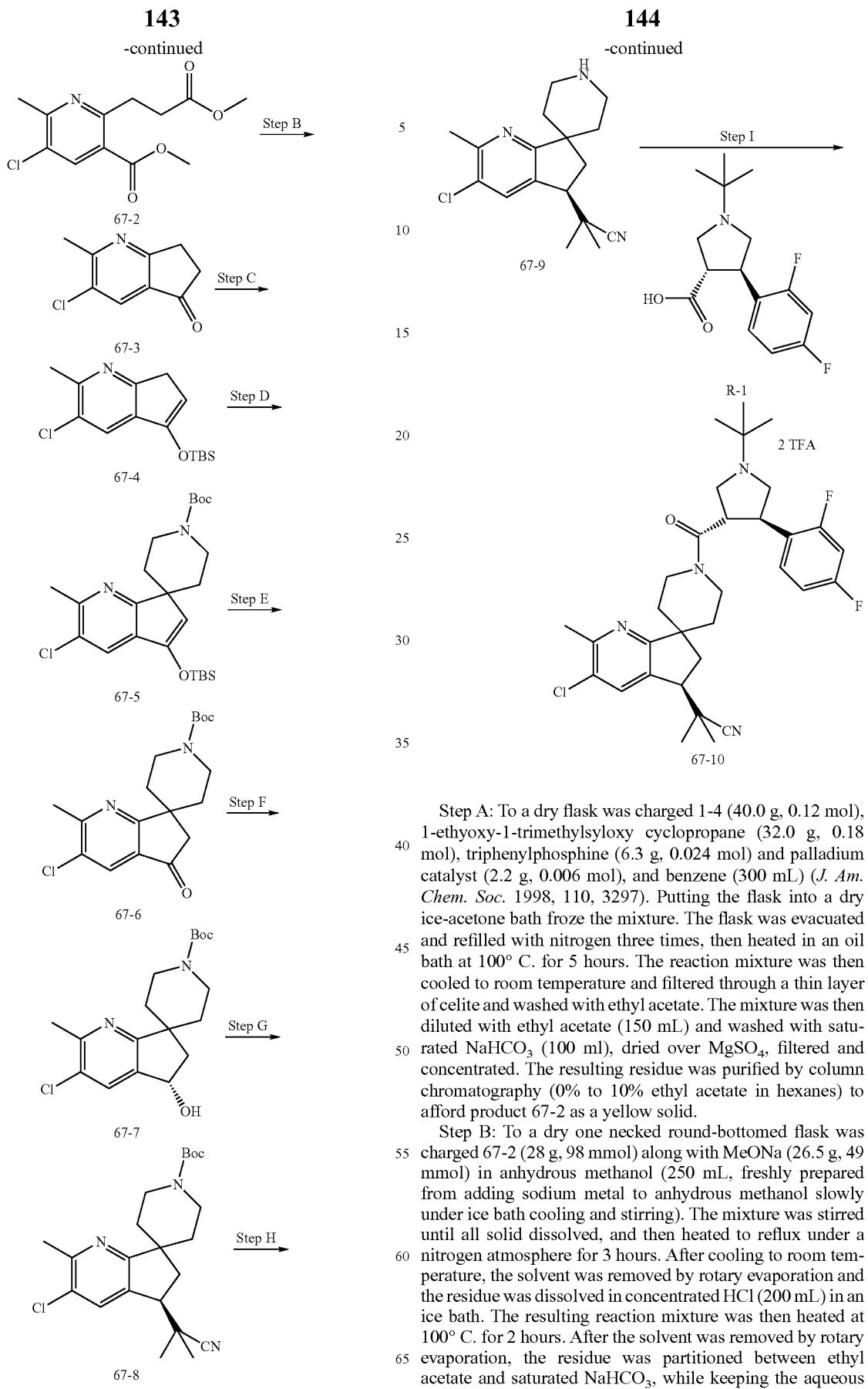

Step A: To a dry flask was charged 1-4 (40.0 g, 0.12 mol), 1-ethyoxy-1-trimethylsyloxy cyclopropane (32.0 g, 0.18 mol), triphenylphosphine (6.3 g, 0.024 mol) and palladium catalyst (2.2 g, 0.006 mol), and benzene (300 mL) (*J. Am. Chem. Soc.* 1998, 110, 3297). Putting the flask into a dry ice-acetone bath froze the mixture. The flask was evacuated and refilled with nitrogen three times, then heated in an oil bath at 100° C. for 5 hours. The reaction mixture was then cooled to room temperature and filtered through a thin layer of celite and washed with ethyl acetate. The mixture was then diluted with ethyl acetate (150 mL) and washed with saturated NaHCO$_3$ (100 ml), dried over MgSO$_4$, filtered and concentrated. The resulting residue was purified by column chromatography (0% to 10% ethyl acetate in hexanes) to afford product 67-2 as a yellow solid.

Step B: To a dry one necked round-bottomed flask was charged 67-2 (28 g, 98 mmol) along with MeONa (26.5 g, 49 mmol) in anhydrous methanol (250 mL, freshly prepared from adding sodium metal to anhydrous methanol slowly under ice bath cooling and stirring). The mixture was stirred until all solid dissolved, and then heated to reflux under a nitrogen atmosphere for 3 hours. After cooling to room temperature, the solvent was removed by rotary evaporation and the residue was dissolved in concentrated HCl (200 mL) in an ice bath. The resulting reaction mixture was then heated at 100° C. for 2 hours. After the solvent was removed by rotary evaporation, the residue was partitioned between ethyl acetate and saturated NaHCO$_3$, while keeping the aqueous layer basic (pH8). The organic layer was separated and aqueous layer was extracted by ethyl acetate (3×100 mL). The combined organic phases were washed with brine, dried over MgSO$_4$, filtered and concentrated. The resulting residue was purified by column chromatography (10-30% ethyl acetate in hexanes) to afford product 67-3 as a white solid.

Step C: To a solution of tert-butyldimethylchlorosilane (14.9 g, 99.1 mmol) and compound 67-3 (15 g, 82.6 mmol) in benzene (150 mL) was added DBU (16.4 g, 107.4 mmol). The resulting mixture was stirred at room temperature for 2 hours; then concentrated and purified by column chromatography (0 to 10% ethyl acetate in hexanes) to afford product 67-4.

Step D: To a dry one necked round bottom flask was charged HMDS (23 g, 143.8 mmol) and dry THF (150 mL) and cooled to 0° C. 58 mL of n-BuLi (2.5 M in hexanes) was added and the mixture was stirred at 0° C. for 1 h. Then 17 g of 67-4 in THF (30 mL) were added and the mixture was stirred for 1 h, followed by the addition of 21 g of tert-butyl bis(2-chloroethyl)carbamate in THF (20 mL). The resulting mixture was slowly warmed to room temperature and stirred overnight. To the mixture was added water (50 mL). The organic layer was separated and aqueous layer was extracted by ethyl acetate (3×50 mL). The combined organic phases were washed with brine, dried over MgSO$_4$, filtered and concentrated to afford product 67-5, which was used directly to next step without further purification.

Step E: To a solution of 67-5 (22.5 g, 48.4 mmol) in dry THF was added TBAF (19.0 g, 72.6 mmol) at room temperature, and the resulting mixture was stirred overnight. The mixture was then concentrated and purified by column chromatography to afford product 67-6 as a white solid.

Step F: To a solution of borane diethylaniline complex (3.02 g, 18.55 mmol) and (R)-MeCBS (0.773 mL, 1M) in THF (30 mL) at 40° C. was added a solution of 67-6 (5.42 g, 15.46 mmol) in THF (30 mL) dropwise via syringe dropwise over 20 min. The resulting reaction mixture was then stirred at 40° C. for 2 hours and then overnight at room temperature. The reaction mixture was then cooled to room temperature and quenched by slow addition of methanol (5 mL), and then diluted with water (50 mL). The organic layer was separated and the aqueous layer was extracted with ethyl acetate (3×100 mL). The combined organic phases were washed with water, brine, dried over MgSO$_4$, filtered and concentrated. The resulting residue was purified by MPLC (120 g silica gel, 0 to 40% ethyl acetate in hexanes) to afford product 67-7 as a white solid (Rf=0.15 by ethyl acetate:hexanes=1:4, m/z (ES) (M+H)$^+$=353; 99% ee).

Step G: A 500 mL round bottom flask was charged with 67-7 (5.17 g, 14.65 mmol) and THF (30 mL). The mixture was cooled to −15° C., then isobutyl nitrile (3.04 g, 44.0 mmol) and diethyl phosphoryl chloride (3.79 g, 21.98 mmol) were added. Then a solution of LiHMDS (65.9 mL) in THF (1M) was added dropwise by syringe over 20 min, and the reaction mixture was stirred at −15° C. for 1 hour. The reaction was quenched with water (30 mL). The organic layer was separated and the aqueous layer was extracted with ethyl acetate (3×10 mL). The combined organic phases were washed with water, brine, dried over MgSO$_4$, filtered and concentrated. The resulting residue was purified by MPLC (120 g, 0-40% ethyl acetate in hexanes) to afford product 67-8 as a white solid (Rf=0.15 by ethyl acetate:hexanes=1:4, m/z (ES) (M+H)$^+$=404; 94% ee).

Step H: A mixture of compound 67-8 (0.039 g, 0.097 mmol) and concentrated HCl (0.5 mL) in methanol (1 mL) was stirred at 40° C. for 30 min. The mixture was then concentrated and the residue was co-evaporated with toluene three times to afford compound 67-9 (m/z (ES) (M+H)$^+$=303).

Step I: To a mixture of compound 67-9 (0.097 mmol), acid R-1 (0.030 g, 0.106 mmol) and Hunig's base (0.062 g, 0.483 mmol) was added HOAT (0.014 g, 0.106 mmol) and HATU (0.044 g, 0.116 mmol). The resulting reaction mixture was stirred at room temperature for 2 hours, then concentrated. The resulting residue was dissolved in methanol (1 mL), filtered through a syringe, and washed with methanol (2 mL). The filtrate was concentrated and the resulting residue was purified by RP HPLC (YMC column, 20% to 80% acetonitrile in water) to afford the TFA salt of compound 67-10 (m/z (ES) (M+H)$^+$=569).

Following a procedure analogous to the procedure described in Example 67, and using the appropriate reagents, the following compounds were prepared:

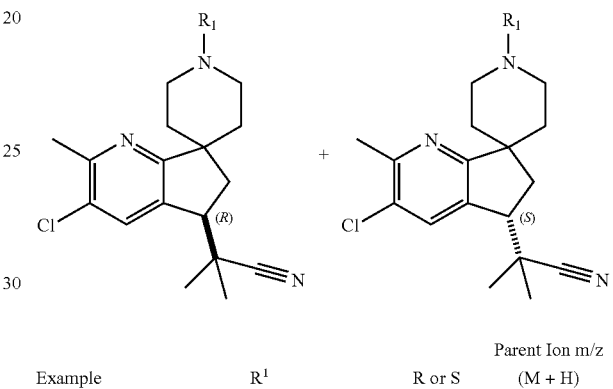

| Example | R$^1$ | R or S | Parent Ion m/z (M + H) |
|---|---|---|---|
| 68 | 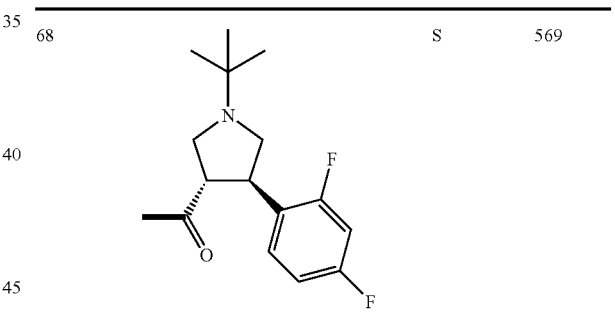 | S | 569 |
| 69 | 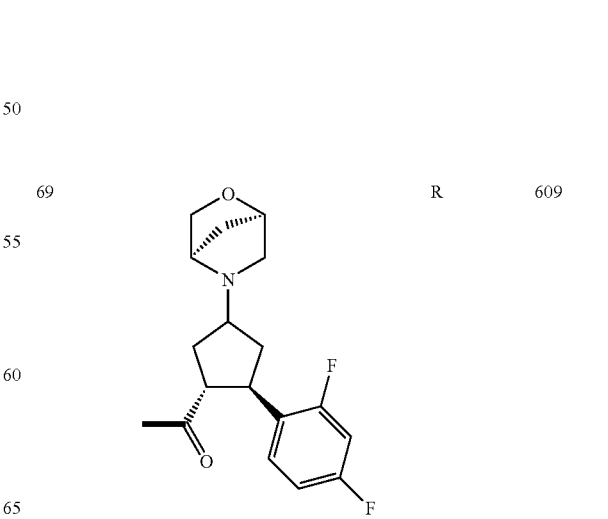 | R | 609 |

147
-continued
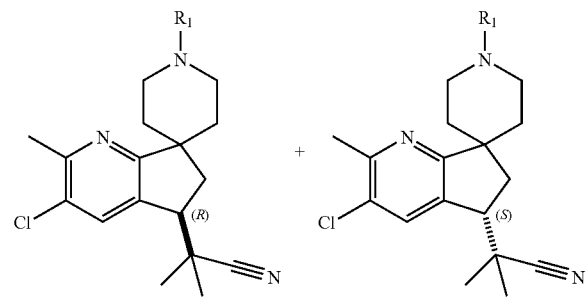
| Example | R¹ | R or S | Parent Ion m/z (M + H) |
|---|---|---|---|
| 70 | 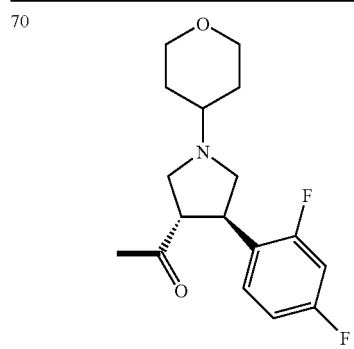 | R | 597 |
| 71 | 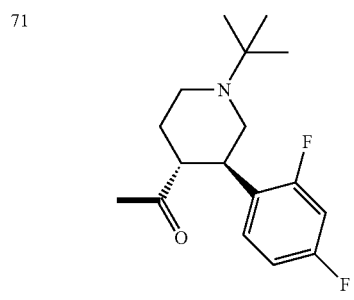 | R | 583 |
| 72 | 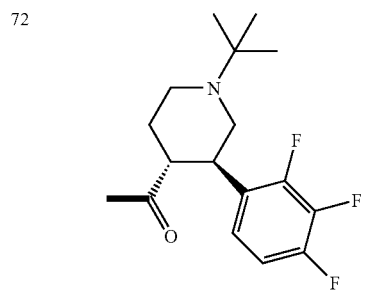 | R | 601 |
| 73 | 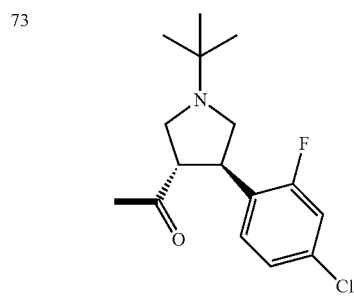 | R | 585 |
148
-continued
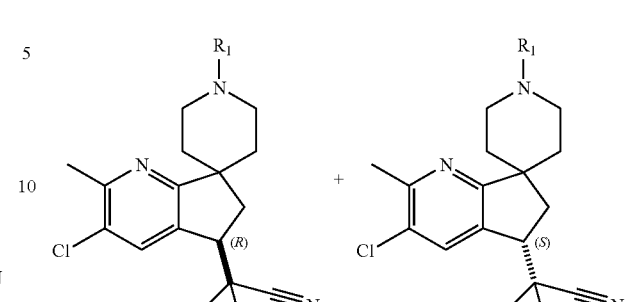
| Example | R¹ | R or S | Parent Ion m/z (M + H) |
|---|---|---|---|
| 74 | 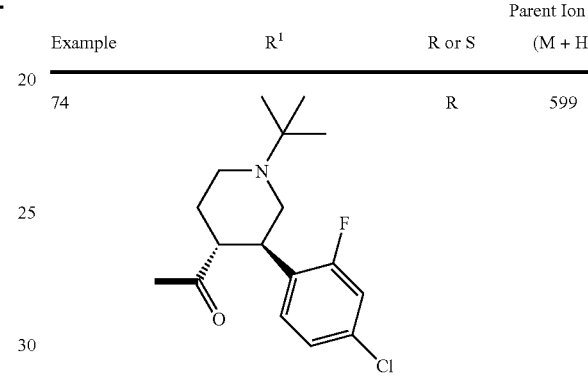 | R | 599 |
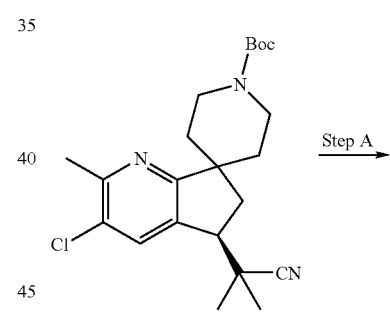
67-8
Step A →
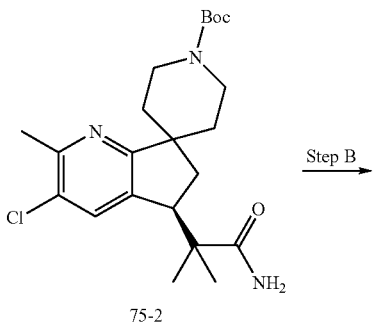
75-2
Step B →

-continued

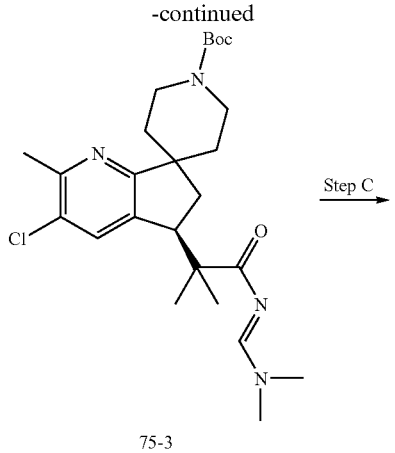

75-3

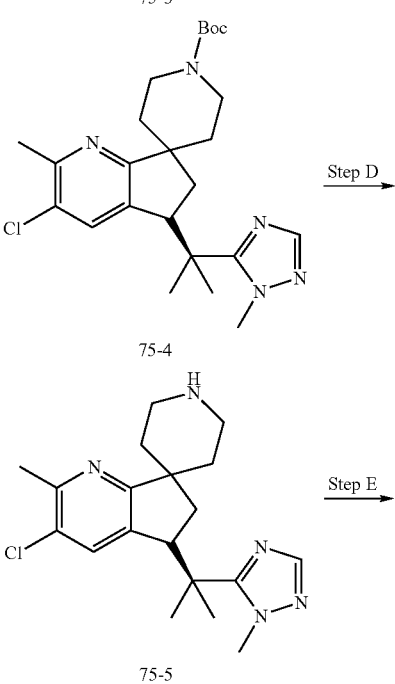

75-4

75-5

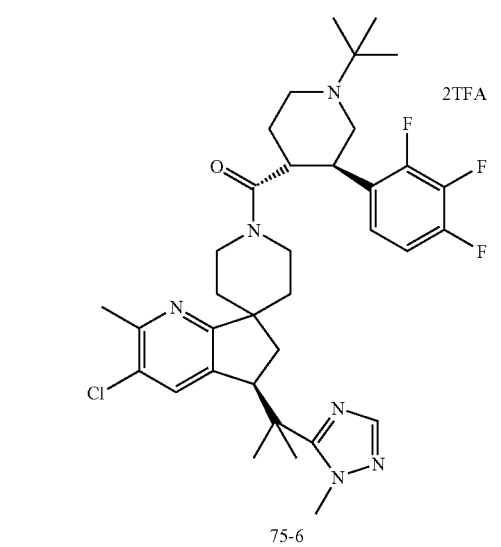

75-6

Step A: To a 150 mL sealed vessel was charged with 67-8 (5.36 g, 13.27 mmol) along potassium hydroxide (7.44 g, 133 mmol), 1-butanol (40 mL) and water (10 mL). The vessel was flushed with nitrogen and sealed with screw cap, and the reaction mixture was heated in an oil bath at 145° C. for 5 hours. The mixture was then diluted with ethyl acetate (100 mL). The aqueous layer was separated and the organic phase was washed with water, brine, dried over MgSO$_4$, filtered and concentrated to afford product 75-2 (m/z (ES) (M+H)$^+$=422), which was used in the next step without further purification.

Step B: To a 500 mL one neck round bottom flask was charged with 75-2 (5.6 g, 13.27 mmol) and DMF-DMA (15.81 g, 133 mmol). The flask was flushed with nitrogen and the resulting reaction mixture was heated in an oil bath at 120° C. for 1 hour under nitrogen. After cooling to room temperature, the excess DMF-DMA was removed by rotary evaporation and the resulting residue was dried by co-evaporation with toluene three times. The crude 75-3 was used in the next step without further purification.

Step C: To a 500 mL one neck round bottom flask was charged with 75-3 (6.33 g, 13.27 mmol) and acetic acid (30 mL). The mixture was cooled to 0° C. in an ice-water bath, and methyl hydrazine (1.222 g, 26.54 mmol) was added dropwise over 2 min. The resulting reaction mixture was gradually heated to 95° C. for 1 hour. After cooling to room temperature, the solvent was removed by rotary evaporation. The resulting residue was then partitioned between ethyl acetate (100 ml) and saturated NaHCO$_3$ (60 mL). The organic layer was separated and the aqueous layer was extracted with ethyl acetate (3×100 mL). The combined organic phases were washed with water, brine, dried over MgSO$_4$, filtered and concentrated. The residue was then purified by MPLC (120 g silca gel, 20 to 60% ethyl acetate in hexanes) to afford product 75-4 as a foamy solid (Rf=0.2 by ethyl acetate:hexanes=2:3, 85% ee, Rt=9.4 min on Chiral AD-H column by 10% EtOH in Heptane, m/z (ES) (M+H)$^+$=460; which was later enhanced to 100% ee chiral HPLC).

Step D: A mixture of compound 75-4 (0.020 g, 0.043 mmol) and concentrated HCl (0.5 mL) in methanol (1 mL) was stirred at 40° C. for 30 min. The mixture was then concentrated and the residue was co-evaporated with toluene three times to afford compound 75-5 (m/z (ES) (M+H)$^+$=360).

Step E: To a mixture of compound 75-5 (0.043 mmol), acid P-9 (0.018 g, 0.052 mmol) and Hunig's base (0.028 g, 0.217 mmol) was added HOAT (0.007 g, 0.048 mmol) and HATU (0.020 g, 0.052 mmol). The resulting reaction mixture was stirred at room temperature for 2 hours, then concentrated. The resulting residue was dissolved in methanol (1 mL), filtered through a syringe and washed with methanol (2 mL). The filtrate was concentrated and the resulting residue was purified by RP HPLC(YMC column, 20% to 80% acetonitrile in water) to afford the TFA salt of compound 75-6 (m/z (ES) (M+H)$^+$=657).

Following a procedure analogous to the procedure described in Example 75, and using the appropriate reagents, the following compounds were prepared:
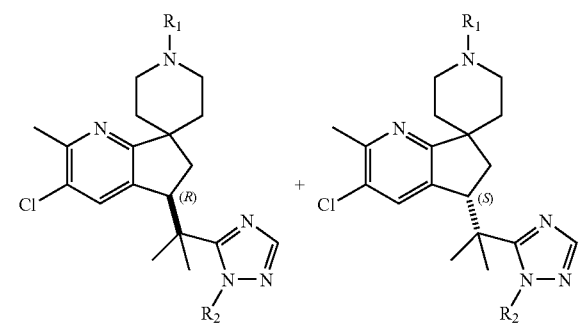
| Example | R$_1$ | R$_2$ | R or S | Parent Ion m/z (M + H) |
|---|---|---|---|---|
| 76 | 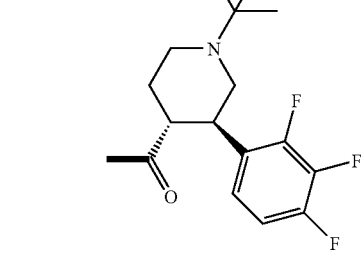 | Me | S | 657 |
| 77 | 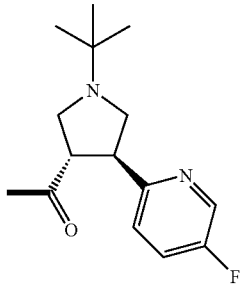 | Me | R | 608 |
| 78 | 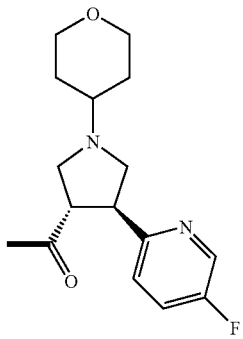 | Me | R | 635 |
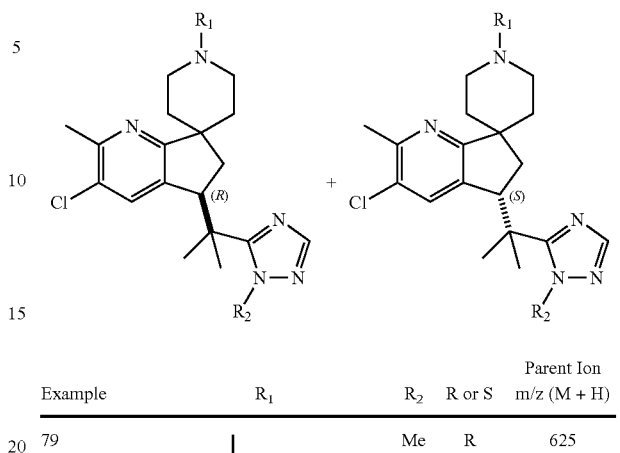
| Example | R$_1$ | R$_2$ | R or S | Parent Ion m/z (M + H) |
|---|---|---|---|---|
| 79 | 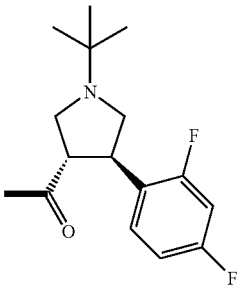 | Me | R | 625 |
| 80 | 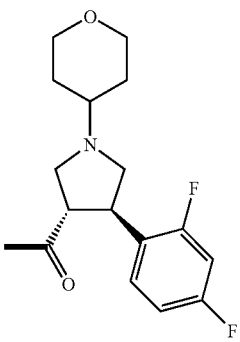 | Me | R | 653 |
| 81 | 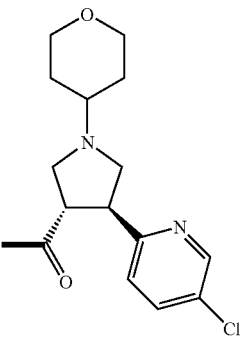 | Me | R | 669 |

-continued

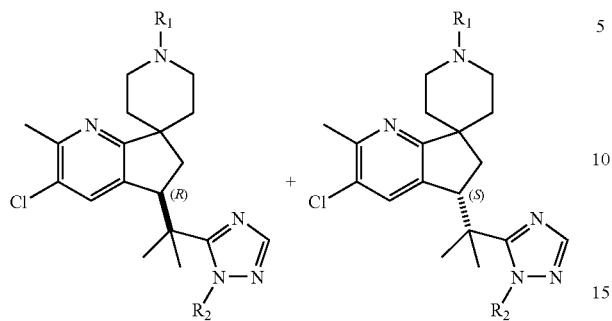

| Example | R₁ | R₂ | R or S | Parent Ion m/z (M + H) |
|---------|-----|-----|--------|------------------------|
| 82 | <image showing tert-butyl piperidine with trifluorophenyl ketone> | H | R | 643 |
| 83 | <image showing tert-butyl piperidine with trifluorophenyl ketone> | H | S | 643 |

Example 84

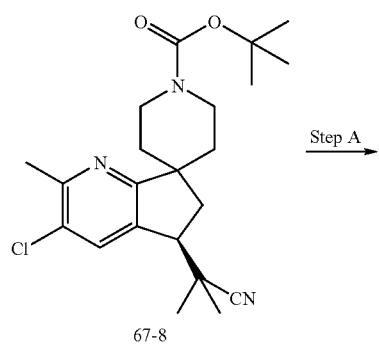

-continued

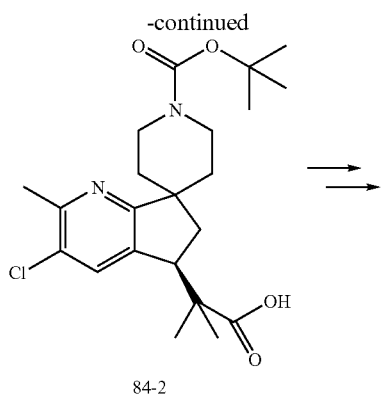

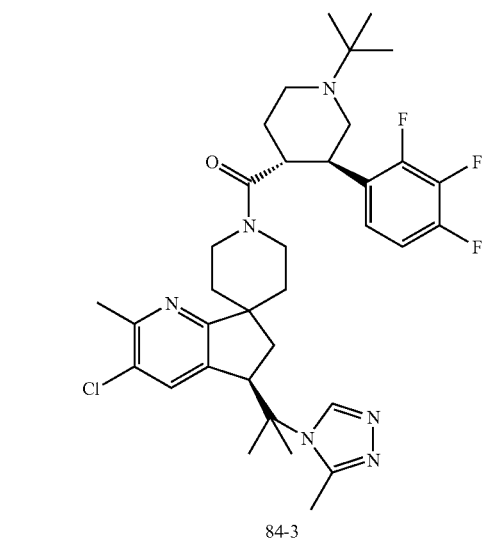

Step A: 67-8 (400 mg, 0.990 mmol) was charged in a sealed vessel (75 mL) along with concentrated HCl (6 mL) and sealed with a screw cap. The mixture was heated in an oil bath of 110° C. for 24 hours, then transferred to a 100 mL one neck round bottom flask and diluted with ethyl acetate (20 mL). The aqueous layer was basified with NaOH (5N) to pH ~9 and then Boc₂O (259 mg, 1.188 mmol) was added. The mixture was stirred at room temperature for 30 minutes and the organic phase was separated. The aqueous layer was extracted with ethyl acetate (3×20 mL). The combined organic phases were washed with water, brine, dried over MgSO₄, filtered and concentrated to afford product 84-2 (m/z (ES) (M+H)$^+$=423) which was used directly to next step without further purification.

Following the procedure of Examples 32 and 65, compound 84-3 was prepared (m/z (ES) (M+H)⁺=657).

Example 85

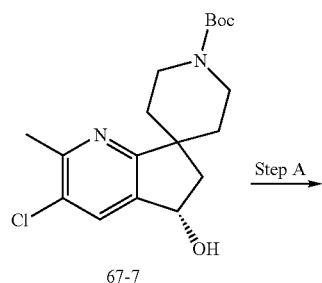
67-7

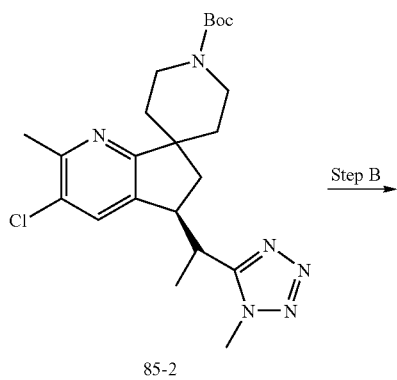
85-2

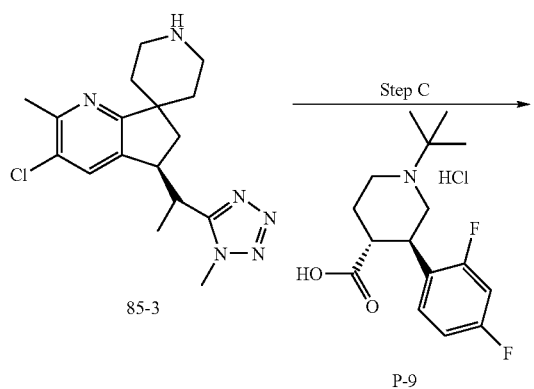
85-3    P-9

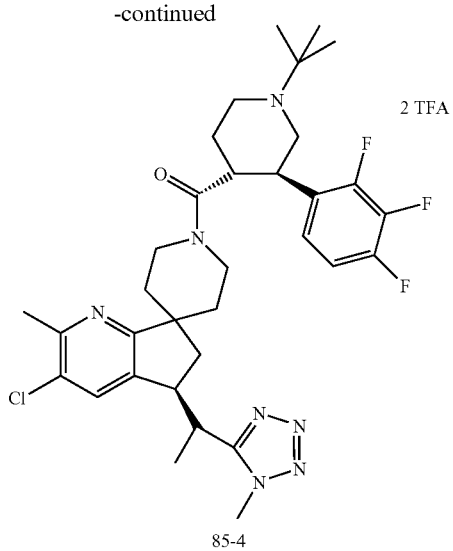
85-4

Step A: A 25 mL round bottom flask was charged with compound 67-7 (0.092 g, 0.261 mmol) and THF (2 mL). The mixture was then cooled to −15° C., then 1-methyl-5-ethyl tetrazole (0.088 g, 0.782 mmol) and diethyl phosphoryl chloride (0.067 g, 0.391 mmol) were added. Then a solution of LiHMDS (1.17 mL) in THF (1M) was added dropwise by syringe over 20 min. The resulting reaction mixture was then stirred at −15° C. for 1 hour. The reaction was then quenched with water (5 mL). The organic layer was separated and the aqueous layer was extracted with ethyl acetate (3×10 mL). The combined organic phases were washed with brine, dried over MgSO₄, filtered and concentrated. The residue was purified MPLC (6 g silica gel, 0 to 40% ethyl acetate in hexanes) to afford product 85-2 as a white solid (m/z (ES) (M+H)⁺= 447).

Step C: A mixture of compound 85-2 (0.035 g, 0.078 mmol) and concentrated HCl (0.5 mL) in methanol (1 mL) was stirred at 40° C. for 30 min. The mixture was then concentrated and the residue was co-evaporated with toluene three times to afford compound 85-3 (m/z (ES) (M+H)⁺= 347).

Step E: To a mixture of compound 85-3 (0.078 mmol), acid P-9 (0.039 g, 0.110 mmol) and Hunig's base (0.051 g, 0.392 mmol) was added HOAT (0.011 g, 0.078 mmol) and HATU (0.036 g, 0.094 mmol). The resulting reaction mixture was stirred at room temperature for 2 hours, then concentrated. The resulting residue was dissolved in methanol (1 mL), filtered through a syringe and washed with methanol (2 mL). The filtrate was concentrated and the resulting residue was purified by RP HPLC (YMC column, 20% to 80% acetonitrile in water) to afford the TFA salt of compound 85-4 (m/z (ES) (M+H)⁺=644).

Example 86

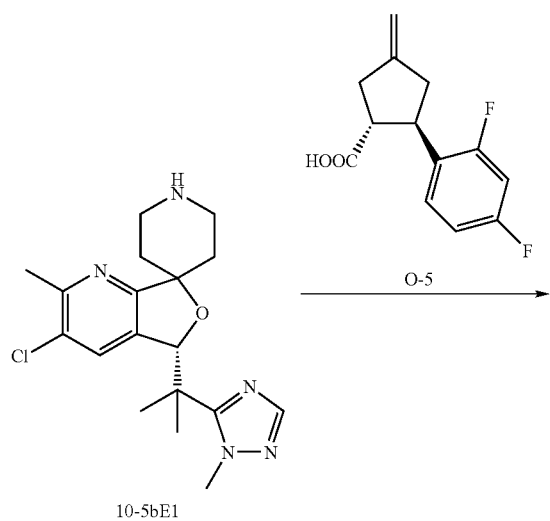

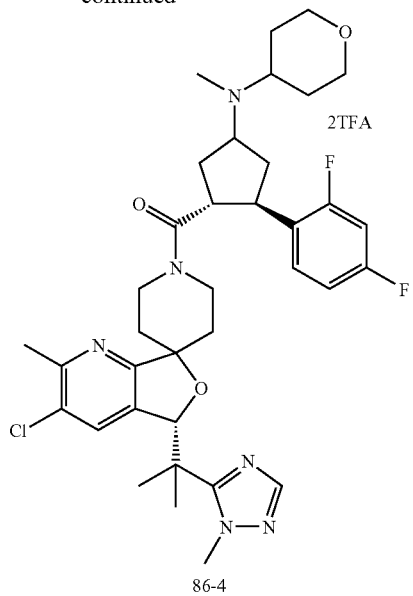

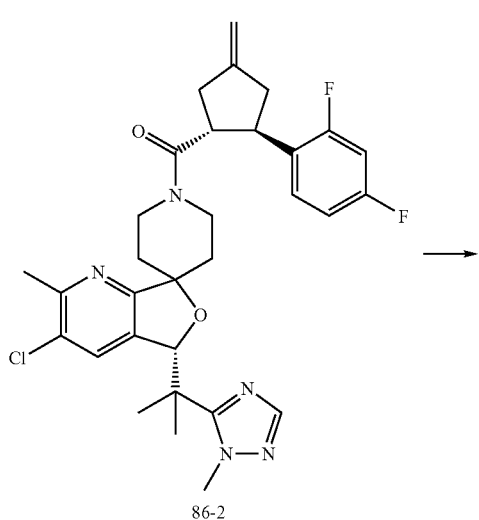

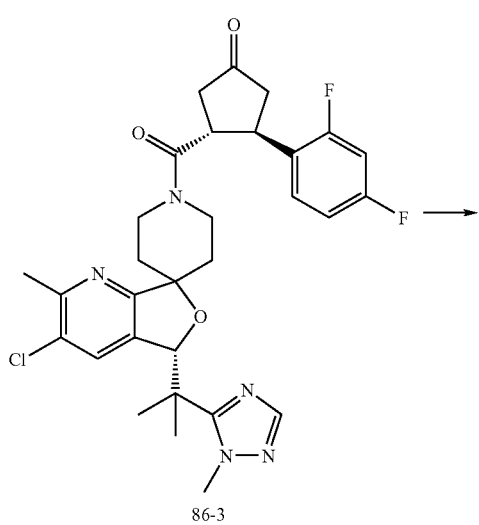

Step A: 10-5bE1 (0.081 g, 0.225 mmol) was charged to a 20 mL round bottomed flask along with acid O-5 (0.059 g, 0.248 mmol), methylene chloride (2 mL) and Hunig's base (0.087 g, 0.68 mmol). The mixture was stirred until the solid dissolved. Then HATU (0.103 g, 0.27 mmol) and HOAT (0.034 g, 0.248 mmol) were added and the reaction mixture was stirred at room temperature for 2 hours. The reaction mixture was then filtered and concentrated and the resulting residue was purified by Prep TLC (2000 μm, ethyl acetate:hexanes=3:2) to afford product 86-2 (m/z (ES) (M+H)$^+$=583).

Step B: To a 25 mL one necked round bottomed flask was charged 86-2 (0.130 g, 0.223 mmol) and THF/H$_2$O (1.5/1.5 mL), followed by osmium tetroxide (0.15 mL, 1M). The mixture was stirred at room temperature for 30 min. Then sodium periodate solution (0.248 g, 1.15 mmol) was added dropwise. The resulting mixture was stirred at room temperature for 2 hours. The reaction mixture was quenched with saturated Na$_2$S$_2$O$_3$ solution and stirred for 20 min. Then the reaction mixture was extracted with ethyl acetate (3×50 mL). The combined organic phases were washed with water, brine, dried over MgSO$_4$, filtered and concentrated to afford product 86-3 (m/z (ES) (M+H)$^+$=585), which was used in next step without further purification.

Step C: A 25 mL round bottom flask were charged with 86-3 (0.022 g, 0.038 mmol), methylene chloride (2 mL), N-methyl-N-tetrahydro-2H-pyran-4-ylamine (0.009 g, 0.56 mmol), sodium triacetoxyborohydride (0.032 g, 0.15 mmol), molecular sieves (20 mg) and triethyl amine (0.019 g, 0.188 mmol). The mixture was stirred at room temperature for 12 hours. The reaction mixture was quenched with MeOH and stirred for 20 minutes, then filtered and concentrated. The resulting residue was purified by RP HPLC (YMC column, 20% to 80% acetonitrile in water) to afford product 86-4 as a TFA salt (m/z (ES) (M+H)$^+$=683).

Following a procedure analogous to the procedure of Example 86, and using appropriate reagents and starting materials, the following compounds were prepared:

| Example | R2 | R3 | R1 | Parent Ion m/z (M + H) |
|---|---|---|---|---|
| 87 | Me | Cl | (oxa-azabicyclic, N-Me) | 667 |
| 88 | Me | Cl | (3-fluoropyrrolidine, N-Me) | 657 |
| 89 | Me | Me | (N-Me-tetrahydropyran-4-yl-amine) | 663 |
| 90 | CF$_3$ | H | (N-Me-tetrahydropyran-4-yl-amine) | 703 |
| 91 | H | Me | (N-Me-tetrahydropyran-4-yl-amine) | 649 |
| 92 | Me | F | (N-Me-tetrahydropyran-4-yl-amine) | 667 |
| 93 | Me | F | (oxa-azabicyclic, N-Me) | 651 |

Following a procedure analogous to the procedure of Example 11, and using appropriate reagents and starting materials, the following compounds were prepared:

| Example | R1 | R2 | D1 or D2 | Parent Ion m/z (M + H) |
|---|---|---|---|---|
| 94 | t-Butyl | (5-fluoropyridin-2-yl) | D1 | 610 |

-continued

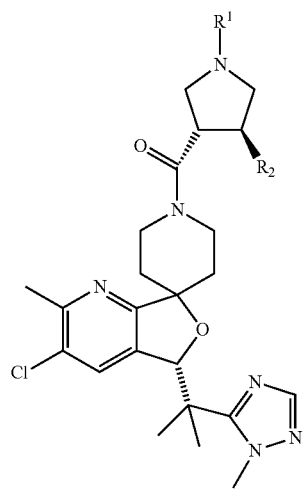

| Example | R1 | R2 | D1 or D2 | Parent Ion m/z (M + H) |
|---|---|---|---|---|
| 95 | 4-tetrahydro pyran | 5-chloropyridin-2-yl | D1 | 654 |
| 96 | 4-tetrahydro pyran | 5-fluoropyridin-2-yl | D1 | 638 |
| 97 | pyrimidin-2-yl | 2,4-difluorophenyl | D1 | 649 |
| 98 | pyridin-2-yl | 2,4-difluorophenyl | D1 | 648 |
| 99 | pyrazin-2-yl | 2,4-difluorophenyl | D1 | 649 |
| 100 | 3,6-dimethylpyridazin-yl | 2,4-difluorophenyl | D1 | 663 |

BIOLOGICAL ASSAYS

A. Binding Assay

The membrane binding assay was used to identify competitive inhibitors of $^{125}$I-NDP-alpha-MSH binding to cloned human MCRs expressed in mouse L- or Chinese hamster ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BR1); 100 mL 10% heat-inactivated fetal bovine serum (Sigma); 10 mL 10,000 unit/mL penicillin & 10,000 µg/mL streptomycin (Gibco/BR1); 10 mL 200 mM L-glutamine (Gibco/BR1); 1 mg/mL geneticin (G418) (Gibco/BR1). The cells were grown at 37° C. with $CO_2$ and humidity control until the desired cell density and cell number was obtained.

The medium was poured off and 10 mL/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mL/monolayer membrane preparation buffer having the composition: 10 mM Tris pH 7.2-7.4; 4 Ag/mL Leupeptin (Sigma); 10 µM Phosphoramidon (Boehringer Mannheim); 40 µg/mL Bacitracin (Sigma); 51 g/mL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mL/monolayer membrane prep buffer and aliquots were placed in tubes (500-1000 µL/tube) and quick frozen in liquid nitrogen and then stored at −80° C.

Test compounds or unlabelled NDP-A-MSH was added to 100 µL of membrane binding buffer to a final concentration of 1 µM. The membrane binding buffer had the composition: 50 mM Tris pH 7.2; 2 mM $CaCl_2$; 1 mM $MgCl_2$; 5 mM KCl; 0.2% BSA; 4 µg/mL Leupeptin (SIGMA); 10 µM Phosphoramidon (Boehringer Mannheim); 40 µg/mL Bacitracin (SIGMA); 5 µg/mL Aprotinin (SIGMA); and 10 mM Pefabloc (Boehringer Mannheim). One hundred µL of membrane binding buffer containing 10-40/µg membrane protein was added, followed by 100 µM 125I-NDP-α-MSH to final concentration of 100 pM. The resulting mixture was vortexed briefly and incubated for 90-120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 µL per well) with room temperature of filter wash having the composition: 50 mM Tris-HCl pH 7.2 and 20 mM NaCl. The filter was dried, and the bottom sealed and 50 µL of Packard Microscint-20 was added to each well. The top was sealed and the radioactivity quantitated in a Packard Topcount Microplate Scintillation counter.

B. Functional Assay

Functional cell based assays were developed to determine the efficacy of agonists and to discriminate melanocortin receptor agonists from antagonists.

Cells (for example, CHO- or L-cells or other eukaryotic cells) expressing a human melanocortin receptor (see e.g. Yang-Y K; Ollmann-M M; Wilson-B D; Dickinson-C; Yamada-T; Barsh-G S; Gantz-I; Mol-Endocrinol. 1997

March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/mL bovine serum albumin. Cells were counted and diluted to 1 to $5 \times 10^6$/mL. The phosphodiesterase inhibitor 3-isobutyl-1-methylxanthine was added to cells to 0.6 mM.

1. Agonist Assay Test compounds were diluted in DMSO ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP. cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a full agonist with an efficacy of 100%. The $EC_{50}$ is defined as the compound concentration which results in half maximal stimulation, when compared to its own maximal level of stimulation. Compounds that produce near 0% response are expected to be antagonist which will be further confirmed in the antagonist mode of the functional assay.

2. Antagonist Assay: Antagonist activity was defined as the ability of a compound to block cAMP production in response to alpha-MSH or any agonist. A solution of the test compound and suspension of receptor containing cells were prepared and mixed as described above; the mixture was incubated for 15 min, and an $EC_{50}$ dose of alpha-MSH (approximately 10 nM alpha-MSH) was added to the cells. The assay was terminated at 45 minutes and cAMP quantitated as above. Percent inhibition was determined by comparing the amount of cAMP produced in the presence to that produced in the absence of test compound. Antagonist is defined as a compound that by itself does not produce agonist-like response, and in combination with an agonist the compound should inhibit the agonist-induced response.

The compounds of the present invention, including the compounds in Examples 1-100, were tested and found to bind to the melanocortin-4 receptor with $IC_{50}$ values less than 10 µM. The agonist compounds of the present invention, including the compounds in Examples 1-100, were also tested in the functional assay and found to activate the melanocortin-4 receptor with $EC_{50}$ values less than 5 µM.

The antagonist compounds of the present invention were tested in the functional assay and found generally not to activate the melanocortin-4 receptor with an efficacy<5%, and generally have an $IC_{50}$ from the antagonist assay of less than 10 uM.

C. In Vivo Food Intake and Body Weight Models.

1) Food intake and body weight in rats. Sprague Dawley rats are administered test compound one hour prior to onset of dark cycle (12 hours). Food intake is determined either by measurement of the remaining amount of preweighed food the morning following the dosing or by using a computerized system in which each rat's food is placed on a computer monitored balance. Cumulative food intake for 16 h post compound administration is measured. In some cases, food intake measurements are followed as long as 2 weeks. Body weight is measured daily; in some cases, adiposity is measured by DEXA scan analysis, tissue weights and plasma drug levels are measured. Animals can be dosed by a number of routes of administration. The routes of administration include intravenous (IV), intraperitoneal (IP), subcutaneous (SC) and intracerebral ventricular (ICV).

Compounds useful for treating obesity and obesity related disorders in the present invention decrease food intake acutely by at least 20% and/or decrease body weight in a 2 week period by at least 4% relative to placebo.

2) Food intake in diet induced obese mice. Male C57/B16J mice maintained on a high fat diet (30-60% fat calories) are dosed with test compound for 1 to 30 days. Food intake and body weight are measured overnight and sometimes daily as long as 30 days, Biochemical parameters relating to obesity, including leptin, insulin, triglyceride, free fatty acid, cholesterol and serum glucose levels and pharmacokinetic parameters may be determined. Animals can be dosed by a number of routes of administration. The routes of administration include intravenous (IV), intraperitoneal (IP), subcutaneous (SC) and intracerebral ventricular (ICV). Biochemical parameters relating to obesity, including leptin, insulin, triglyceride, free fatty acid, cholesterol and serum glucose levels are determined.

Compounds useful for treating obesity and obesity related disorders in the present invention decrease body weight by at least 4% relative to placebo.

D. Male Sexual Dysfunction: Mouse Electrically Stimulated Cavernosal Nerve (ESCN) Assay Male C57BL6 mice are anesthetized, the carotid artery is exposed and cannulated for measurement of arterial pressure (MAP). A 30 G needle attached to PE10 tubing, filled with heparinized saline, was inserted into the artery and glued in place. This tubing was connected to a pressure transducer and amplifier to measure direct MAP on a Gould 8 channel oscilloscope connected to a computer using the Po-ne-mah software to collect the data at one minute intervals. Another PE10 line attached to a 30 G needle was inserted into the jugular vein for compound or vehicle administration. The cavernous nerve and penile body were exposed through a midline incision. Surrounding muscles were cauterized and removed for visualization of the cavernous nerve, which arises from the ipsilateral pelvic ganglion and is situated dorsal to the prostate. Another 30 G needle attached to PE10 tubing, filled with heparinized saline, was inserted into the base of the corpus cavernosum near the crura and connected to the Gould system. A slight increase in intercavernous pressure (ICP) of approximately 5 to 10 mmHg is observed once this cannula is inserted into the corpus cavernosum. Heparinized saline (200 units/mL) was flushed through the cannula to assure proper placement of the cannula, inducing tumescence. The cavernous nerve was then isolated using curved #5 Dumont forceps and placed on a modified fixed position bipolar silver electrode (Harvard Apparatus). The electrodes are encased in plastic to allow stimulation of the nerve without additional stimulation of surrounding tissues. The electrode was advanced and held by a micromanipulator and was attached to a square wave stimulator to deliver electrical impulses at stimulation parameters ranging between 0.5 to 6.0 v, 2 to 16 Hz, 1 ms, for 30 seconds. Electrical stimulations were administered to individual animals with 5 minute intervals between stimulations. Responses reported at each time point represent the mean of the two stimulations. ICP, MAP and ICP/MAP responses were continuously recorded at one second intervals for the duration of the experiment.

Measurements of ICP, MAP and ICP/MAP ratio are analyzed and responses compared to nerve stimulation in the presence and absence of compound or vehicle. For each parameter monitored, responses evoked by duplicate electrical stimulations were averaged, and the mean values were used for comparison. Response segments of 10 s of baseline+ 30 s stimulation+150 s post-stimulation were used to evaluate changes in ICP in response to electrical stimulation of the cavernous nerve. To assess direct effects of compound administration on ICP, a 300 s pre-compound response segment was compared to a comparable segment immediately after compound administration.

Compounds useful for treating male sexual dysfunction in the present invention increase intracavernous pressure by at least 25% for a time period of at least 15 minutes relative to placebo.

E. Models of Female Sexual Dysfunction

Rodent assays relevant to female sexual receptivity include the behavioral model of lordosis and direct observations of copulatory activity. There is also an urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276-R1285, 1991; McKenna K E et al, *Modulation By Peripheral Serotonin of The Threshold For Sexual Reflexes In Female Rats*, Pharm. Bioch. Behav., 40:151-156, 1991; and Takahashi L K et al, *Dual Estradiol Action In The Diencephalon And The Regulation Of Sociosexual Behavior In Female Golden Hamsters*, Brain Res., 359:194-207, 1985.

F. Model of Cachexia

Rodent assays relevant to cachexia include the tumor cachexia model, in which cells derived from a tumor were injected into mice. Over a period of 1-3 weeks, a tumor will form and grow in the implanted mice. Tumor-bearing mice will exhibit reduced food intake and reduced body weight. By treating the tumor-bearing mice with an effective MC4R antagonist, food intake will be increased and body weight will be increased. This animal model of cachexia is described in Cone, R. D. et al, *Role of the Central Melanocortin System in Cachexia*, Cancer Research 61, 1432-38, Feb. 15, 2001.

EXAMPLES OF PHARMACEUTICAL COMPOSITIONS

As a specific embodiment of an oral composition of a composition of the present invention, 5 mg of Example 10 is formulated with sufficient finely divided lactose to provide a total amount of 580 to 590 mg to fill a size O hard gelatin capsule.

As another specific embodiment of an oral composition of a compound of the present invention, 2.5 mg of Example 1 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the subject or mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula IIIa or IIIb of the indicated trans relative stereochemical configuration:

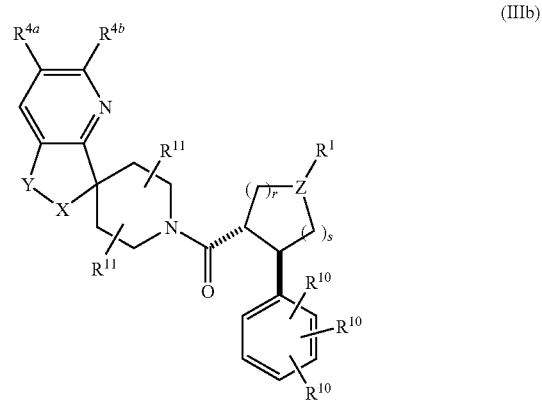

or a pharmaceutically acceptable salt thereof; wherein
X is oxygen or $CH_2$;
Y is $C(R^6)_2$ or $C=C(R^6)_2$;
Z is independently selected from the group consisting of:
  (1) CH, and
  (2) N,
provided that when Z is N, $R^1$ is not —$NR^7C_{2-7}$ heterocycloalkyl;
$R^1$ is selected from the group consisting of
  (1) $C_{1-6}$alkyl,
  (2) —$N(R^7)C_{2-7}$heterocycloalkyl,
  (3) —$(CH_2)_n C_{2-7}$heterocycloalkyl,
  (4) —$C(O)C_{1-6}$alkyl,
  (5) —$C(O)$heteroaryl,
wherein heteroaryl is unsubstituted or substituted with one to three groups independently selected from $R^3$, and wherein alkyl and heterocycloalkyl are unsubstituted or substituted with one to three groups independently selected from $R^3$ and oxo;
$R^3$ is selected from the group consisting of:
  (1) hydrogen,
  (2) $C_{1-8}$ alkyl,
  (3) —$(CH_2)_n$-phenyl,
  (4) —$(CH_2)_n$-naphthyl, (5) —(CH$_2$)$_n$-heteroaryl,
(6) —(CH$_2$)$_n$C$_{2-7}$ heterocycloalkyl,
(7) —(CH$_2$)$_n$C$_{3-7}$ cycloalkyl,
(8) halogen,
(9) OR$^5$,
(10) —(CH$_2$)$_n$N(R$^5$)$_2$,
(11) —(CH$_2$)$_n$C≡N,
(12) —(CH$_2$)$_n$C(O)OR$^5$,
(13) —(CH$_2$)$_n$OC(O)R$^5$,
(14) NO$_2$,
(15) —(CH$_2$)$_n$NR$^5$S(O)$_p$R$^5$,
(16) —(CH$_2$)$_n$N(S(O)$_p$R$^5$)$_2$,
(17) —(CH$_2$)$_n$S(O)$_p$N(R$^5$)$_2$,
(18) —(CH$_2$)$_n$S(O)$_p$R$^5$,
(19) —(CH$_2$)$_n$NR$^5$C(O)N(R$^5$)$_2$,
(20) —(CH$_2$)$_n$C(O)N(R$^5$)$_2$,
(21) —(CH$_2$)$_n$NR$^5$C(O)R$^5$,
(22) —(CH$_2$)$_n$NR$^5$CO$_2$R$^5$,
(23) —(CH$_2$)$_n$NR$^5$C(O)-heteroaryl,
(24) —(CH$_2$)$_n$C(O)NR$^5$N(R$^5$)$_2$,
(25) —(CH$_2$)$_n$C(O)NR$^5$NR$^5$C(O)R$^5$,
(26) O(CH$_2$)$_n$C(O)N(R$^5$)$_2$,
(27) CF$_3$,
(28) CH$_2$CF$_3$,
(29) OCF$_3$, and
(30) OCH$_2$CF$_3$,
wherein phenyl, naphthyl, and heteroaryl are unsubstituted or substituted with one to three substituents independently selected from halogen, hydroxy, C$_{1-4}$ alkyl, trifluoromethyl, and C$_{1-4}$ alkoxy, and wherein alkyl, cycloalkyl, heterocycloalkyl, and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;

R$^{4a}$ and R$^{4b}$ are independently selected from the group consisting of:
(1) hydrogen,
(2) C$_{1-8}$ alkyl,
(3) halogen,
(4) CF$_3$,
wherein alkyl is unsubstituted or substituted with one to three substituents independently selected from halogen, hydroxy, C$_{1-4}$ alkyl, trifluoromethyl, and C$_{1-4}$ alkoxy;

each R$^5$ is independently selected from the group consisting of:
(1) hydrogen,
(2) C$_{1-8}$ alkyl,
(3) —(CH$_2$)$_n$C$_{3-7}$ cycloalkyl,
(4) —(CH$_2$)$_n$C$_{2-7}$ heterocycloalkyl,
(5) —(CH$_2$)$_n$-phenyl,
(6) —(CH$_2$)$_n$-naphthyl,
(7) —(CH$_2$)$_n$-heteroaryl, and
(8) —(CH$_2$)$_n$C$_{3-7}$ bicycloalkyl,
wherein alkyl, phenyl, heteroaryl, heterocycloalkyl, naphthyl, cycloalkyl, bicycloalkyl and (CH$_2$) are unsubstituted or substituted with one to three groups independently selected from halogen, C$_{1-4}$ alkyl, hydroxy, and C$_{1-4}$ alkoxy, or wherein two R$^5$ groups together with the atom to which they are attached form a 4- to 8-membered mono- or bicyclic ring system optionally containing an additional heteroatom selected from 0, S, and —NC$_{1-4}$ alkyl;

each R$^6$ is independently selected from the group consisting of: hydrogen,
(2) —(CH$_2$)$_n$-heteroaryl,
(3) —(CH$_2$)$_n$C(O)N(R$^5$)$_2$,
(4) —(CH$_2$)$_n$C(O)N(R$^5$)N(R$^5$)C(O)R$^5$,
(5) —(CH$_2$)$_n$CN,
(6) —(CH$_2$)$_n$N(R$^5$)$_2$,
(7) —(CH$_2$)$_n$N(R$^5$)C(O)R$^5$,
wherein heteroaryl is unsubstituted or substituted with one to three groups independently selected from R$^3$, and wherein any methylene carbon (CH$_2$) in R$^6$ is unsubstituted or substituted with one to two groups independently selected from halogen, hydroxy, and C$_{1-4}$ alkyl;

each R$^7$ and R$^8$ is independently selected from the group consisting of:
(1) hydrogen,
(2) C$_{1-6}$alkyl,
(3) C$_{3-7}$cycloalkyl,
(4) C$_{2-7}$heterocycloalkyl,
(5) phenyl,
(6) naphthyl, and
(7) heteroaryl,
wherein phenyl, naphthyl, and heteroaryl are unsubstituted or substituted with one to three groups independently selected from R$^3$, and wherein alkyl, cycloalkyl, and heterocycloalkyl are unsubstituted or substituted with one to three groups independently selected from R$^3$ and oxo;

each R$^{10}$ is independently selected from the group consisting of:
(1) hydrogen,
(2) C$_{1-6}$alkyl,
(3) (CH$_2$)$_n$phenyl,
(4) halogen,
(5) —OR$^5$,
(6) (CH$_2$)$_n$CN,
(7) CF$_3$,
(8) CH$_2$CF$_3$,
(9) OCF$_3$, and
(10) OCH$_2$CF$_3$,
wherein phenyl is unsubstituted or substituted with one to three substituents independently selected from halogen, hydroxy, C$_{1-4}$ alkyl, trifluoromethyl, and C$_{1-4}$ alkoxy, and wherein alkyl and (CH$_2$) are unsubstituted or substituted with one to three substituents independently selected from halogen, hydroxy, oxo, C$_{1-4}$ alkyl, trifluoromethyl, and C$_{1-4}$ alkoxy, or wherein two substituents when on the same methylene (CH$_2$) group are taken together with the carbon atom to which they are attached to form a cyclopropyl group;

each R$^{11}$ is hydrogen;

r is 2;

s is 1;

n is 0, 1, 2, or 3; and p is 0, 1, or 2.

2. A compound of claim 1 which is
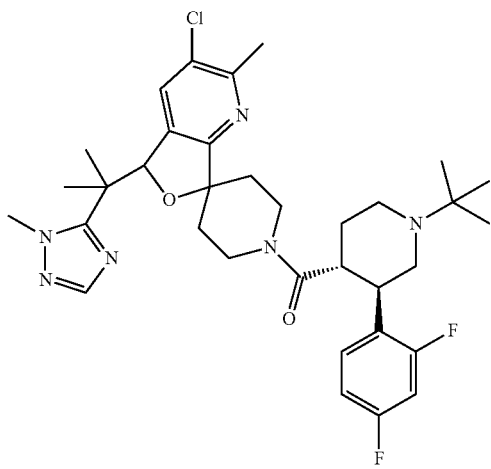
or a pharmaceutically acceptable salt thereof.
3. A compound of claim 2 which is:
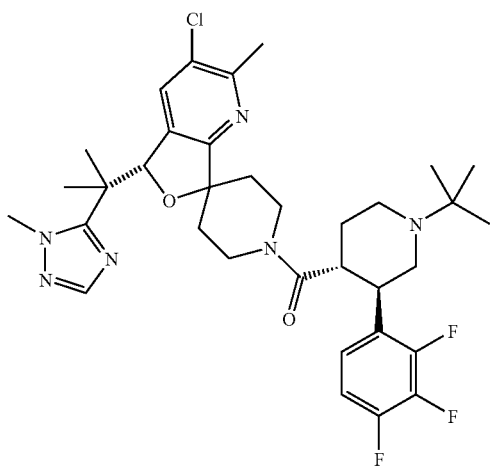
or a pharmaceutically acceptable salt thereof.
4. A compound of claim 2 which is:
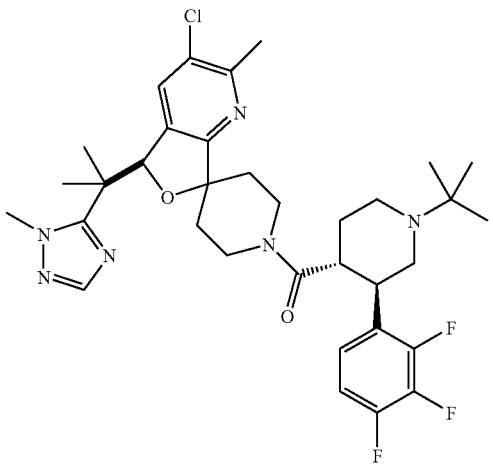
or a pharmaceutically acceptable salt thereof.
5. A compound of claim 1 selected from the group consisting of:
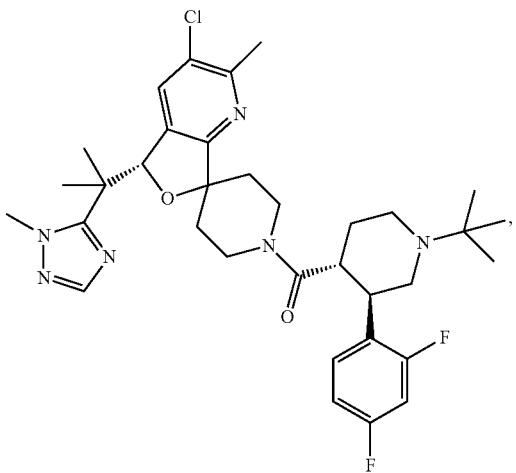

171
-continued
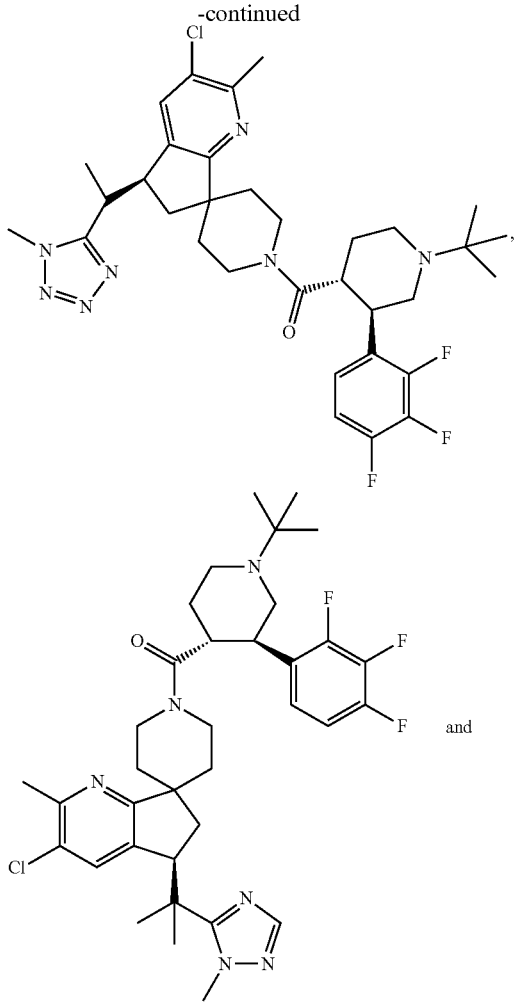
172
-continued
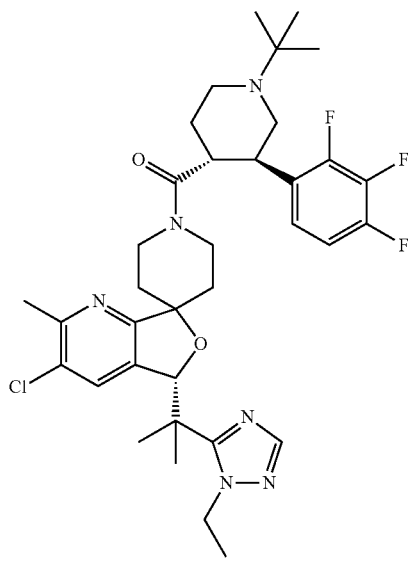
or a pharmaceutically acceptable salt thereof.
6. A pharmaceutical composition which comprises a compound of claim 1 and a pharmaceutically acceptable carrier.
7. A compound of claim 2 wherein the pharmaceutically acceptable salt thereof is the bis trifluoroacetic acid salt.
* * * * *